United States Patent
Schwiebert et al.

(10) Patent No.: US 10,369,145 B2
(45) Date of Patent: Aug. 6, 2019

(54) COUMARIN DERIVATIVES AND METHODS OF USE IN TREATING HYPERPROLIFERATIVE DISEASES

(71) Applicant: DISCOVERYBIOMED, INC., Birmingham, AL (US)

(72) Inventors: Erik Schwiebert, Birmingham, AL (US); John Streiff, Birmingham, AL (US); John Dixon, Leicestershire (GB); Hongwu Gao, Shanghai (CN); Joseph P. Ritchie, Vestavia Hills, AL (US); Eric C. Seales, Birmingham, AL (US); Deborah Mai, Birmingham, AL (US)

(73) Assignee: DISCOVERYBIOMED, INC., Birmingham, AL (US)

(*) Notice: Subject to any disclaimer, the term of this patent is extended or adjusted under 35 U.S.C. 154(b) by 34 days.

(21) Appl. No.: 14/775,050

(22) PCT Filed: Mar. 14, 2014

(86) PCT No.: PCT/US2014/027154
§ 371 (c)(1),
(2) Date: Sep. 11, 2015

(87) PCT Pub. No.: WO2014/152278
PCT Pub. Date: Sep. 25, 2014

(65) Prior Publication Data
US 2016/0038475 A1    Feb. 11, 2016

Related U.S. Application Data

(60) Provisional application No. 61/788,398, filed on Mar. 15, 2013.

(51) Int. Cl.
| | | |
|---|---|---|
| A61K 31/47 | (2006.01) |
| A01N 43/42 | (2006.01) |
| A61K 31/4709 | (2006.01) |
| C07D 417/04 | (2006.01) |
| C07D 405/04 | (2006.01) |
| C07D 413/04 | (2006.01) |
| C07D 417/14 | (2006.01) |
| C07D 471/04 | (2006.01) |
| C07D 491/052 | (2006.01) |
| C07D 493/04 | (2006.01) |
| C07D 498/04 | (2006.01) |
| A61K 31/422 | (2006.01) |
| A61K 31/427 | (2006.01) |
| A61K 31/4439 | (2006.01) |

(52) U.S. Cl.
CPC ........ *A61K 31/4709* (2013.01); *A61K 31/422* (2013.01); *A61K 31/427* (2013.01); *A61K 31/4439* (2013.01); *C07D 405/04* (2013.01); *C07D 413/04* (2013.01); *C07D 417/04* (2013.01); *C07D 417/14* (2013.01); *C07D 471/04* (2013.01); *C07D 491/052* (2013.01); *C07D 493/04* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 2003/0055263 A1 | 3/2003 | Priepke et al. | |
| 2006/0079543 A1 | 4/2006 | Sum et al. | |
| 2007/0032518 A1 | 2/2007 | Norman et al. | |
| 2009/0012148 A1* | 1/2009 | Maxfield ............... | A61K 31/53 514/422 |
| 2016/0024065 A1 | 1/2016 | Schwiebert et al. | |

FOREIGN PATENT DOCUMENTS

| | | | |
|---|---|---|---|
| CN | 101039919 A | 9/2007 | |
| CN | 101076703 A | 11/2007 | |
| CN | 101351208 A | 1/2009 | |
| CN | 105121437 | 12/2015 | |
| CN | 105246887 | 1/2016 | |
| IN | 7593DELNP2015 | 1/2016 | |
| JP | 55066580 | 5/1980 | |
| WO | 03006443 A2 | 1/2003 | |
| WO | 03066630 | 8/2003 | |
| WO | WO 03066630 A2 * | 8/2003 | ........... C07D 417/14 |
| WO | 03105842 A1 | 12/2003 | |
| WO | 2006044456 A1 | 4/2006 | |
| WO | 2007053847 A2 | 5/2007 | |
| WO | 2009076665 A1 | 6/2009 | |
| WO | 2010111713 A2 | 9/2010 | |

(Continued)

OTHER PUBLICATIONS

Solak et al. (Medical Hypotheses, 2010, 74, 314-317).*
Fayad et al. (Chem Biol Drug Des, 2011, 78, 547-557).*
Edcer et al. (Nat Rev Nephrol, 2009, 5, 221-228).*
CN201480009649.8, "Office Action", dated Nov. 15, 2016, 29 pages.
EP14767955.9, "Extended European Search Report", dated Dec. 12, 2016, 13 pages.
EP14767955.9, "Partial Supplementary European Search Report", dated Sep. 5, 2016, 10 pages.
EP14768111.8, "Partial Supplementary European Search Report", dated Nov. 2, 2016, 12 pages.

(Continued)

*Primary Examiner* — Dennis Heyer
*Assistant Examiner* — Daniel M Podgorski
(74) *Attorney, Agent, or Firm* — Kilpatrick Townsend & Stockton LLP

(57) ABSTRACT

Coumarin derivative compounds and methods for the treatment of hyperproliferative diseases, such as cancer, polycystic kidney disease, and fibrosis of different tissues (e.g., idiopathic pulmonary fibrosis), are provided. The methods include administering to a subject a compound as described herein. Also provided are methods for inhibiting the interaction between two or more heat shock protein chaperones in a cell.

5 Claims, 10 Drawing Sheets

(56) References Cited

FOREIGN PATENT DOCUMENTS

| WO | 2012171954 | 12/2012 |
| WO | 2014152213 | 9/2014 |
| WO | 2014152278 | 9/2014 |
| WO | 2014152278 | 11/2014 |

OTHER PUBLICATIONS

Lin, et al., "Double Functional Group Transformations for Fluorescent Probe Construction: A Fluorescence Turn-On Probe for Thioureas", Chemistry—A European Journal, vol. 16, No. 22, Jun. 11, 2010, pp. 6454-6457.
Rao, et al., "Microwave-assisted synthesis of some -chloro-3-[2-(substituted anilino)-1,3-thiazol-4-y1]-2H-1-benzopyran -2-ones as antibacterial agents", Indian Journal of Heterocyclic Chemistry, National Academy of Chemistry and Biology vol. 17, No. 4, Jan. 1, 2008, pp. 397-400.
Yusufzai, et al., "3-(2-Methylamino-1,3-thiazol-4-yl)-2 H -chromen-2-one", Acta Crystallographica Section E Structure Reports Online, vol. 68, No. 8,, Jul. 10, 2012, pp. 2416-2417.
U.S. Appl. No. 14/775,010, "Non Final Office Action", dated Oct. 7, 2016, 9 pages.
Ambre, et al., "Identification of new checkpoint kinase-1 (Chk1) inhibitors by docking, 3D-QSAR, and pharmacophore-modeling methods", Canadian Journal of Chemistry, vol. 90, No. 8, 2012, pp. 675-692.
Koti, et al., "Intramolecular Amidation: Synthesis of Novel Thiazole-Fused Diazepinones", Synthetic Communications, vol. 37, No. 1, Jan. 1, 2007, 8 pages.
Matic, CA159:437927, abstract only of J Blochem &Mol Tox, vol. 26, No. 8, 2012, pp. 322-330.
Mladenovic, et al., "Biochemical and pharmacological evaluation of 4-hydroxychromen-2-ones bearing polar C-3 substituents as anticoagulants", E J Med Chem, vol. 54, Aug. 2012, pp. 144-158.
Mohamed, et al., "Synthesis, Reactions and Antimicrobial Activities of 8-Ethoxycoumarin", Molecules, vol. 17, No. 1, 2012, pp. 971-988.
Raza, ISRN Pharmacology, 2012, pp. 1-11.
CN201480015013.4, Office Action dated Jan. 24, 2017, 30 pages.
EP14768111.8, Extended European Search Report dated Feb. 15, 2017, 20 pages.
U.S. Appl. No. 14/775,010, Final Office Action dated Mar. 17, 2017, 7 pages.
[online] Registry via STN, RN 403721-73-3, Apr. 3, 2002.
[online] Registry via STN, RN 403721-74-4, Apr. 3, 2002.
[online] Registry via STN, RN 724744-64-3, Aug. 10, 2004.
[online] Registry via STN, RN 313954-55-1, Jan. 15, 2001.
[online] Registry via STN, RN 313954-56-2, Jan. 15, 2001.
[online] Registry via STN, RN 312703-21-2, Jan. 4, 2001.
[online] Registry via STN, RN 325473-18-5, Mar. 4, 2001.
[online] Registry via STN, RN 325804-06-6, Mar. 6, 2001.
[online] Registry via STN, RN 325804-07-7, Mar. 6, 2001.
Abraham et al., Cystic fibrosis hetero- and homozygosity is associated with inhibition of breast cancer growth, Nature Medicine, vol. 2, No. 5, May 1996, pp. 593-596.
Chinese Application No. 201480009649.8, Office Action dated Dec. 31, 2015, 2 pages.
Desai et al., A convenient, rapid and eco-friendly synthesis of isoxazoline heterocyclic moiety containing bridge at 2°-amine as potential pharmacological agent, Journal of the Iranian Chemical Society, vol. 5, No. 1, 2008, pp. 67-73.
Ding et al., Methylation profile of the promoter CpG islands of 14 "drug-resistance" genes in hepatocellular carcinoma, World Journal of Gastroenterology, vol. 10, No. 23, Dec. 2004, pp. 3433-3440.
Eriksson et al., Specific in vivo phosphorylation sites determine the assembly dynamics of vimentin intermediate filaments, J. Cell Sci., vol. 117, Pt. 6, Feb. 29, 2004, pp. 919-932.
Goto et al., Phosphorylation and reorganization of vimentin by p21-activated kinase (PAK), Genes Cells, vol. 7, No. 2, Feb. 2002, pp. 91-97.
Hanmantgad et al., Biomimetic thiazolyl coumarins, National Academy Science Letters, vol. 7, No. 3, 1984, pp. 77-78.
Lahat et al., Vimentin Is a Novel Anti-Cancer Therapeutic Target; Insights from in Vitro and in Vivo Mice Xenograft Studies, PLoS One, vol. 5, No. 4, Apr. 16, 2010, 19 pages.
Lee et al., Cdk5 mediates vimentin Ser56 phosphorylation during GTP-induced secretion by neutrophils, J Cell Physiol., vol. 227, No. 2, Feb. 2012, pp. 739-750.
Li et al., Critical role of vimentin phosphorylation at Ser-56 by p21-activated kinase in vimentin cytoskeleton signaling, J Biol. Chem., vol. 281, No. 45, Nov. 10, 2006, pp. 34716-34724.
Li et al., Cystic fibrosis transmembrane conductance regulator gene mutation and lung cancer risk, Lung Cancer, vol. 70, No. 1, Oct. 2010, pp. 14-21.
McWilliams et al., Cystic fibrosis transmembrane conductance regulator (CFTR) gene mutations and risk for pancreatic adenocarcinoma, Cancer, vol. 116, No. 1, Jan. 1, 2010, pp. 203-209.
McWilliams et al., Risk of malignancy in first-degree relatives of patients with pancreatic carcinoma, Cancer, vol. 104, No. 2, Jul. 15, 2005, pp. 388-394.
Mishra et al., Global methylation pattern of genes in androgen-sensitive and androgen-independent prostate cancer cells, Molecular Cancer Therapeutics, vol. 9, No. 1, Jan. 2010, pp. 33-45.
Mori et al., A Combination Strategy to Inhibit Pim-1: Synergism between Noncompetitive and ATP-Competitive Inhibitors, Chem. Med. Chem., vol. 8, No. 3, Feb. 22, 2013, pp. 484-496.
Moribe et al., Methylation of multiple genes as molecular markers for diagnosis of a small, well-differentiated hepatocellular carcinoma, International Journal of Cancer, vol. 125, No. 2, Jul. 15, 2009, pp. 388-397.
Neglia et al., The risk of cancer among patients with cystic fibrosis. Cystic Fibrosis and Cancer Study Group, The New England Journal of Medicine, vol. 332, No. 8, Feb. 23, 1995, pp. 494-499.
Oh et al., Association of CFTR gene polymorphisms with papillary thyroid cancer, Oncology Letters, vol. 3, No. 2, Feb. 2012, pp. 455-461.
Omary et al., "Heads and tails" of intermediate filament phosphorylation: multiple sites and functional insights, Trends Bio. Chem. Sci., vol. 31, No. 7, Jul. 2006, pp. 383-394.
Padua et al., The cystic fibrosis delta F508 gene mutation and cancer, Human Mutation, vol. 10, No. 1, 1997, pp. 45-48.
Panigrahi et al., 4-(3'-Coumarinyl)-2-arylaminothiazoles and some of their derivatives, Journal of the Indian Chemical Society, vol. 48, No. 7, 1971, pp. 665-668.
International Application No. PCT/US2014/027154, International Preliminary Report on Patentability dated Sep. 24, 2015, 9 pages.
International Application No. PCT/US2014/027154, International Search Report and Written opinion dated Sep. 18, 2014, 13 pages.
Qiao et al., Cystic fibrosis transmembrane conductance regulator (CFTR) gene 5T allele may protect against prostate cancer: a case-control study in Chinese Han population, Journal of Cystic Fibrosis, vol. 7, No. 3, May 2008, pp. 210-214.
Son et al., Promoter hypermethylation of the CFTR gene and clinical/pathological features associated with non-small cell lung cancer, Respirology, vol. 16, No. 8, Nov. 2011, pp. 1203-1209.
Srimanth et al., Synthesis of some new types of thiazolyl coumarins, Indian Journal of Chemistry, vol. 388, No. 4, 1999, pp. 473-475.
Thaiparambil et al., Withaferin a inhibits breast cancer invasion and metastasis at sub-cytotoxic doses by inducing vimentin disassembly and serine 56 phosphorylation, Int. J. Cancer, vol. 129, No. 11, Dec. 2011, pp. 2744-2755.
Venugopala et al., Synthesis and evaluation of some substituted 2-arylamino coumarinyl thiazoles as potential NSAIDs, Asian Journal of Chemistry, vol. 16, No. 2, 2004, pp. 872-876.
Warren et al., Frequency of carriers of cystic fibrosis gene among patients with myeloid malignancy and melanoma, BMJ, vol. 302, No. 6779, Mar. 30, 1991, pp. 760-761.
Xie et al., CFTR suppresses tumor progression through miR-193b targeting urokinase plasminogen activator (uPA) in prostate cancer, Oncogene, vol. 32, No. 18, May 2, 2013, pp. 1-10.

(56) References Cited

OTHER PUBLICATIONS

Yang et al., Stimulation of Airway and Intestinal Mucosal Secretion by Natural Coumarin CFTR Activators, Frontiers in Pharmacology, vol. 2, No. 52, Sep. 27, 2011, 5 pages.
Yasui et al., Protein kinases required for segregation of vimentin filaments in mitotic process, Oncogene, vol. 20, No. 23, May 24, 2001, pp. 2868-2876.
Australian Patent Application No. 2014240003, Examination report No. 1 dated Sep. 12, 2017, 6 pages.
Deng, "Stimulation of airway and intestinal mucosal secretion by natural coumarin CFTR activators", J. Med. Chem., 49(5):1684-1692, Feb. 15, 2006.
Wang, et al., "CFTR and cystic fibrosis", Int. J. Pathol. Clin. Med., 26(2):142-145, Apr. 30, 2006 [English abstract].
CAS Registry No. 364338-99-8; STN entry date Oct. 24, 2001; Chemical Name: 2H-1-Benzopyran-2-one, 7-(diethylamino)-3-[2-[(2-methoxypphenyl)amino]-4-thiazolyl]-.
CAS Registry No. 325804-09-9; STN entry date Mar. 6, 2001; Chemical Name: 2H-1-Benzopyran-2-one, 8-methoxy-3-[2-[(2-methoyphenyl)amino]-4-thiazolyl]-.
CN201480015013.4, Office Action dated Jul. 21, 2017, 9 pages with English translation.
EP14768111.8, "Communication pursuant to Article 94(3)," Nov. 12, 2018, 10 pages.
European Patent Application No. EP14767955.9, "Office Action", dated Sep. 14, 2018, 5 pages.
Japanese Patent Application No. JP2016-502351, "Notice of Allowance", dated Sep. 11, 2018, 3 pages.
Ramanna et al., Synthesis of N-(4-2H-1-Benzopyran-2-One-2-Thiazoly)Phthalimides, Phosphorus, Sulfur and Silicon, 1995, vol. 107, pp. 197-204.

* cited by examiner

COUMARIN DERIVATIVES AND METHODS OF USE IN TREATING HYPERPROLIFERATIVE DISEASES

CROSS-REFERENCE TO PRIORITY APPLICATION

This application claims priority to U.S. Provisional Application No. 61/788,398, filed Mar. 15, 2013, which is incorporated herein by reference in its entirety.

BACKGROUND

A variety of diseases involve the hyperproliferation of cells. Cancer, for example, is a commonly known hyperproliferative disease. Cancer is a large, heterogeneous class of diseases in which a group of cells display uncontrolled growth, resulting in an invasion that intrudes upon and destroys adjacent tissues. The cells often metastasize, wherein the tumor cells spread to other locations in the body via the lymphatic system or through the bloodstream. Cancer can be caused by environmental factors or genetic factors (or a combination of both). Common environmental factors leading to cancer include tobacco use, poor diet and obesity, infection, radiation, lack of physical activity, and environmental pollutants. These environmental factors may cause or enhance abnormalities in the genetic material of cells. Cell reproduction is an extremely complex process that is normally tightly regulated by several classes of genes, including oncogenes and tumor suppressor genes. Abnormalities/mutations in these regulatory genes can lead to the development of cancer. A small percentage of cancers, approximately five to ten percent, are entirely hereditary. In 2007, cancer caused about 13% of all human deaths worldwide (7.9 million). Rates are rising as more people live to an old age and as mass lifestyle changes occur in the developing world.

Other forms of hyperproliferative diseases also exist, such as, but not limited to, polycystic kidney disease (PKD) and related cystic kidney diseases. Polycystic kidney disease (PKD or PCKD) is a cystic genetic disorder of the kidneys. There are two types of PKD: autosomal dominant polycystic kidney disease (ADPKD) and the less-common autosomal recessive polycystic kidney disease (ARPKD). Both forms cause hyperproliferation of kidney epithelial cells but neither form is a cancer. It occurs in humans and some other animals. PKD is characterized by the presence of multiple cysts (hence, "polycystic") typically in both kidneys; however, 17% of cases initially present with observable disease in one kidney, with most cases progressing to bilateral disease in adulthood. The cysts are numerous and are fluid-filled, resulting in massive enlargement of the kidneys. The disease can also damage the liver, the pancreas, and, in some rare cases, the vasculature of the heart and the brain. PKD is the most common life-threatening genetic disease and the leading genetic cause of dialysis and transplantation, affecting an estimated 12.5 million people worldwide. In half of the people with PKD, there is no family history of the disease. However, in the dominant form of the disease, it affects multiple family members with variable times of emergence and with some variance in severity.

Other hyperproliferative diseases include fibrosis of different tissues. Fibrosis is the formation of excess fibrous connective tissue in an organ or tissue. Fibrosis can lead to degeneration of the tissue or organ and/or loss of function if it becomes widespread and aggressive. Fibrosis plays a role in a number of diseases states in mammals, including, but not limited to, pulmonary fibrosis, idiopathic pulmonary fibrosis, cirrhosis, endomyocardial fibrosis, vascular or spinal stenosis, mediastinal fibrosis, myelofibrosis, retroperitoneal fibrosis, progressive massive fibrosis, nephrogenic systemic fibrosis, Crohn's Disease, keloid or old myocardial infarction, scleroderma/systemic sclerosis, arthrofibrosis, and adhesive capsulitis.

Such hyperproliferative diseases have been known for decades; however, effective treatments remain elusive.

SUMMARY

Coumarin derivative compounds and methods for the treatment of hyperproliferative diseases, such as cancer, polycystic kidney disease, and fibrosis of different tissues (e.g., idiopathic pulmonary fibrosis), are provided. The methods include administering to a subject a compound as described herein.

A class of CFTR correctors includes compounds of the following formula:

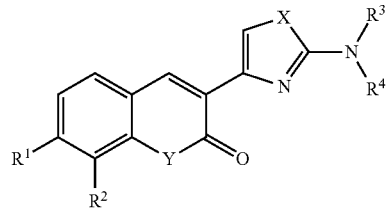

and pharmaceutically acceptable salts or prodrugs thereof. In this class of compounds, $R^1$ is hydrogen, halogen, hydroxyl, substituted or unsubstituted alkoxyl, substituted or unsubstituted amino, substituted or unsubstituted $C_{1-6}$ alkyl, or substituted or unsubstituted heterocycloalkyl; $R^2$ is hydrogen, halogen, hydroxyl, nitro, cyano, azido, thiocyanato, trifluoromethyl, substituted or unsubstituted alkoxyl, substituted or unsubstituted amino, substituted or unsubstituted carbonyl, or substituted or unsubstituted $C_{1-6}$ alkyl; $R^3$ is hydrogen or substituted or unsubstituted $C_{1-6}$ alkyl; $R^4$ is substituted or unsubstituted $C_{1-6}$ alkyl, substituted or unsubstituted aryl, or substituted or unsubstituted heteroaryl; X is S or O; and Y is O or $NCH_3$. Optionally, the compound is selected from the group consisting of:

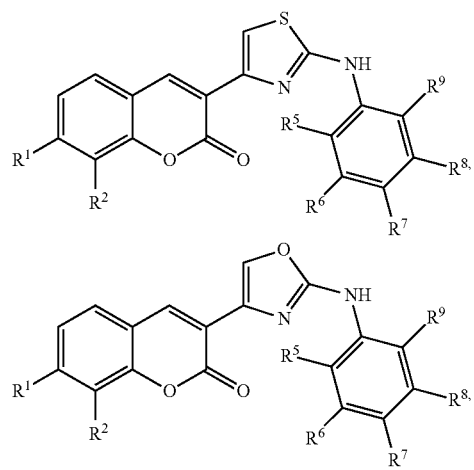

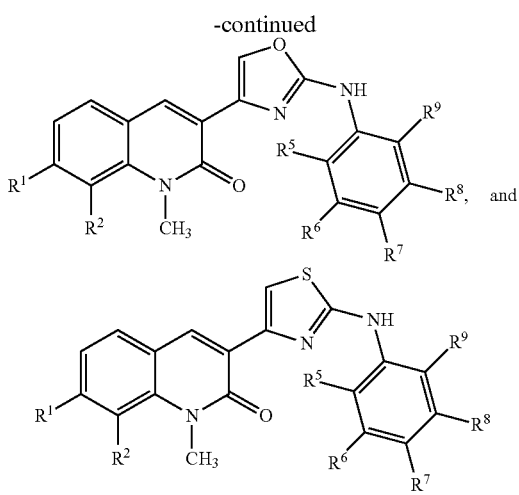

wherein $R^5$, $R^6$, $R^7$, $R^8$, and $R^9$ are each independently selected from hydrogen, halogen, hydroxyl, substituted or unsubstituted alkoxy, cyano, nitro, trifluoromethyl, substituted or unsubstituted carbonyl, substituted or unsubstituted amino, substituted or unsubstituted $C_{1-6}$ alkyl, substituted or unsubstituted $C_{2-6}$ alkenyl, substituted or unsubstituted aryl, substituted or unsubstituted sulfonamide, substituted or unsubstituted sulfonyl, or substituted or unsubstituted thio. Optionally, $R^1$ and $R^2$, $R^5$ and $R^6$, $R^6$ and $R^7$, $R^7$ and $R^8$, or $R^8$ and $R^9$ combine to form a substituted or unsubstituted aryl, substituted or unsubstituted cycloalkenyl, substituted or unsubstituted heteroaryl, or substituted or unsubstituted heterocycloalkyl.

A class of CFTR correctors includes compounds of the following formula:

and pharmaceutically acceptable salts or prodrugs thereof. In this class of compounds, L is a heteroaryl; and $R^5$, $R^6$, $R^7$, $R^8$, and $R^9$ are each independently selected from hydrogen and methoxy.

A class of CFTR correctors includes compounds of the following formula:

and pharmaceutically acceptable salts or prodrugs thereof. In this class of compounds, $X^1$, $X^2$, $X^3$ and $X^4$ are each independently selected from CH and N; Y is O or NR, where R is hydrogen or methyl; $R^2$ is hydrogen, $C_{1-6}$ alkyl, halogen, or trifluoroalkyl; and $R^5$, $R^6$, $R^7$, $R^8$, and $R^9$ are each independently selected from hydrogen and methoxy.

A class of CFTR correctors includes compounds of the following formula:

and pharmaceutically acceptable salts or prodrugs thereof. In this class of compounds, $X^1$ is O or $NCH_3$; $X^2$ is CH or N; Y is O, NH, or $NCH_3$; and $R^5$, $R^6$, $R^7$, $R^8$, and $R^9$ are each independently selected from hydrogen and methoxy.

A class of CFTR correctors includes compounds of the following formula:

and pharmaceutically acceptable salts or prodrugs thereof. In this class of compounds, $R^1$ and $R^2$ are each independently selected from hydrogen, substituted or unsubstituted amino, and substituted or unsubstituted carbonyl.

A class of CFTR correctors includes compounds of the following formula:

and pharmaceutically acceptable salts or prodrugs thereof. In this class of compounds, X is $CH_2$, NH, or O.

A method for the treatment of a hyperproliferative disease in a subject is also described herein. The method for the treatment of a hyperproliferative disease in a subject comprises administering to the subject an effective amount of a compound as described herein. Optionally, the hyperproliferative disease is cancer. Optionally the hyperproliferative disease is polycystic kidney disease. Optionally, the hyperproliferative disease is a fibrosis (e.g., idiopathic pulmonary fibrosis).

Also provided herein are methods of inhibiting the interaction between two or more heat shock protein chaperones in a cell. The methods of inhibiting the interaction between two or more heat shock protein chaperones in a cell comprise contacting a cell with a compound as described herein. Optionally, the two or more heat shock protein chaperones are selected from the group consisting of Hsp-90, Hsp-70, Hsc-70, and Hsp-40. Optionally, the method is performed in vitro. Optionally, the method is performed in vivo.

The details of one or more embodiments are set forth in the drawings and the description below. Other features, objects, and advantages will be apparent from the description and drawings, and from the claims.

DETAILED DESCRIPTION

Figure 1:
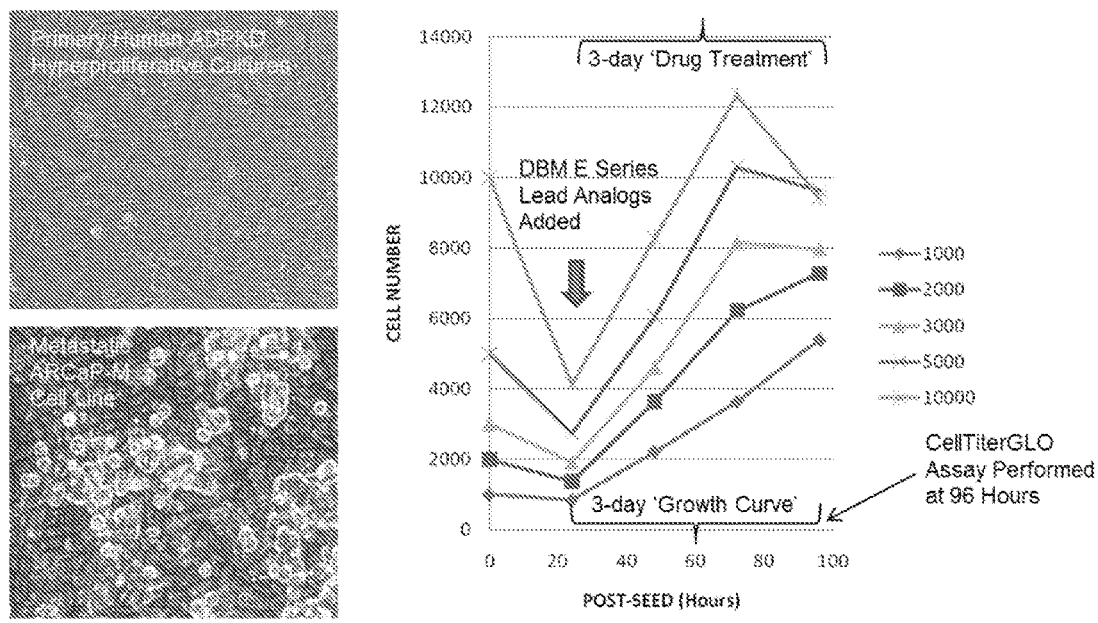
FIG. 1 contains a schematic showing a general approach for the growth curve assay for profiling the compounds (graph on the right), a picture of a primary human ADPKD hyperproliferative culture (photograph on the top left), and a picture of a metastatic ARCaP-M cell line (photograph on the bottom left).

The coumarin derivative compounds and methods described herein are useful in the treatment of hyperproliferative diseases. As used herein, a hyperproliferative disease is any disorder or condition that involves dis-regulated or unregulated but accelerated cell growth (versus the normal condition of cells in normal tissues) that impacts the health of a subject. Such dis-regulated or unregulated and accelerated cell growth may result in the death of the subject. The compounds and methods described herein are useful for treating hyperproliferative disorders that include, but are not limited to, cancer, polycystic kidney disease, and fibrosis (e.g., idiopathic pulmonary fibrosis).

I. Compounds

A class of coumarin derivatives described herein is represented by Formula I:

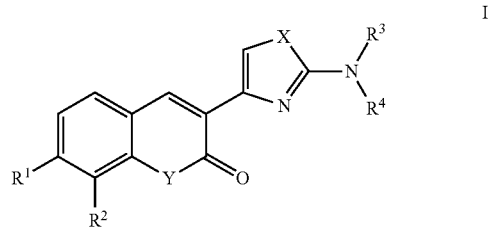

and pharmaceutically acceptable salts or prodrugs thereof.

In Formula I, $R^1$ is hydrogen, halogen, hydroxyl, substituted or unsubstituted alkoxyl, substituted or unsubstituted amino, substituted or unsubstituted $C_{1-6}$ alkyl, or substituted or unsubstituted heterocycloalkyl.

Also, in Formula I, $R^2$ is hydrogen, halogen, hydroxyl, nitro, cyano, azido, thiocyanato, trifluoromethyl, substituted or unsubstituted alkoxyl, substituted or unsubstituted amino, substituted or unsubstituted carbonyl, or substituted or unsubstituted $C_{1-6}$ alkyl.

Additionally, in Formula I, $R^3$ is hydrogen or substituted or unsubstituted $C_{1-6}$ alkyl.

Further, in Formula I, $R^4$ is substituted or unsubstituted $C_{1-6}$ alkyl, substituted or unsubstituted aryl, or substituted or unsubstituted heteroaryl.

Also, in Formula I, X is S or O.

Additionally, in Formula I, Y is O, NH, or $NCH_3$.

As used herein, the terms alkyl and alkenyl include straight- and branched-chain monovalent substituents. Examples include methyl, ethyl, isobutyl, and the like. Ranges of these groups useful with the compounds and methods described herein include $C_1$-$C_8$ alkyl and $C_3$-$C_8$ alkenyl.

Heteroalkyl and heteroalkenyl are defined similarly as alkyl and alkenyl, but can contain O, S, or N heteroatoms or combinations thereof within the backbone. Ranges of these groups useful with the compounds and methods described herein include $C_1$-$C_8$ heteroalkyl and $C_3$-$C_8$ heteroalkenyl.

The term cycloalkyl includes cyclic alkyl groups having a single cyclic ring or multiple condensed rings. Examples include cyclohexyl, cyclopentylethyl, and adamantanyl. A range of these groups useful with the compounds and methods described herein includes $C_3$-$C_9$ cycloalkyl.

The term heterocycloalkyl is defined similarly as cycloalkyl, but can contain O, S, or N heteroatoms or combinations thereof within the cyclic backbone. A range of these groups useful with the compounds and methods described herein includes $C_4$-$C_9$ heterocycloalkyl.

Aryl groups include, for example, phenyl and substituted phenyl. Heteroaryl groups contain O, N, or S heteroatoms, either alone or in combination in five or six membered rings. Examples of heteroaryl groups with one heteroatom include pyridyl, thienyl, and furyl substituted on or joined by any of the available carbon atoms. Examples of heteroaryl groups with more than one heteroatom include pyrimidinyl, oxazolyl, and thiazolyl substituted on or joined by any of the available carbon atoms. Aryl and heteroaryl groups can include additional fused rings. Examples of such groups include indanyl, naphthyl, benzothienyl, quinolinyl, and isomers thereof substituted on or joined by any of the available carbon atoms.

All groups mentioned above can be unsubstituted or substituted with one or more of the following which may the same or different. Examples of appropriate substituents include, but are not limited to, the following: alkoxy (e.g., methoxy), alkyl, aryl, carboxylate, carboxylate ester, cyano, halogen (e.g., chloro, bromo, fluoro, iodo), heteroaryl, nitro, amino, alkylsulfonyl, sulfonamide, reverse sulfonamide, and thio.

In some examples, Formula I is represented by Structure I-A:

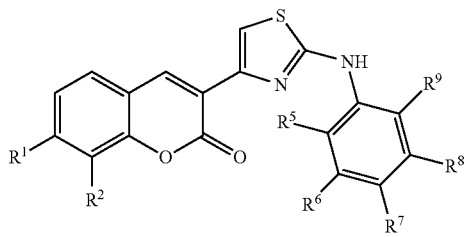

In Structure I-A, $R^1$ and $R^2$ are as defined above for Formula I.

Also in Structure I-A, $R^5$, $R^6$, $R^7$, $R^8$, and $R^9$ are each independently selected from hydrogen, halogen, hydroxyl, substituted or unsubstituted alkoxy, cyano, nitro, trifluoromethyl, substituted or unsubstituted carbonyl, substituted or unsubstituted amino, substituted or unsubstituted $C_{1-6}$ alkyl, substituted or unsubstituted $C_{2-6}$ alkenyl, substituted or unsubstituted aryl, substituted or unsubstituted sulfonamide, substituted or unsubstituted sulfonyl, or substituted or unsubstituted thio. The carbonyl can be a carboxylic acid or an acid derivative. As used herein, an acid derivative refers to a functional derivative of a carboxylic acid such as, for example, an ester or an amide.

In some examples, Formula I is represented by Structure I-B:

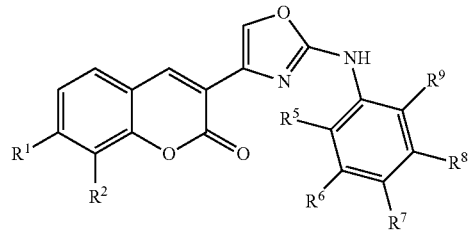

In Structure I-B, $R^1$ and $R^2$ are as defined above for Formula I.

Also in Structure I-B, $R^5$, $R^6$, $R^7$, $R^8$, and $R^9$ are as defined above for Structure I-A.

In some examples, Formula I is represented by Structure I-C:

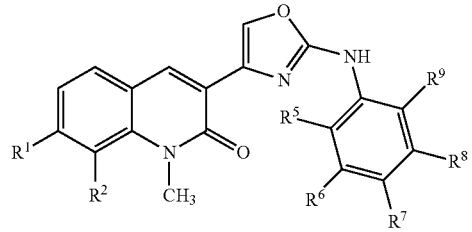

In Structure I-C, $R^1$ and $R^2$ are as defined above for Formula I.

Also in Structure I-C, $R^5$, $R^6$, $R^7$, $R^8$, and $R^9$ are as defined above for Structure I-A.

In some examples, Formula I is represented by Structure I-D:

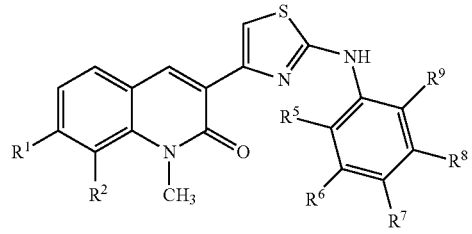

In Structure I-D, $R^1$ and $R^2$ are as defined above for Formula I.

Also in Structure I-D, $R^5$, $R^6$, $R^7$, $R^8$, and $R^9$ are as defined above for Structure I-A.

Optionally, adjacent R groups in Structures I-A, I-B, I-C, and I-D, e.g., $R^1$ and $R^2$, $R^5$ and $R^6$, $R^6$ and $R^7$, $R^7$ and $R^8$, or $R^8$ and $R^9$ can be combined to form a substituted or unsubstituted aryl, substituted or unsubstituted cycloalkenyl, substituted or unsubstituted heteroaryl, or substituted or unsubstituted heterocycloalkyl.

Examples of Formula I include the following compounds:
43H11 (DBM 101) (001_2)
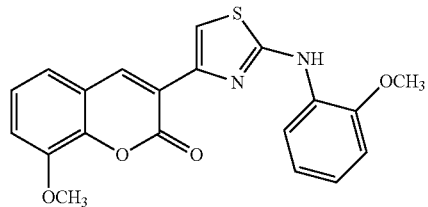
001_5
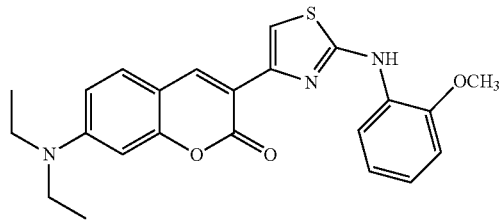
001_6
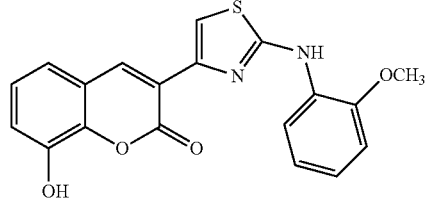
001_7
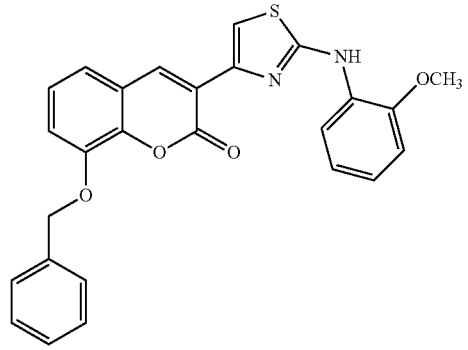
002_N7_11
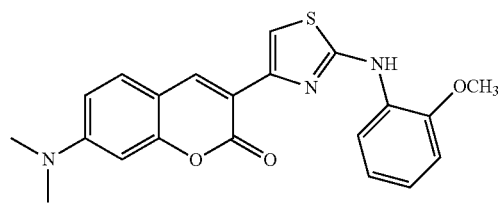
002_N7_13
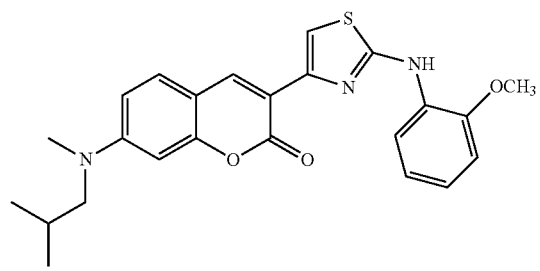
002_N7_14
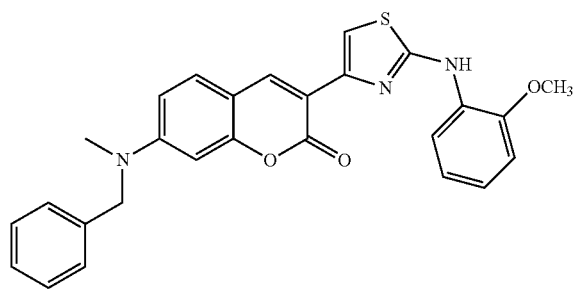
002_N7_21
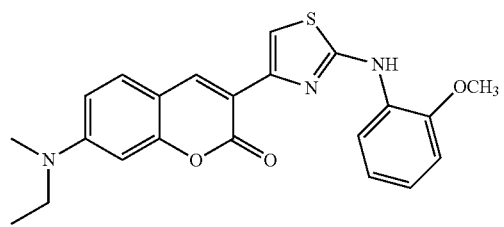
002_N7_22
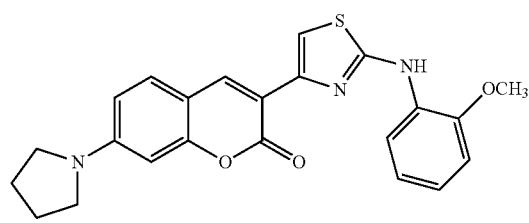
002_N7_23
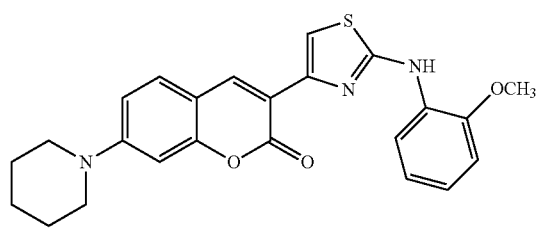

-continued
002_N7_26
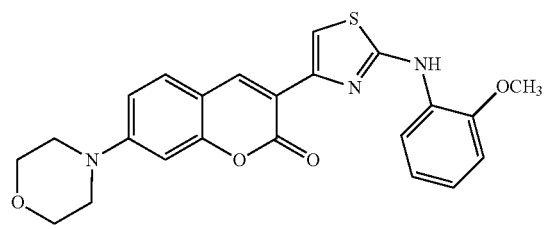
002_N7_29
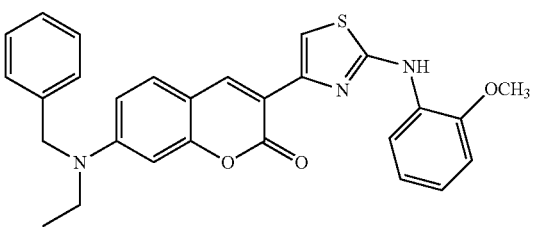
002_N7_31
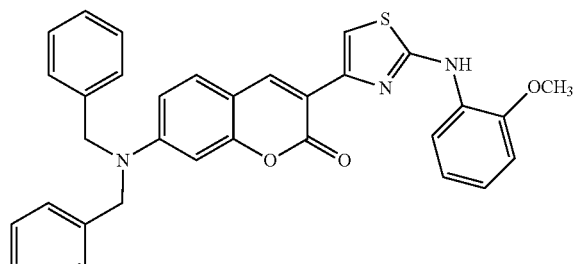
002_N8_27 (DBM227)
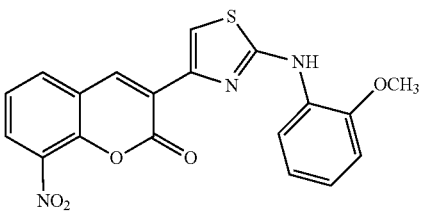
002_N8_28 (DBM228)
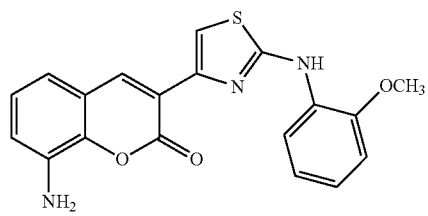
002_07_1
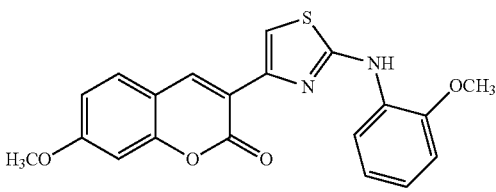
002_07_11
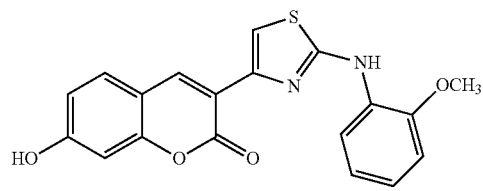
002_07_12
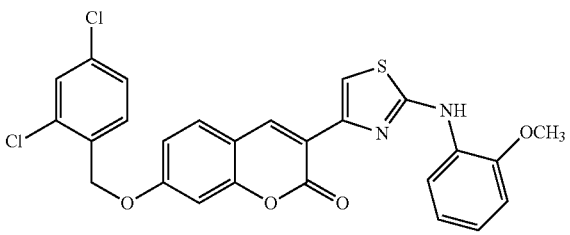
002_07_13
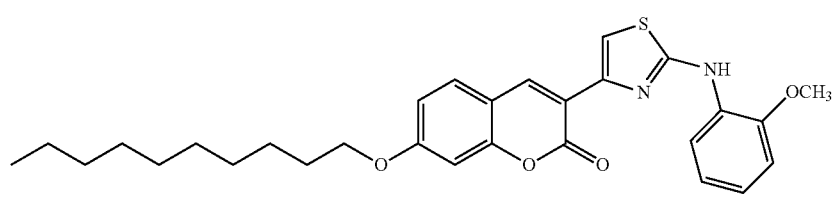
002_07_14
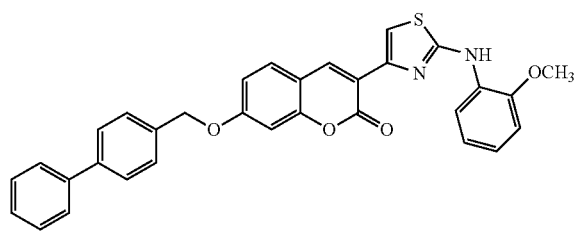
002_07_15
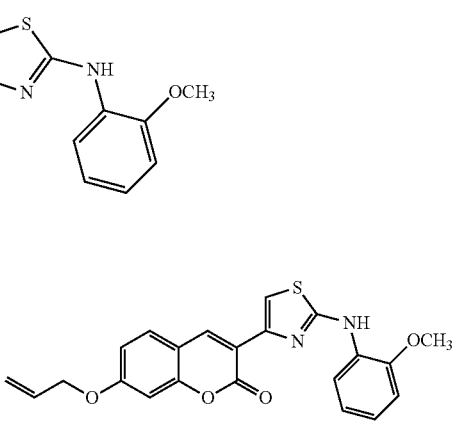

002_07_17
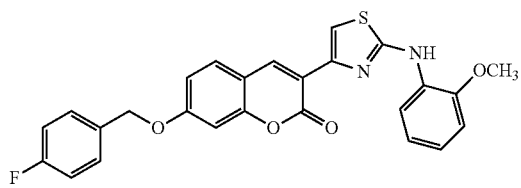
002_07_19
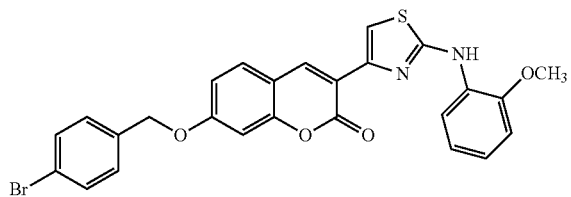
002_07_20
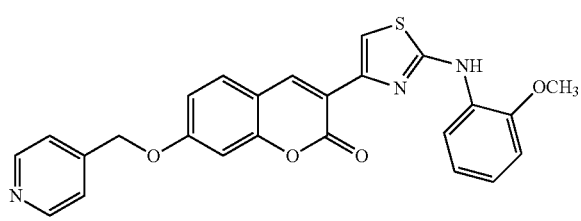
002_07_4
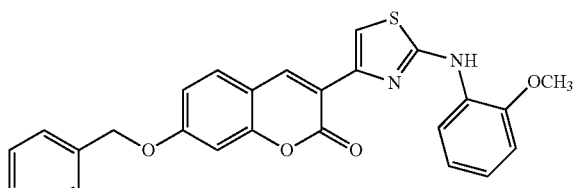
002_07_7
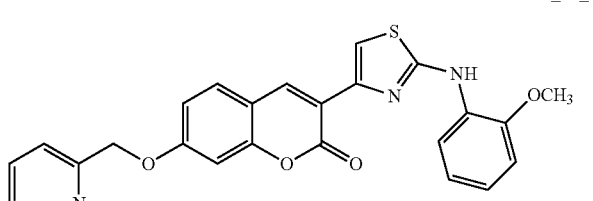
002_08_10
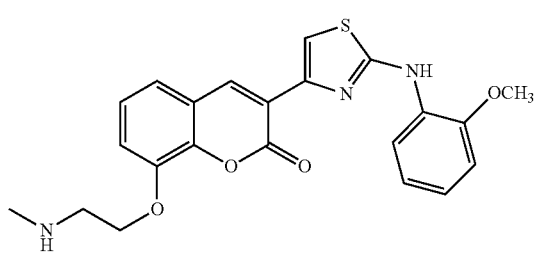
002_07_18
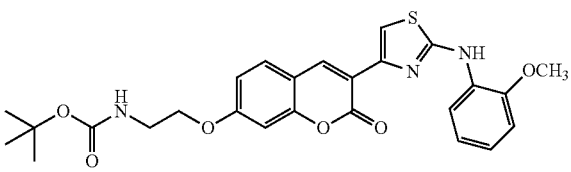
002_07_2
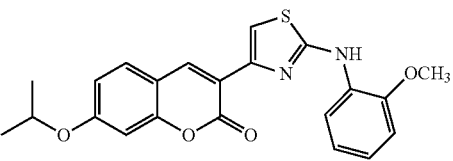
002_07_3
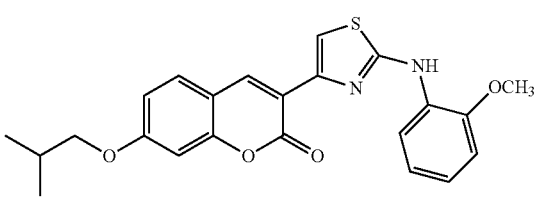
002_07_6
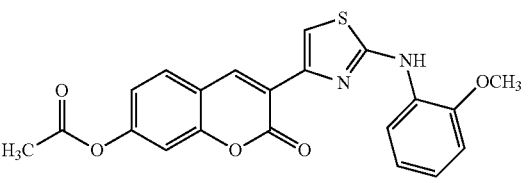
002_07_8
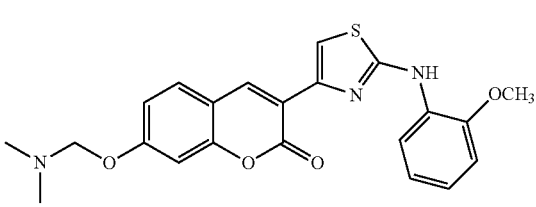
002_08_12
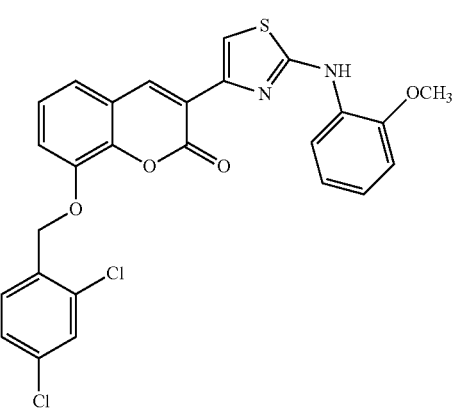

-continued
002_08_13
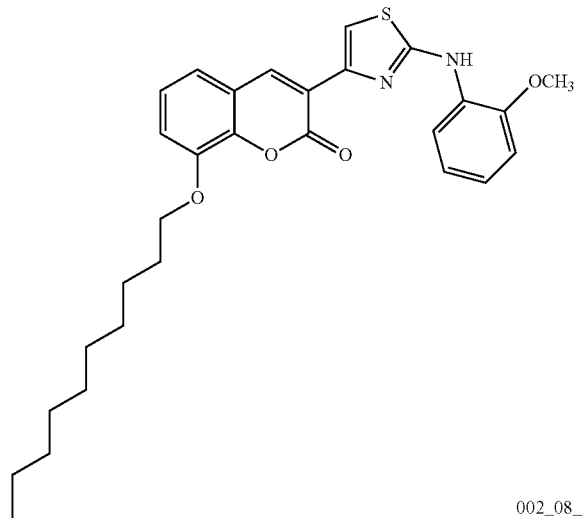
002_08_14
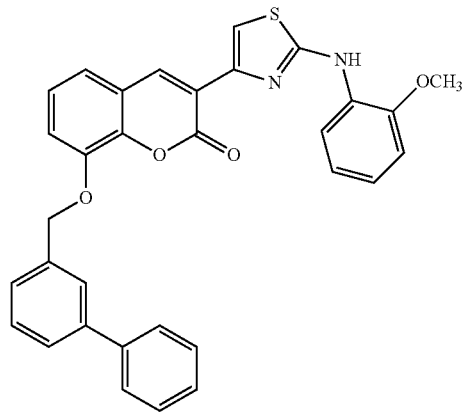
002_08_15
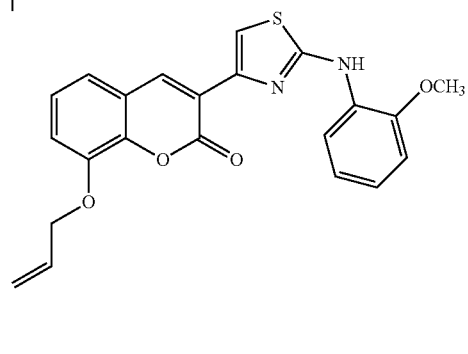
002_08_16
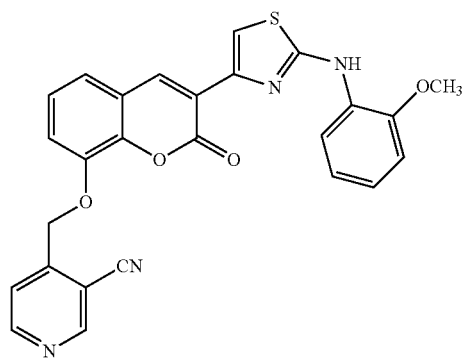
002_08_17
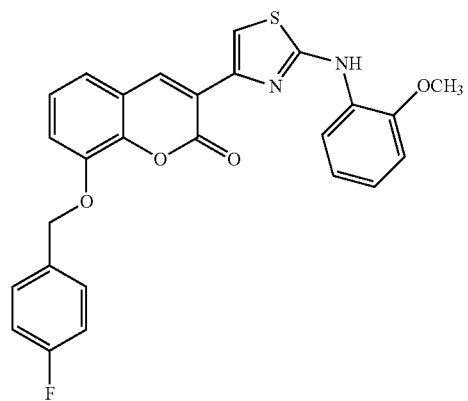
002_08_2
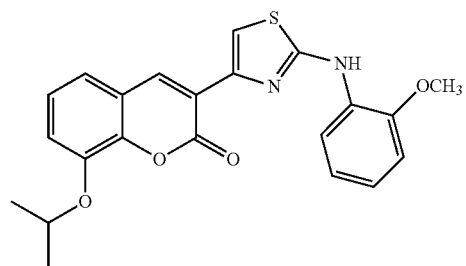
002_08_20
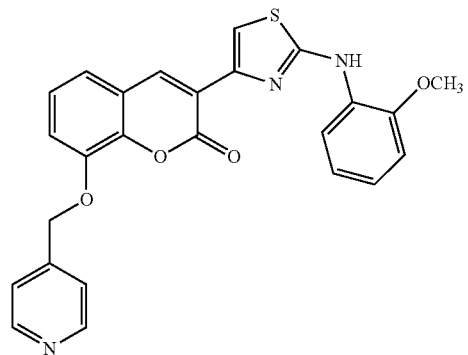
002_08_21
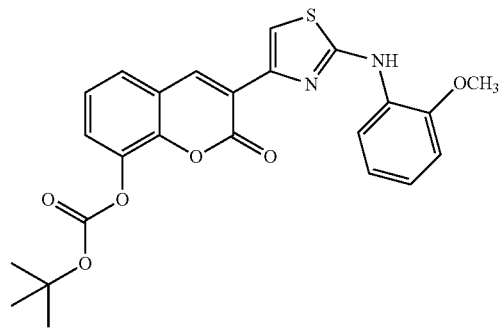

-continued
002_08_3
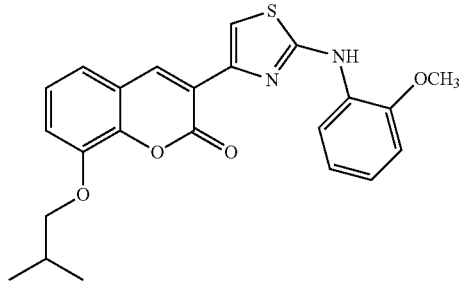
002_08_6
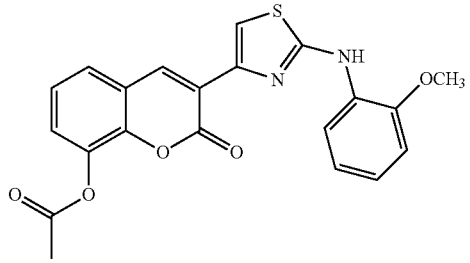
002_08_7
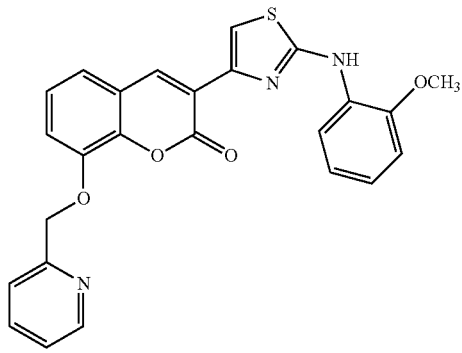
002_08_8
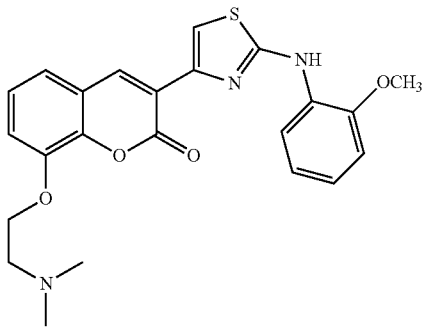
DBM-003-8F
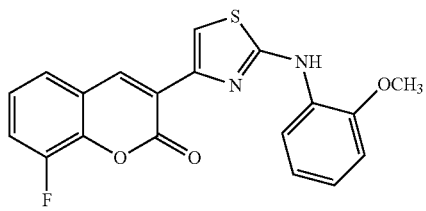
DBM-003-8Cl (DBM 308)
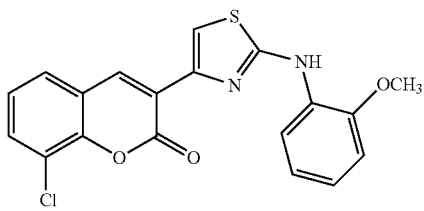
DBM-003-8Br (DBM 318)
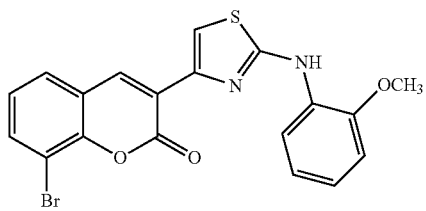
DBM-003-8I
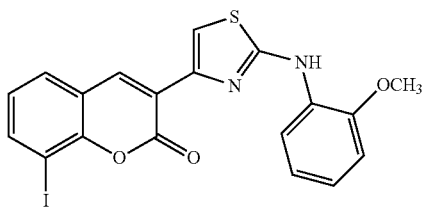
DBM-003-8COOH (DBM 328)
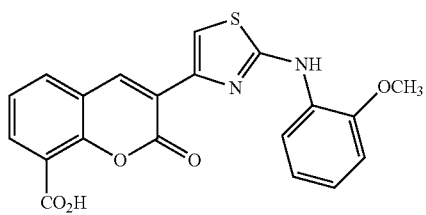
DBM-003-8CN
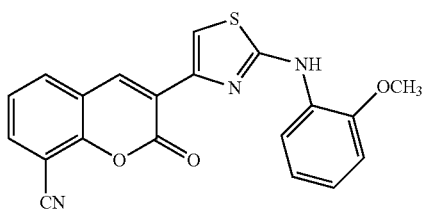
DBM-003-8COOCH3
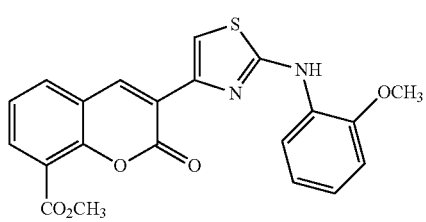
DBM-003-TU4
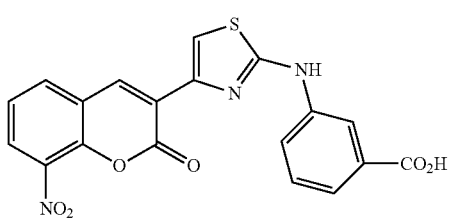

-continued
DBM-003-TU31
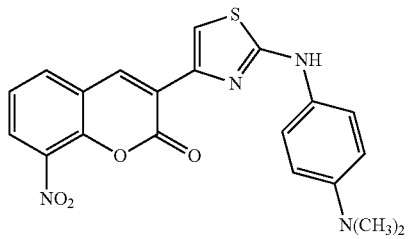
DBM-003-TU16
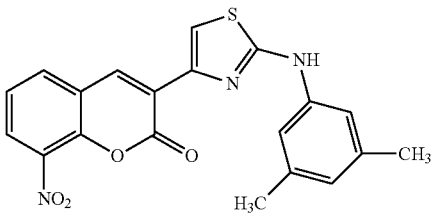
DBM-003-TU21
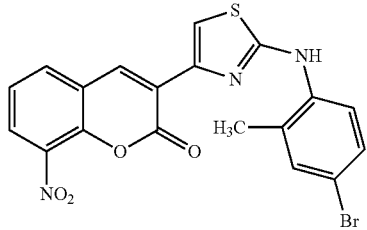
DBM-003-TU21-F
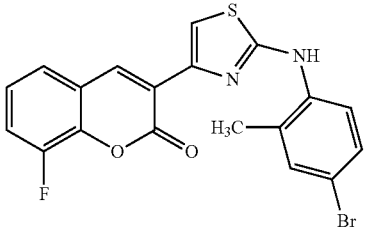
DBM-003-TU4-F
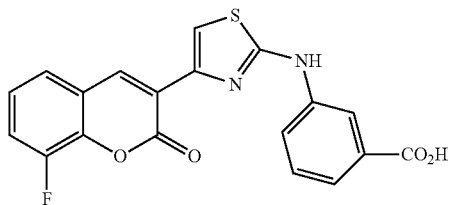
DBM-003-TU16-F
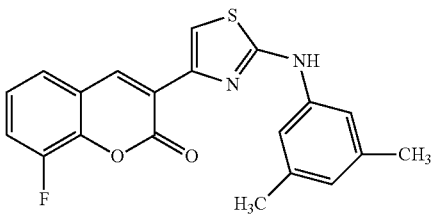
DBM-003-TU16-Cl
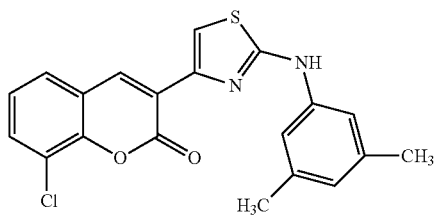
DBM-003-TU16-Br
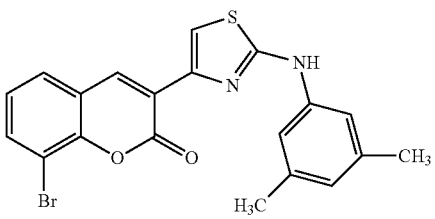
DBM-003-TU21-Br
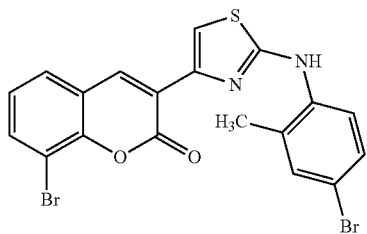
DBM-003-TU4-Br
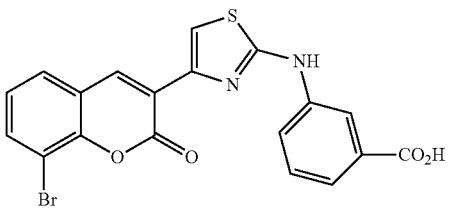
DBM-003-TU21-COOCH3
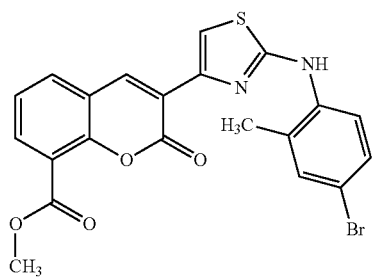
DBM-003-TU16-COOCH3
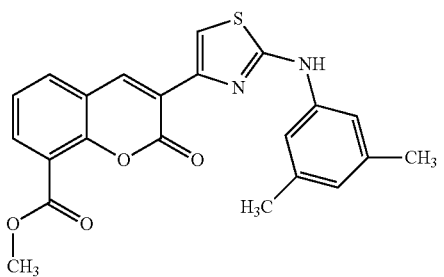

-continued
| 007-01 (DBM-701) | 007-02 |
|---|---|
| 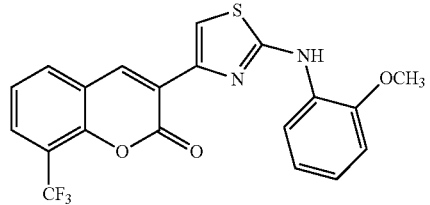 | 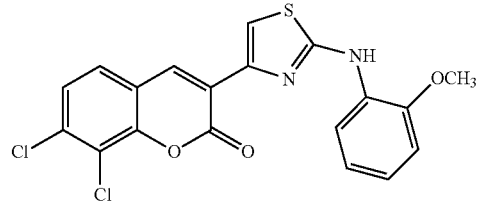 |
| 007-03 | 007-04 |
|  | 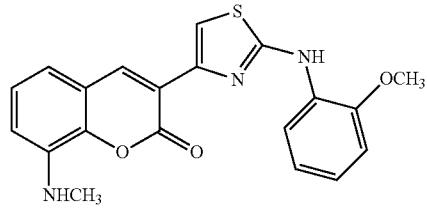 |
| 007-05 | 004-06 |
| 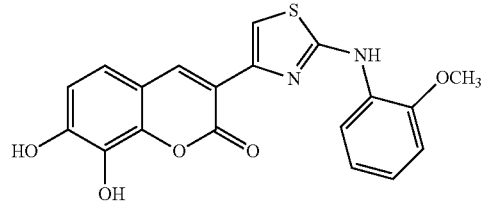 | 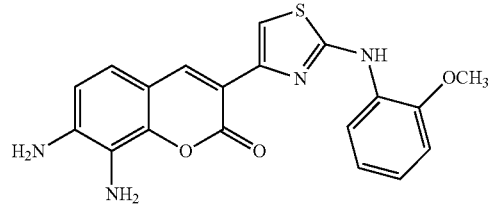 |
| 004-07 (DBM 707) | 004-09 |
| 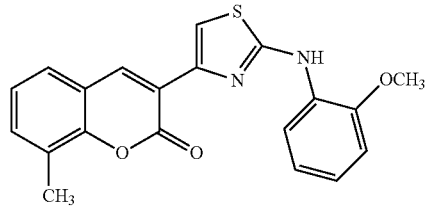 | 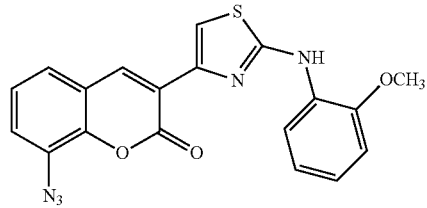 |
| 004-10 | 004-14 |
| 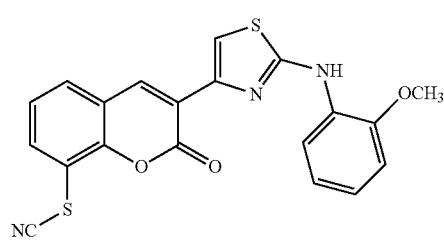 | 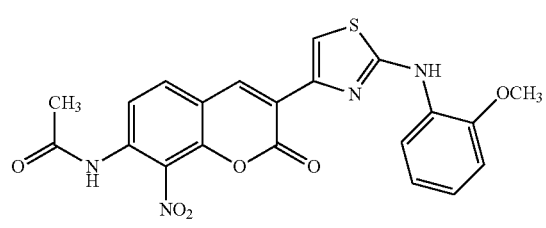 |
| 004-15 (DBM 715) | DBM-E-01 |
| 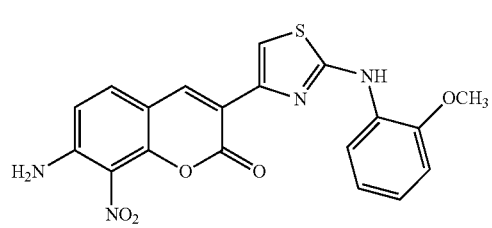 | 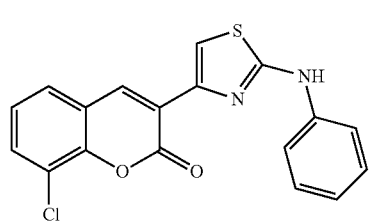 |
| DBM-E-02 | DBM-E-03 |
| 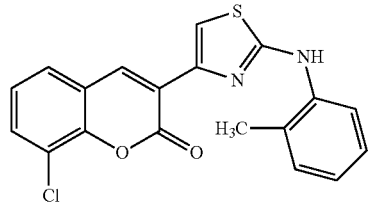 | 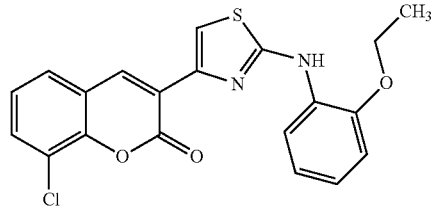 |

-continued
DBM-E-04
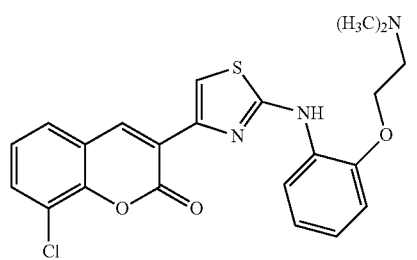
DBM-E-05
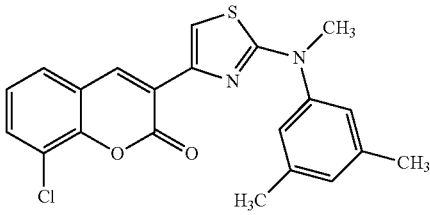
DBM-E-05.1
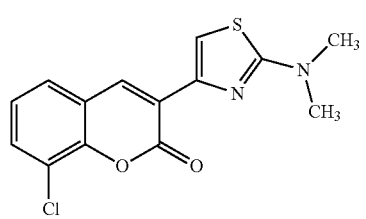
DBM-E-06
DBM-E-07
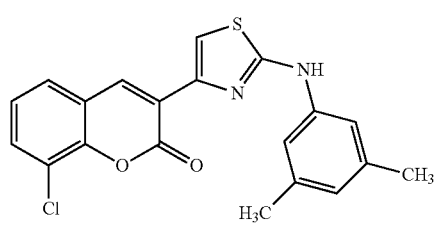
DBM-E-11
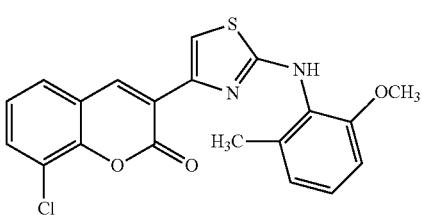
DBM-E-12
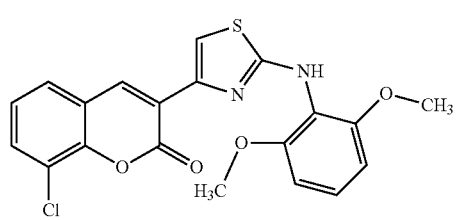
DBM-E-13
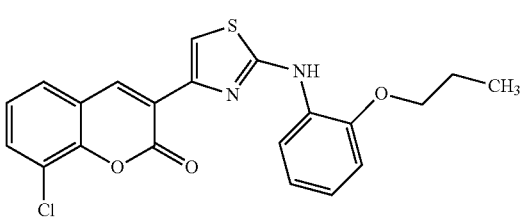
DBM-E-14
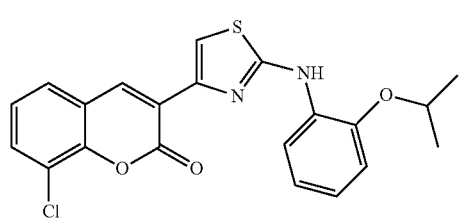
DBM-E-15
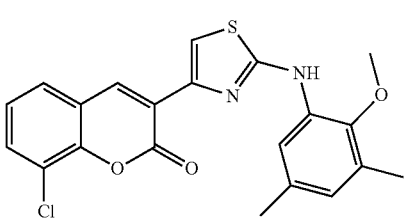
DBM-E-16
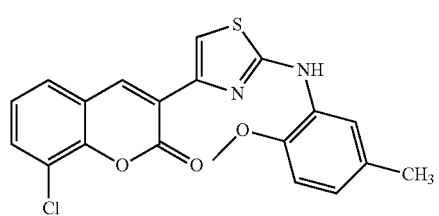
DBM-E-17
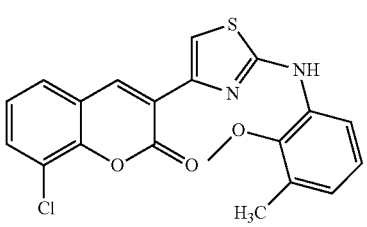

-continued
DBM-E-18
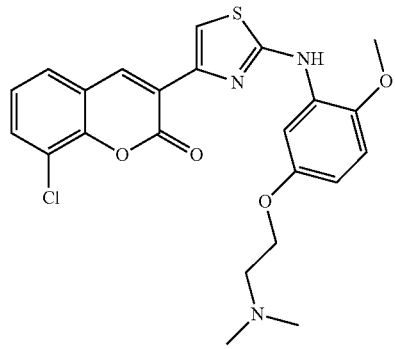
DBM-E-19
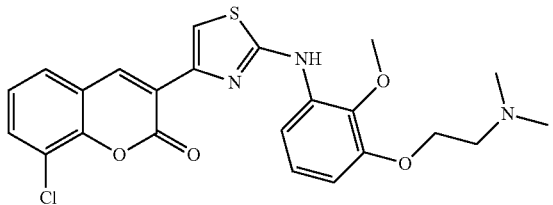
DBM-E-20
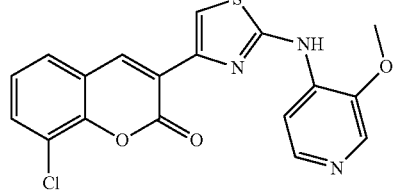
DBM-E-21
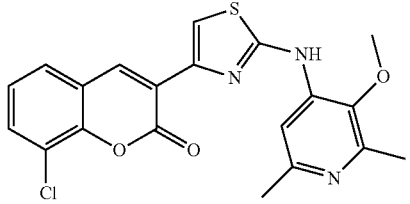
DBM-E-22
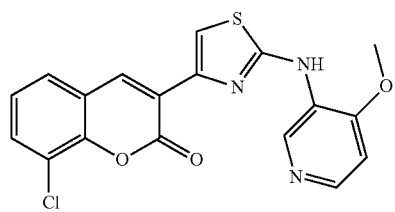
DBM-E-23
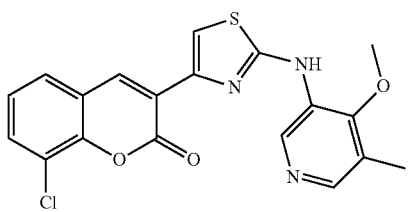
P1
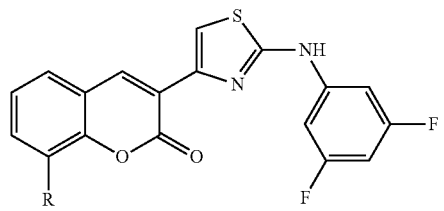
P2
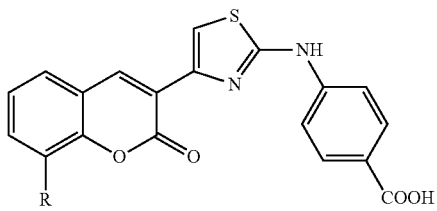
P3
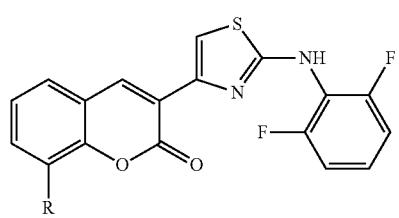
P4
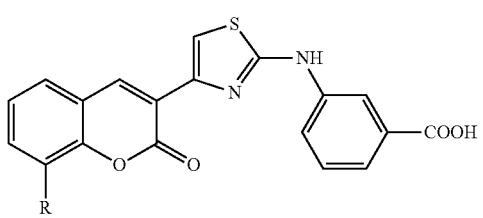
P5
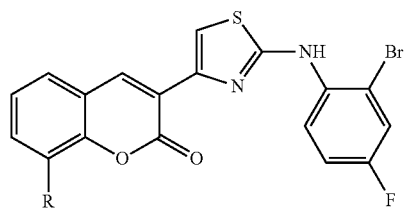
P6
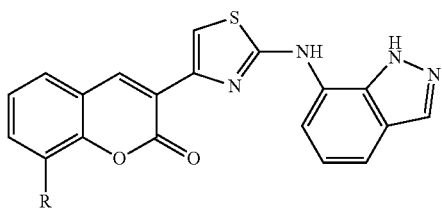

-continued
P7
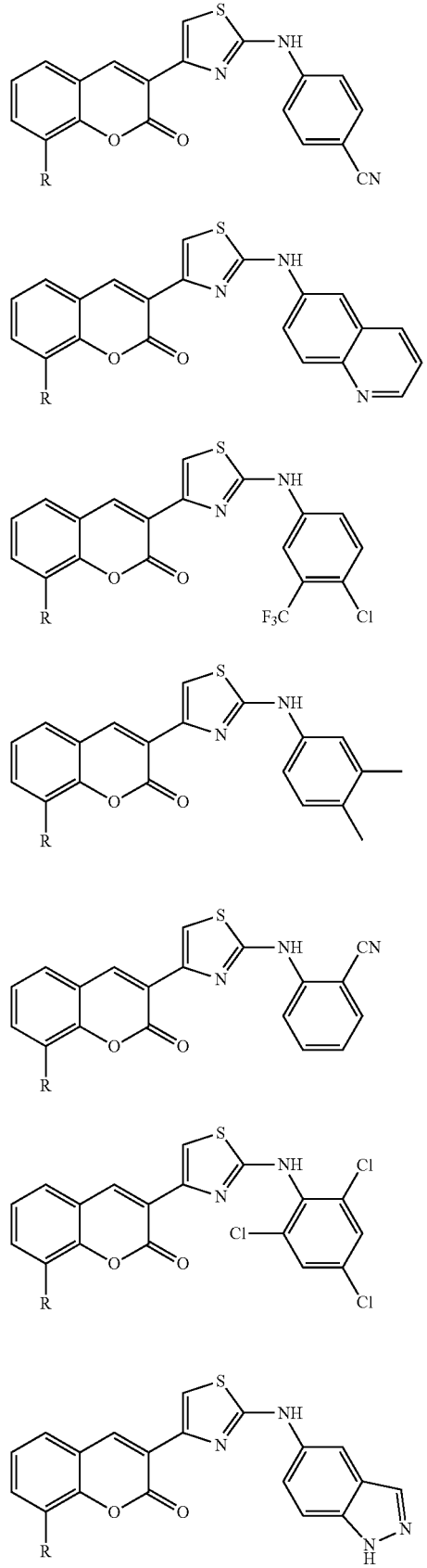
P8
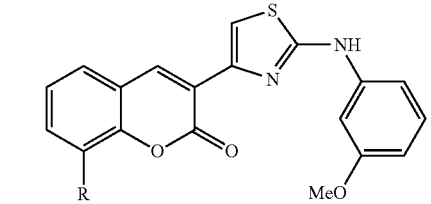
P9
P10
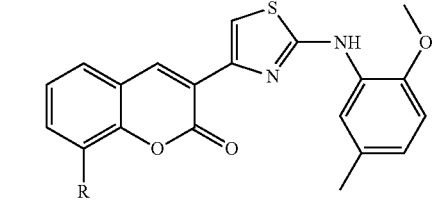
P11
P12
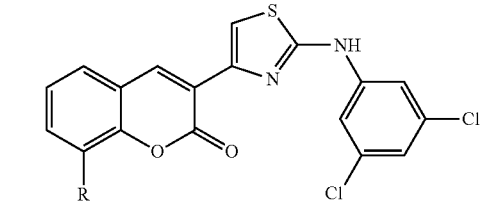
P13
P14
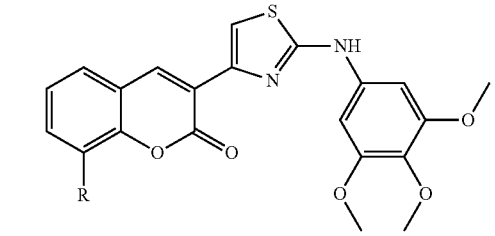
P15
P16
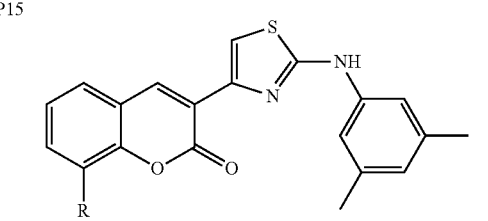
P17
P18
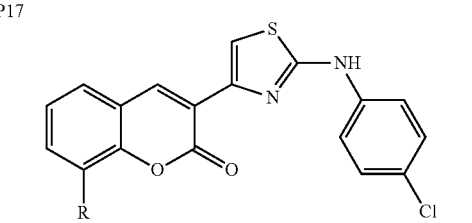
P19
P20
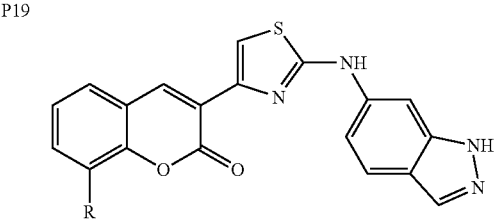

-continued
P21
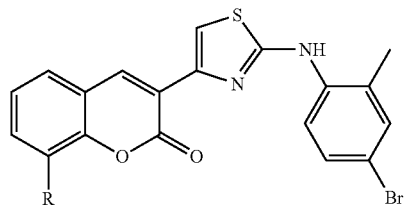
P22
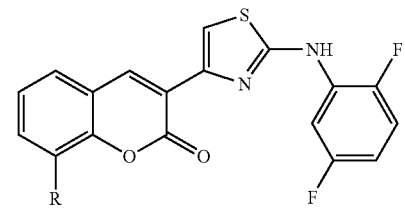
P23
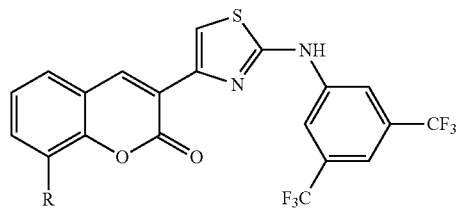
P24
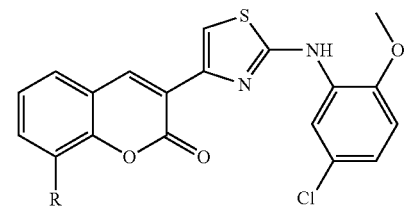
P25
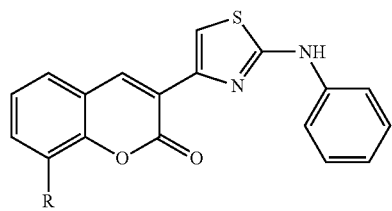
P26
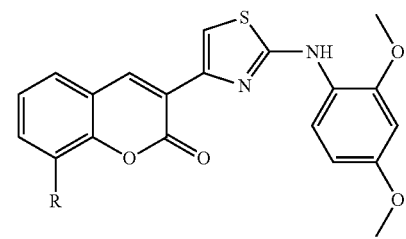
P27
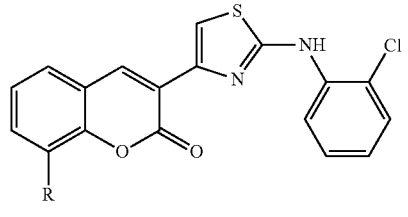
P28
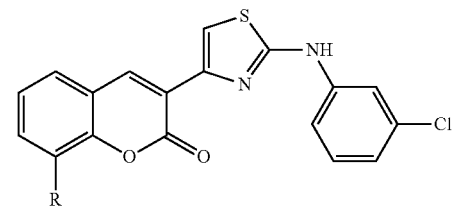
P29
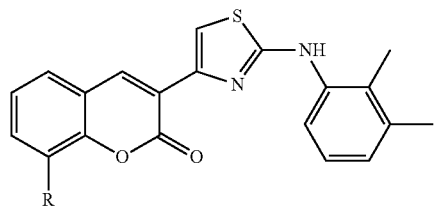
P30
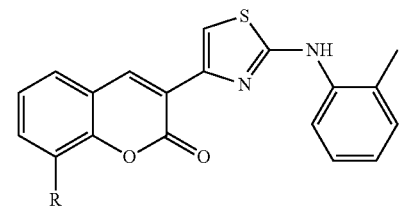
P31
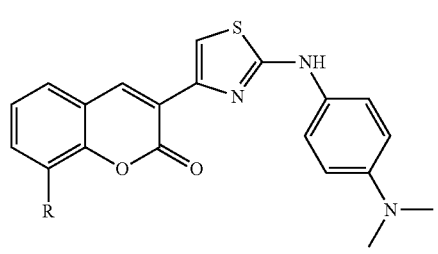
P32
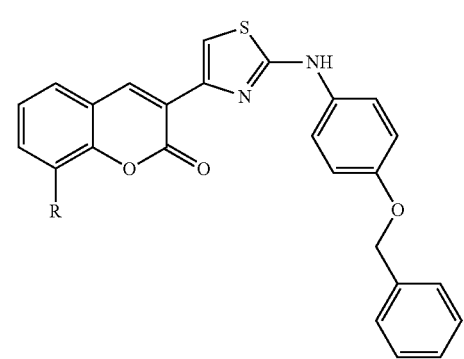

P33 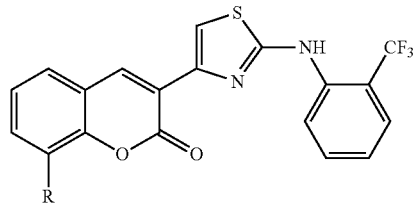
P34 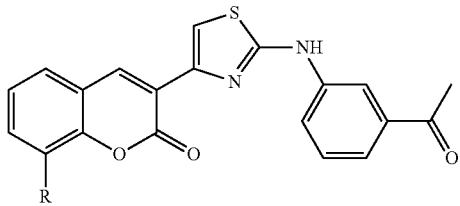
P35 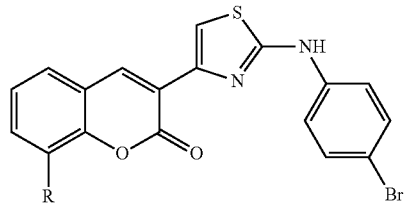
P36 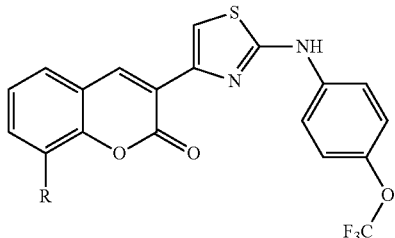
P37 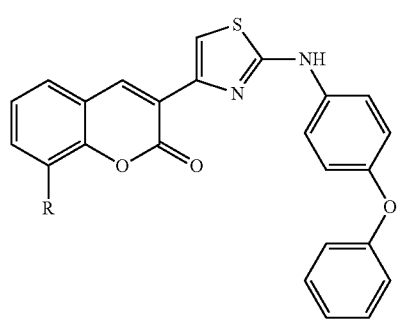
P38 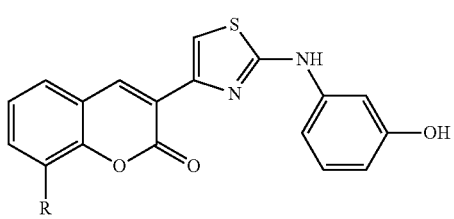
P39 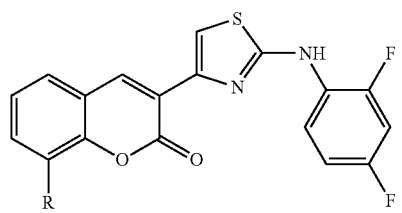
P40 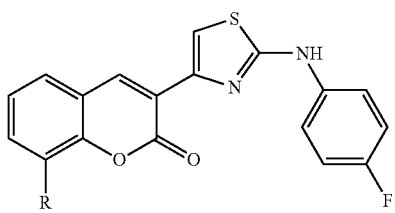
P41 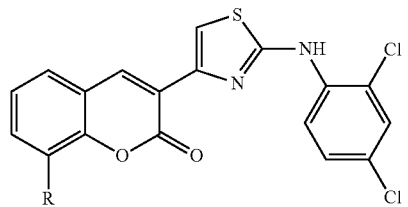
P42 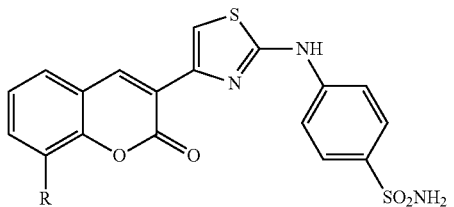
P43 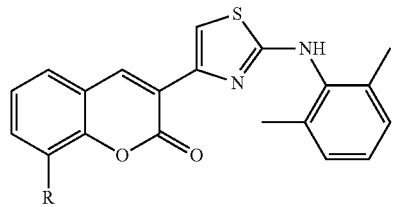
P44 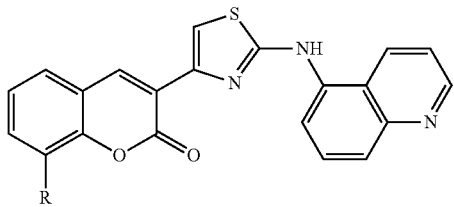
P45 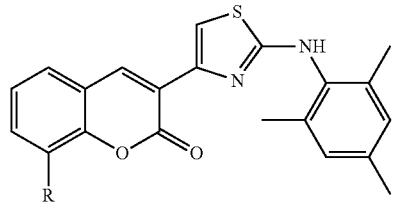
P46 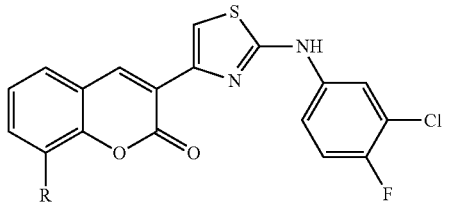

-continued
P47
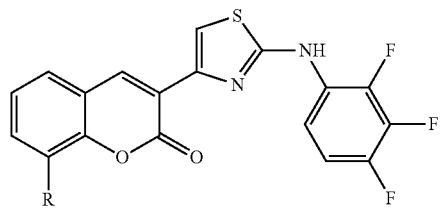
P48
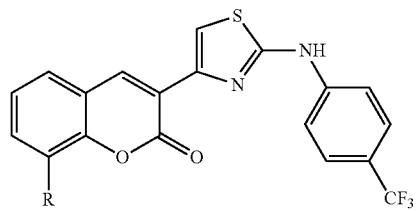
P49
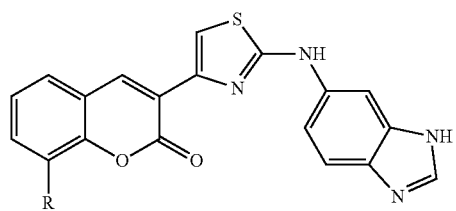
P50
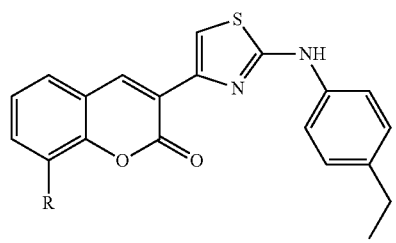
P51
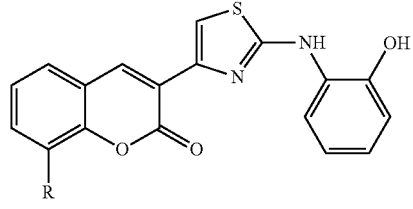
P52
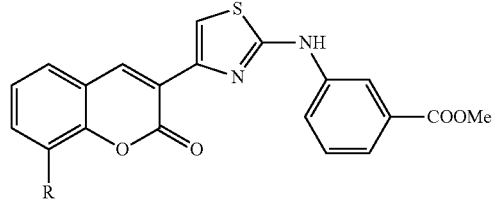
P53
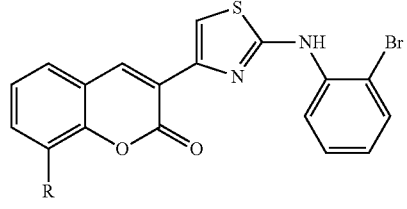
P54
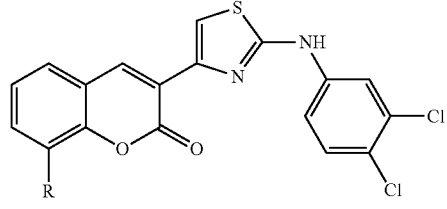
P55
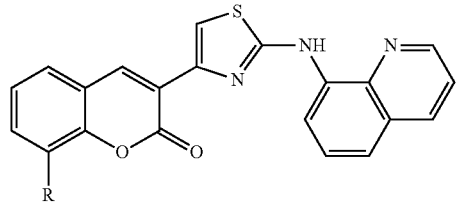
P56
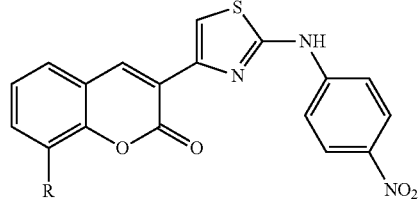
P57
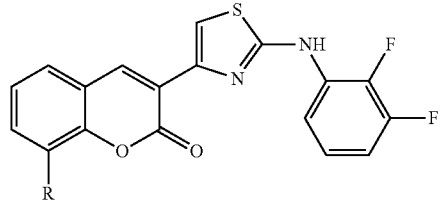
P58
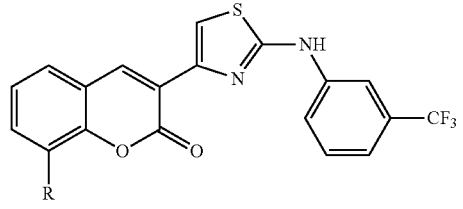
P59
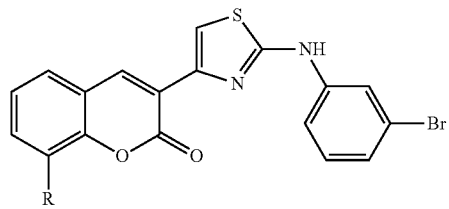
P60
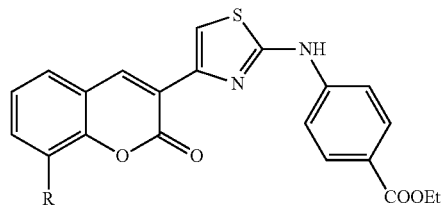

-continued
P61 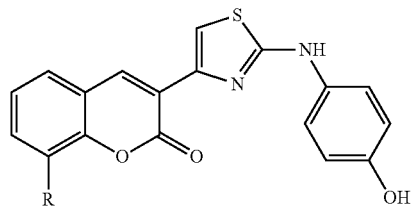 P62 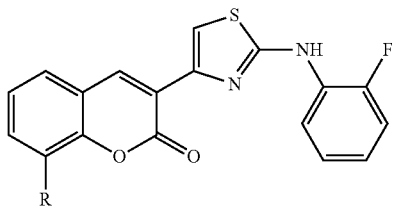
P63 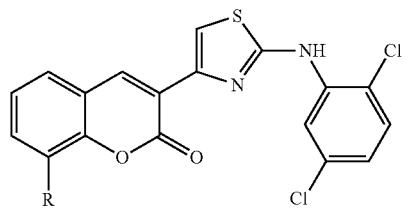 P64 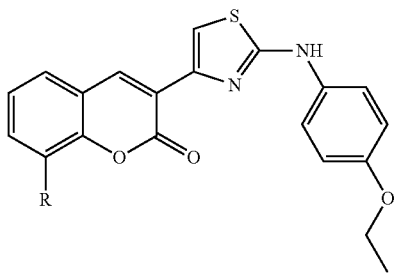
P65 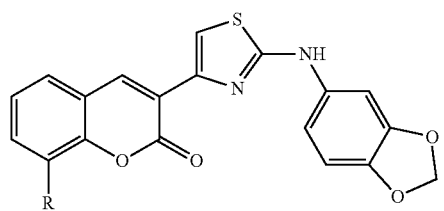 P66 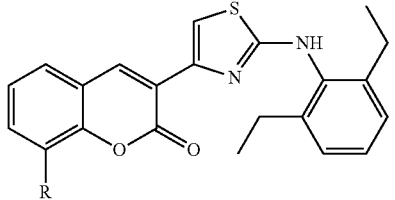
P67 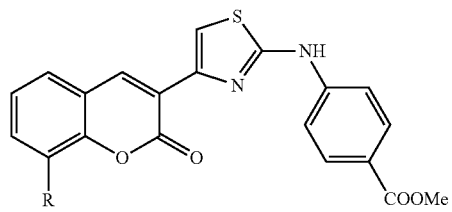 P68 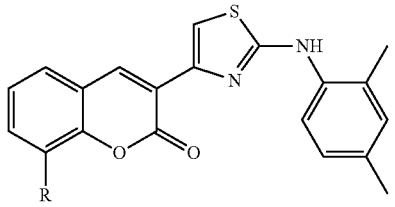
P69 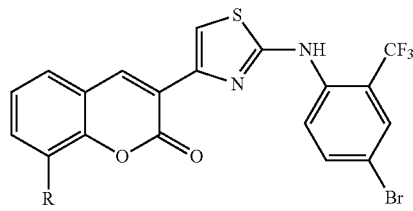 P70 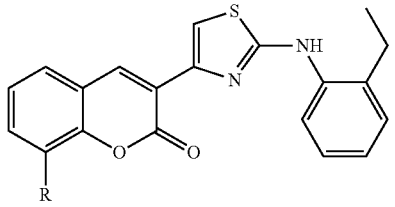
P71 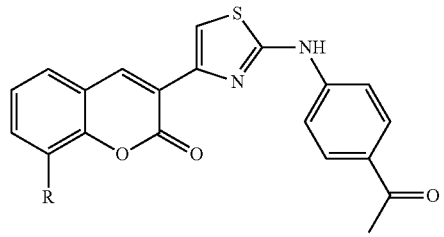 P72 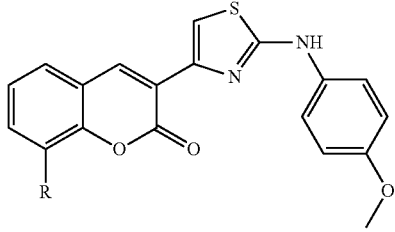
P73 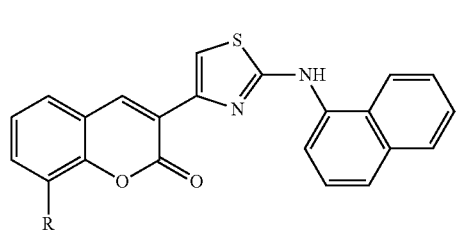 P74 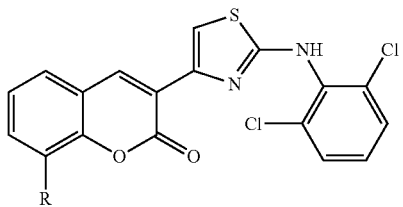

P75
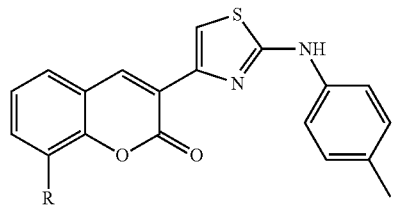
P76
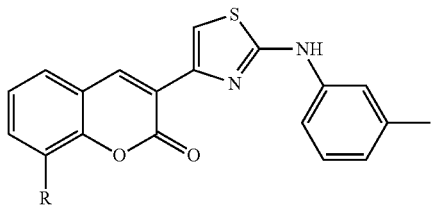
P77
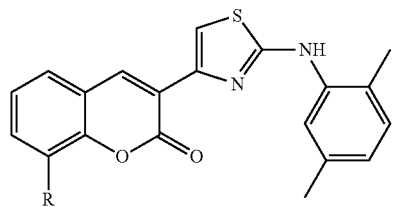
P78
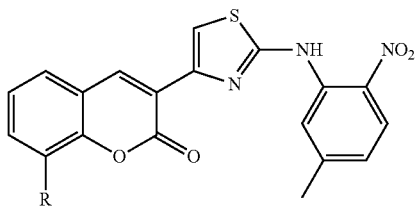
P79
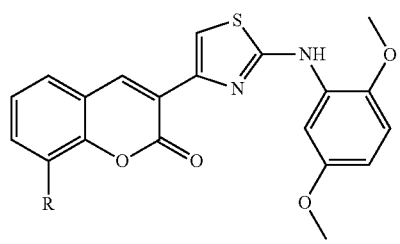
P80
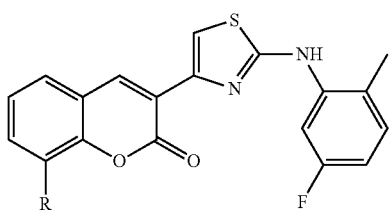
P81
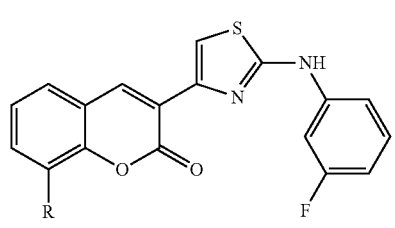
P82
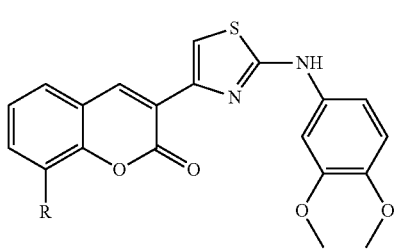
P83
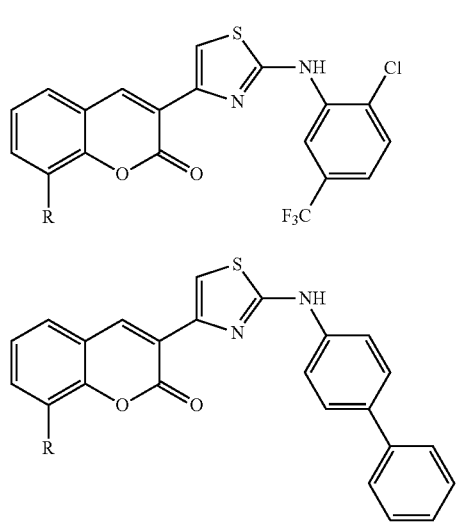
P84
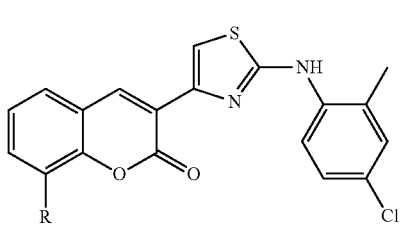
P85
P86
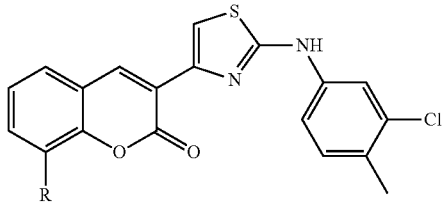
P87
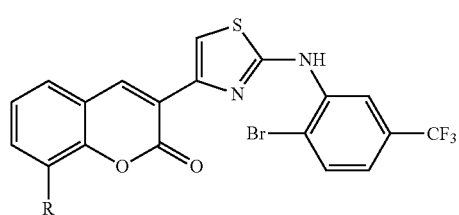
P88
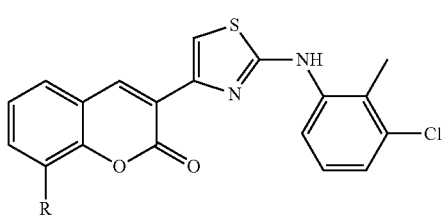

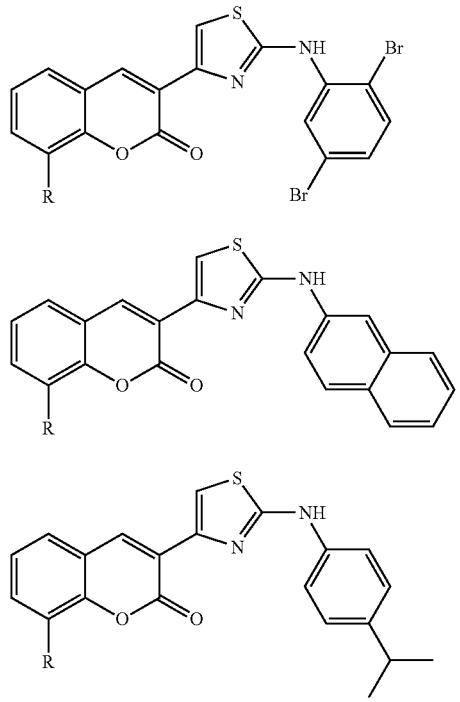
P89
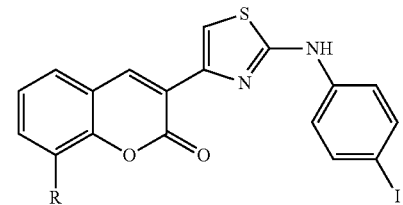
P90
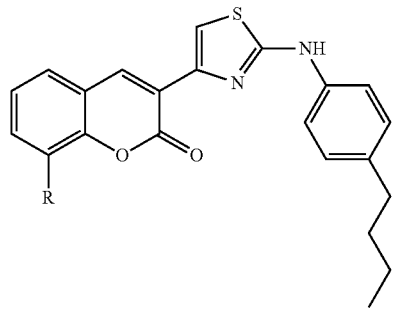
P91
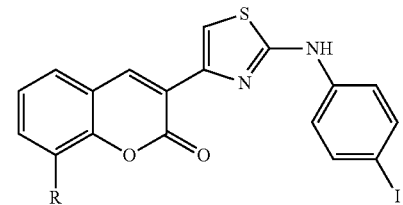
P92
P93
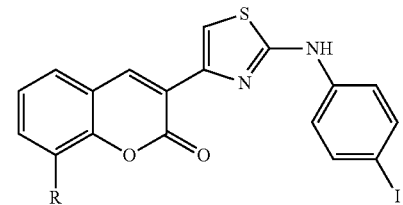
P94
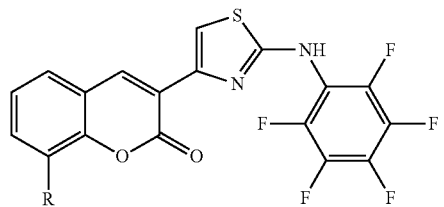
P95
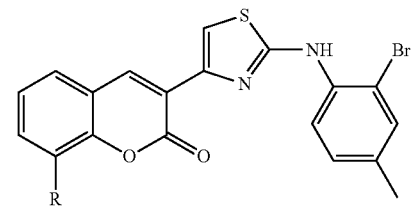
P96
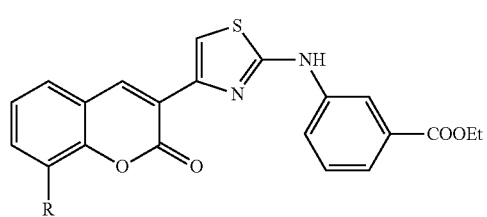
P97
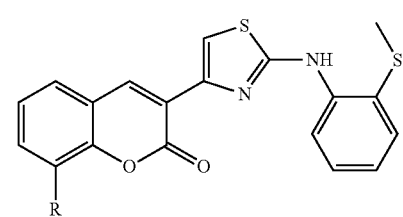
P98
P99
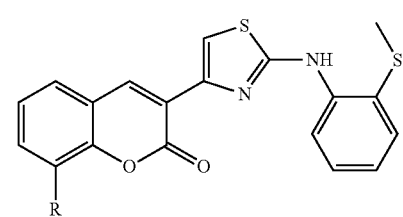
P100

-continued

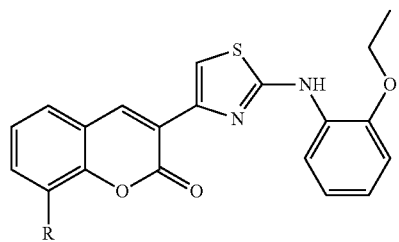
P101

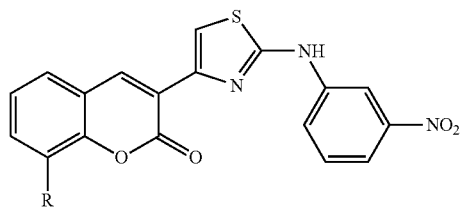
P102

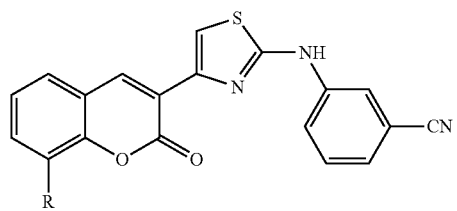
P103

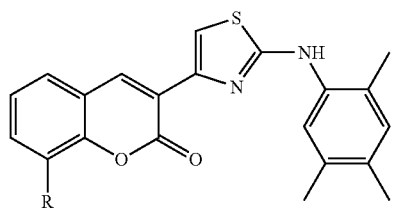
P104

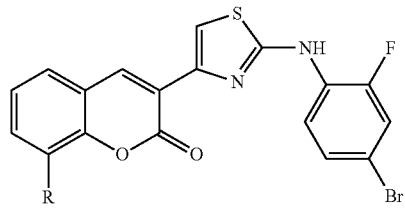
P105

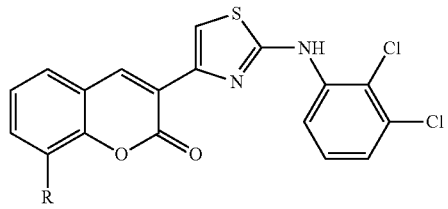
P106

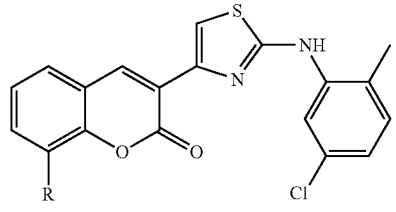
P107

In Compounds P1 through P107, R can be halogen (e.g., chloro). In some embodiments, the compound is not Compound DBM 328.

A class of coumarin derivatives described herein is represented by Formula II:

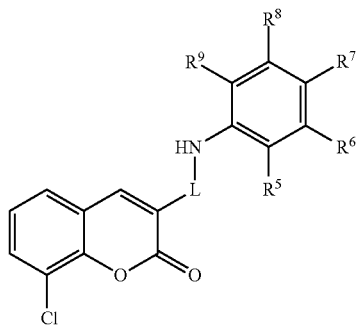
II and pharmaceutically acceptable salts or prodrugs thereof.

In Formula II, L is a heteroaryl.

Also, in Formula II, $R^5$, $R^6$, $R^7$, $R^8$, and $R^9$ are each independently selected from hydrogen and methoxy.

In some examples, Formula II is represented by Structure II-A:

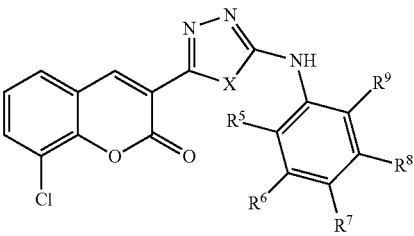

In Structure II-A, X is NH or O.

Also in Structure II-A, $R^5$, $R^6$, $R^7$, $R^8$, and $R^9$ are as defined above for Formula II.

In some examples, Formula II is represented by Structure II-B:

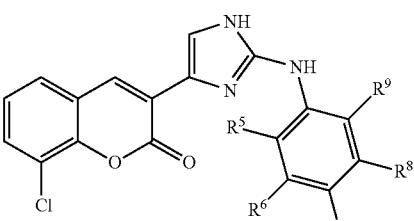

In Structure II-B, $R^5$, $R^6$, $R^7$, $R^8$, and $R^9$ are as defined above for Formula II.

In some examples, Formula II is represented by Structure II-C:

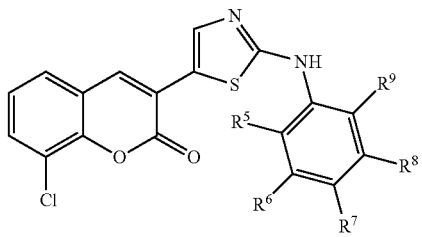

In Structure II-C, $R^5$, $R^6$, $R^7$, $R^8$, and $R^9$ are as defined above for Formula II.

Examples of Formula II include the following compounds:

Compound II-1

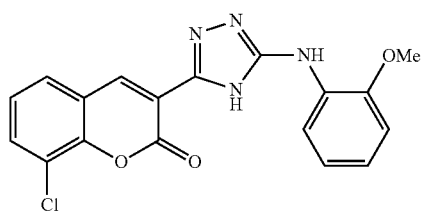

Compound II-2

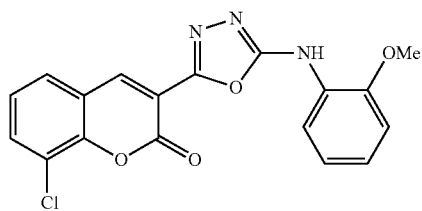

Compound II-3

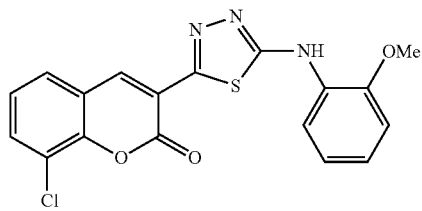

Compound II-4

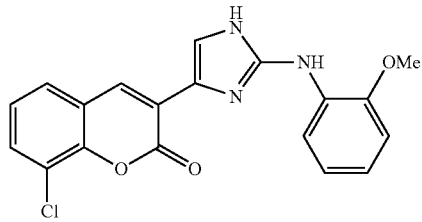

DBM-E-10

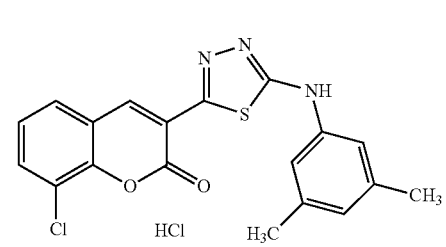

A class of coumarin derivatives described herein is represented by Formula III:

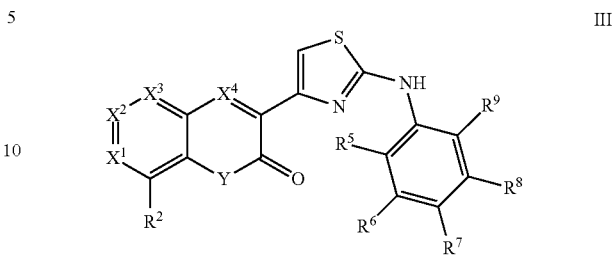

III and pharmaceutically acceptable salts or prodrugs thereof.

In Formula III, $X^1$, $X^2$, $X^3$ and $X^4$ are each independently selected from CH and N.

Also, in Formula III, Y is O or NR, where R is hydrogen or methyl.

Additionally, in Formula III, $R^2$ is hydrogen, $C_{1-6}$ alkyl, halogen, or trifluoroalkyl. Optionally, $R^2$ is Cl or methyl.

Further, in Formula III, $R^5$, $R^6$, $R^7$, $R^8$, and $R^9$ are each independently selected from hydrogen and methoxy.

In some examples, Formula III is represented by Structure III-A:

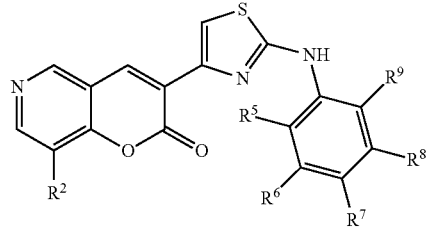

In Structure III-A, $R^2$, $R^5$, $R^6$, $R^7$, $R^8$, and $R^9$ are as defined above for Formula III.

In some examples, Formula III is represented by Structure III-B:

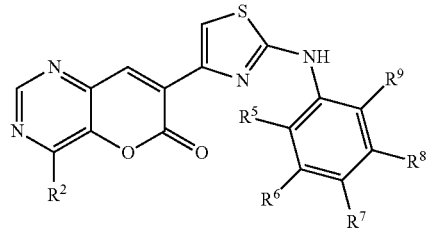

In Structure III-B, $R^2$, $R^5$, $R^6$, $R^7$, $R^8$, and $R^9$ are as defined above for Formula III.

In some examples, Formula III is represented by Structure III-C:

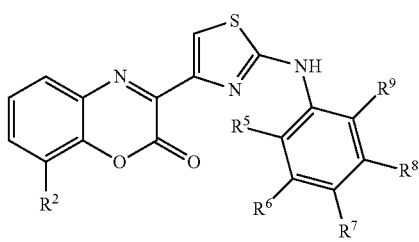

In Structure III-C, $R^2$, $R^5$, $R^6$, $R^7$, $R^8$, and $R^9$ are as defined above for Formula III.

In some examples, Formula III is represented by Structure III-D:

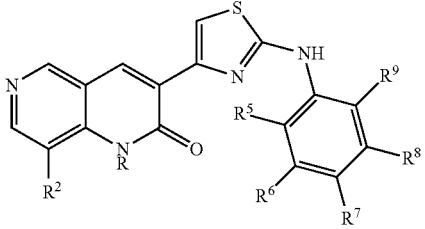

In Structure III-D, R is hydrogen or methyl.

Also, in Structure III-D, $R^2$, $R^5$, $R^6$, $R^7$, $R^8$, and $R^9$ are as defined above for Formula III.

Examples of Formula III include the following compounds:

Compound III-1

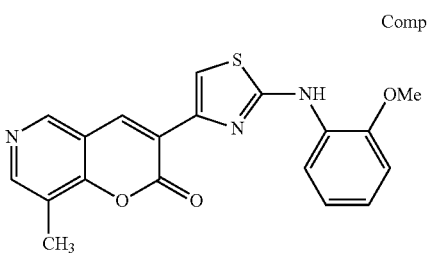

Compound III-2

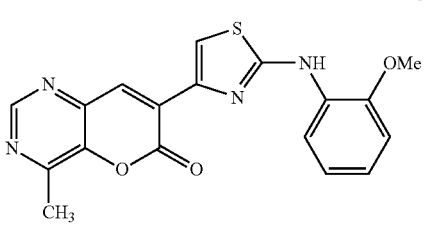

Compound III-3

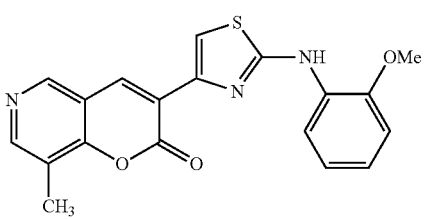

Compound III-4

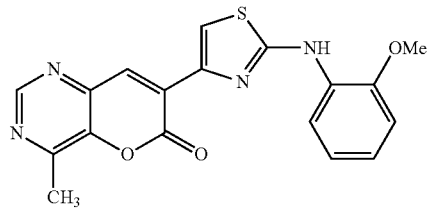

A class of coumarin derivatives described herein is represented by Formula IV:

IV

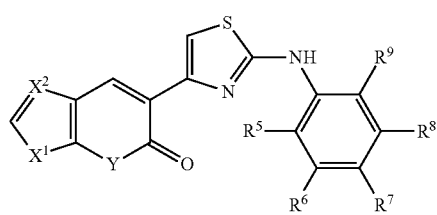

and pharmaceutically acceptable salts or prodrugs thereof.

In Formula IV, $X^1$ is O or $NCH_3$.

Also, in Formula IV, $X^2$ is CH or N.

Additionally, in Formula IV, Y is O, NH, or $NCH_3$.

Further, in Formula IV, $R^5$, $R^6$, $R^7$, $R^8$, and $R^9$ are each independently selected from hydrogen and methoxy.

Examples of Formula IV include the following compounds:

Compound IV-1

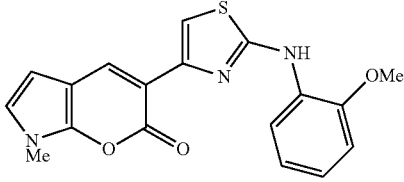

Compound IV-2

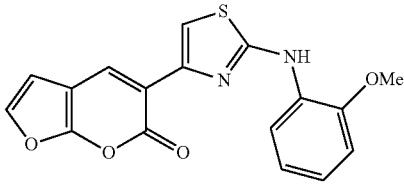

Compound IV-3

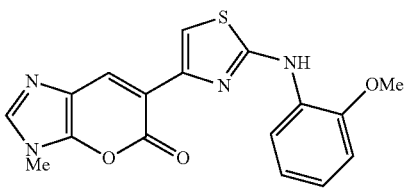

Compound IV-4
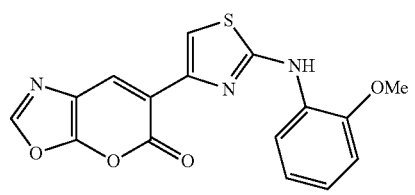

Compound IV-5
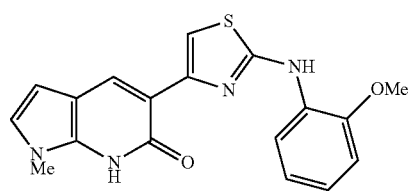

Compound IV-6
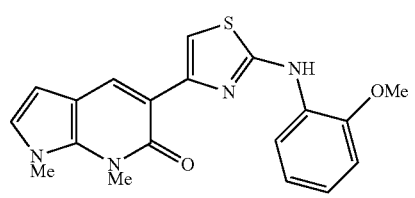

Compound IV-7
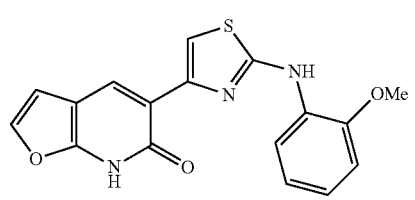

Compound IV-8
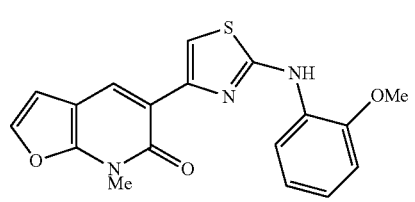

A class of coumarin derivatives described herein is represented by Formula V:

V
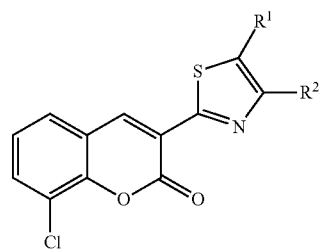

and pharmaceutically acceptable salts or prodrugs thereof.

In Formula V, $R^1$ and $R^2$ are each independently selected from hydrogen, substituted or unsubstituted amino, and substituted or unsubstituted carbonyl.

Examples of Formula V include the following compounds:

DBM-E-08
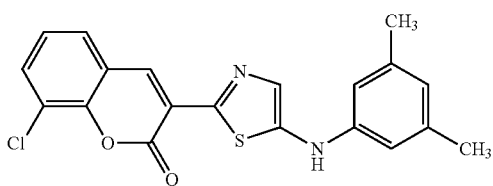

DBM-E-09
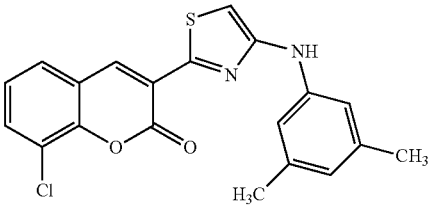

DBM-E-09.1
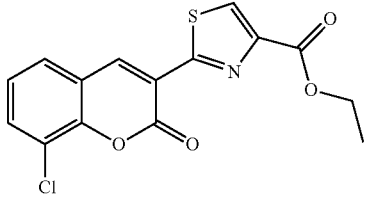

A class of coumarin derivatives described herein is represented by Formula VI:

VI
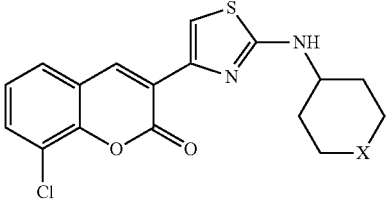

and pharmaceutically acceptable salts or prodrugs thereof.

In Formula VI, X is $CH_2$, NH, or O.

Examples of Formula VI include the following compounds:

Compound VI-1
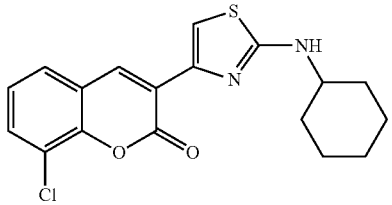

Compound VI-2
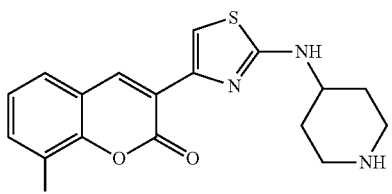

Compound VI-3

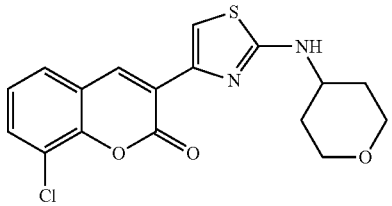

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formulas I-VI include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

III. Pharmaceutical Formulations

The compounds described herein or derivatives thereof can be provided in a pharmaceutical composition. The pharmaceutical compositions are administered in a number of ways depending on whether local or systemic treatment is desired, and on the area to be treated. The pharmaceutical compositions are administered via any of several routes of administration, including topically, orally, parenterally, intravenously, intra-articularly, intraperitoneally, intramuscularly, subcutaneously, intradermally, intracavity (e.g., rectal, intravesical, lumen of vesical organs), transdermally, intrahepatically, intracranially, nebulization/inhalation, or by installation via bronchoscopy. Intradermal administration includes administration at a site that is afferent to the site of lymphatic transport dysfunction. Optionally, the pharmaceutical composition is administered by oral inhalation, nasal inhalation, intranasal mucosal administration, or suppository. The pharmaceutical composition can also be injected or infused, for example, at a site of inflammation, such as, for example, an inflamed joint. Administration of the pharmaceutical compositions by inhalant can be through the nose or mouth via delivery by spraying or droplet mechanism, for example, in the form of an aerosol.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., J. Pharm. Sci. (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

IV. Methods of Use

The methods described herein include a method of treating hyperproliferative diseases in a subject. These methods include the step of administering to the subject an effective amount of a compound as described herein, or a pharmaceutically salt or prodrug thereof. The expression "effective amount," when used to describe an amount of compound in a method, refers to the amount of a compound that achieves the desired pharmacological effect or other effect, for example, an amount that results in tumor growth rate reduction. Additional steps can be included in the method described herein. For example, the methods can further include the steps of selecting a subject with a hyperproliferative disease, and administering to the subject one or more of the compounds as described herein. The compounds and compositions described herein or pharmaceutically acceptable salts thereof are useful for treating hyperproliferative diseases in humans, including, without limitation, pediatric and geriatric populations, and in animals, e.g., veterinary applications. Optionally, the hyperproliferative disease is cancer. Optionally, the hyperproliferative disease is polycystic kidney disease. Optionally, the hyperproliferative disease is idiopathic pulmonary fibrosis.

As described above, the compounds described herein are useful in the treatment of hyperproliferative diseases, including cancer, polycystic kidney disease, and fibrosis. The compounds described herein do not significantly inhibit cellular proliferation in normal cell types or in non-proliferating cells.

Optionally, the cancer is bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, or testicular cancer.

Optionally, the polycystic kidney disease is autosomal dominant polycystic kidney disease (ADPKD) or autosomal cecessive polycystic kidney disease (ARPKD). The methods of treating a polycystic kidney disease in a subject can further include treating or preventing symptoms of polycystic kidney disease. The symptoms can be related to ADPKD or ARPKD. For example, the symptoms can include brain aneurysms, cysts in the liver, pancreas, and testes, urinary tract infections, high blood pressure and diverticula of the colon.

Optionally, the fibrosis is pulmonary fibrosis, idiopathic pulmonary fibrosis, cirrhosis, endomyocardial fibrosis, mediastinal fibrosis, myelofibrosis, retroperitoneal fibrosis, progressive massive fibrosis, nephrogenic systemic fibrosis, Crohn's Disease, keloid, old myocardial infarction, scleroderma/systemic sclerosis, arthrofibrosis, and adhesive capsulitis of the breast, prostate, blood, brain, kidney, liver or skin. In a further embodiment, the fibrosis is idiopathic pulmonary fibrosis.

In the methods described herein, the subjects treated can be further treated with one or more additional agents. The one or more additional agents and the compounds described herein or pharmaceutically acceptable salts or prodrugs thereof can be administered together in a single composition (e.g., as an admixture) or in separate compositions in any order, including simultaneous administration, as well as temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Therapeutic agents include, but are not limited to, chemotherapeutic agents. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, bexarotene, gefitinib, erlotinib, gemcitabine, paclitaxel, docetaxel, topotecan, irinotecan, temozolomide, carmustine, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g. anthracyclines such as doxorubicin, liposomal doxorubicin, and diethylstilbestrol doxorubicin, bleomycin, daunorubicin, and dactinomycin); antiestrogens (e.g., tamoxifen); antimetabolites (e.g., fluorouracil (FU), 5-FU, methotrexate, floxuridine, interferon alpha-2B, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chlorambucil, mechlorethamine (nitrogen mustard) and thiotepa); and steroids (e.g., bethamethasone sodium phosphate).

Therapeutic agents can also include, but are not limited to, pain medications (e.g., NSAIDs, tramadol, clonidine, narcotics, and opioids), agents that reduce blood pressure (e.g., antihypertensives or diuretics), and antibiotics. Therapeutic agents can further include prednisone, azathioprine, and N-acetylcysteine.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of a hyperproliferative disease), during early onset (e.g., upon initial signs and symptoms of a hyperproliferative disease), or after the development of a hyperproliferative disease. Prophylactic administration can occur for several days to years prior to the manifestation of symptoms of a hyperproliferative disease. Therapeutic treatment involves administering to a subject a therapeutically effective amount of the compounds and compositions or pharmaceutically acceptable salts thereof as described herein after a hyperproliferative disease is diagnosed.

The methods and compounds described herein are also useful in inhibiting the interaction between two or more heat shock protein chaperones in a cell. The methods of inhibiting the interaction between two or more heat shock protein chaperones in a cell comprise contacting a cell with a compound as described herein. Optionally, the two or more heat shock protein chaperones are selected from the group consisting of Hsp-90, Hsp-70, Hsc-70, and Hsp-40. Optionally, the method is performed in vitro. Optionally, the method is performed in vivo.

Optionally, the methods and compounds described herein can be used to regulate kinases involved in the phosphorylation of vimentin. For example, the methods and compounds described herein can be used to regulated cyclin dependent kinases (cdk), including Cdk5. Optionally, the regulation of kinases involved in the phosphorylation of vimentin using the methods and compounds described herein can result in vimentin filament disassembly. Optionally, the vimentin filament disassembly can result in increased apoptosis of cancer cells.

The methods herein for prophylactic and therapeutic treatment optionally comprise selecting a subject with or at risk of developing a hyperproliferative disease. A skilled artisan can make such a determination using, for example, a variety of prognostic and diagnostic methods, including, for example, a personal or family history of the disease or condition, clinical tests (e.g., imaging, biopsy, genetic tests), and the like.

V. Kits

Also provided herein are kits for treating or preventing hyperproliferative diseases in a subject. A kit can include any of the compounds or compositions described herein. For example, a kit can include a compound of Formula I, Formula II, Formula III, Formula IV, Formula V, Formula VI, or combinations thereof. A kit can further include one or more additional agents, such as chemotherapeutic agents, pain medications, agents that reduce blood pressure (e.g., antihypertensives or diuretics), antibiotics, prednisone, azathioprine, and N-acetylcysteine. A kit can include an oral formulation of any of the compounds or compositions described herein. A kit can include an intravenous formulation of any of the compounds or compositions described herein. A kit can additionally include directions for use of the kit (e.g., instructions for treating a subject), a container, a means for administering the compounds or compositions (e.g., a syringe), and/or a carrier.

VI. Methods of Screening

Methods of screening for a compound for treating a hyperproliferative disease are provided. Such methods involve the steps of contacting a cell with the candidate compound to be screened and determining the effect of the candidate compound on proliferation of hyperproliferating cells. The method can be performed in vitro or in vivo. The method provides an effective and reliable means of screening for compounds capable of treating a disease or condition caused, at least in part, by hyperproliferative cells.

Optionally, the method can include contacting a hyperproliferative cell with a candidate agent; obtaining a measurement indicative of cell growth, such as, but not limited to, cell number, cell viability, cell cycle progression, apoptotic frequency or activity of en enzyme involved in the apoptotic process; and identifying the candidate agent as a putative agent if the measurement of the property is significantly less than the baseline value of the property.

In one embodiment, such a screening assay can be performed, for example, by determining in an appropriate model system (such as, but not limited to, those systems described herein) the amount of inhibition of a measurement indicative of cell growth and detecting a difference in the level or activity of the foregoing in the presence of as compared to the absence of candidate compound.

The various screening assays may be combined with an in vivo assay entailing measuring the effect of the test compound on the symptoms the disease states and conditions discussed herein.

Suitable test compounds for use in the screening assays can be obtained from any suitable source, such as conventional compound libraries. The test compounds can also be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach includes peptide libraries, while the other four approaches include peptide, non-peptide oligomer, or small molecule libraries of compounds. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries and libraries of natural compounds in the form of bacterial, fungal, plant, and animal extracts are commercially available. In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

Examples of methods for the synthesis of molecular libraries can be found in the art. Libraries of compounds may be presented in solution or on beads, bacteria, spores, plasmids or phage.

A screening assay of the disclosure is particularly amenable to a high throughput format, thereby providing a means to screen, for example, a combinatorial library of small organic molecules, peptides, nucleic acid molecules, and the like.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1: Synthesis

A synthetic scheme for DBM-308 is shown in Scheme 1.

Scheme 1:

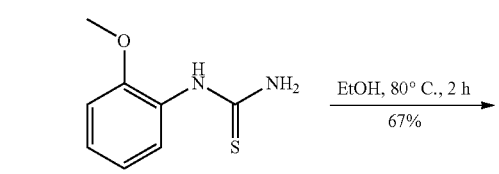

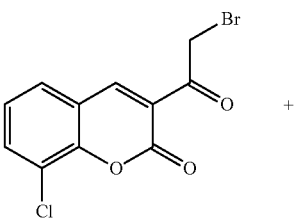

A synthetic scheme for DBM-E-1 is shown in Scheme 2.

Scheme 2:

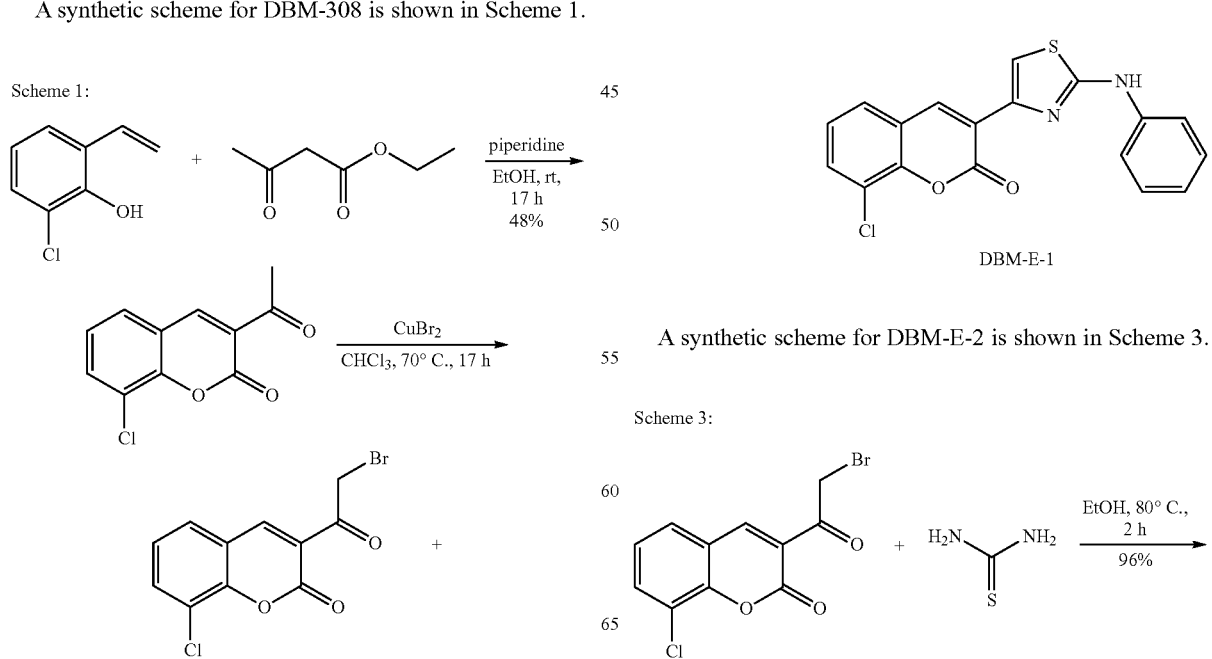

A synthetic scheme for DBM-E-2 is shown in Scheme 3.

Scheme 3:

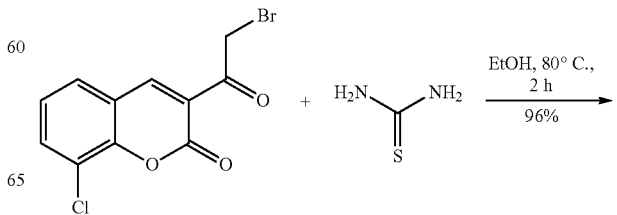

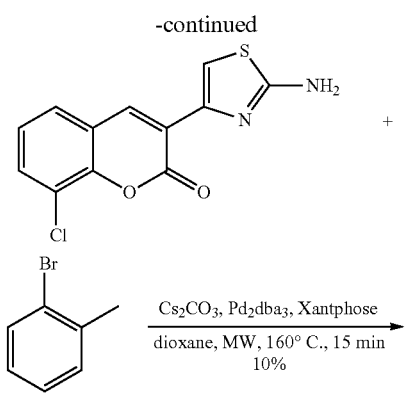

(q, J=7 Hz, 2H), 6.99-7.05 (m, 3H), 7.39 (t, J=8 Hz, 1H), 7.76-7.79 (m, 2H), 7.93 (t, J=7 Hz, 1H), 8.48-8.49 (m, 1H), 8.65 (s, 1H), 9.54 (s, 1H).

DBM-E-4 was prepared according to the procedure listed below and the synthetic scheme shown in Scheme 5.

Scheme 5:

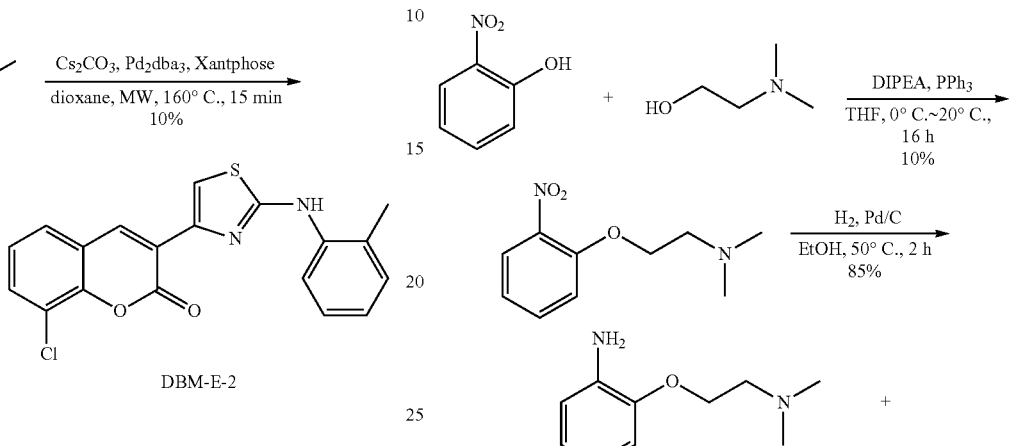

DBM-E-3 was prepared according to the procedure listed below and the synthetic scheme shown in Scheme 4.

Scheme 4:

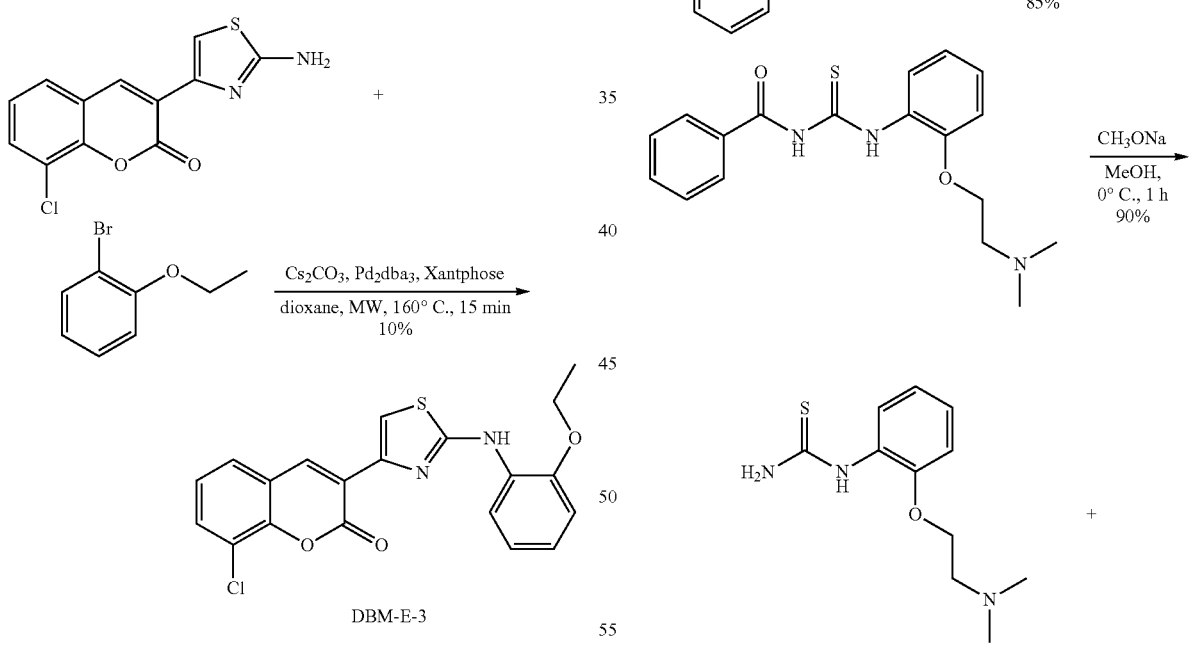

3-(2-bromoacetyl)-8-chloro-2H-chromen-2-one (150 mg, 0.54 mmol) and 1-bromo-2-ethoxybenzene (108 mg, 0.54 mmol) were reacted in a microwave in the presence of $Cs_2CO_3$ (528 mg, 1.62 mmol), $Pd_2(dba)_3$ (40 mg, 0.054 mmol.), xantphose (60 mg, 0.108 mmol), and dioxane (2 mL) at 160° C. for 15 minutes. The resulting product was then purified by pre-HPLC to yield 8-chloro-3-(2-(2-ethoxyphenylamino)thiazol-4-yl)-2H-chromen-2-one (20 mg, 10%) as a yellow solid. ESI-MS (EI$^+$, m/z): 399.1 [M+1]$^+$; $^1$HNMR (500 MHz, DMSO-d$_6$): δ 1.40 (t, J=7 Hz, 3H), 4.14

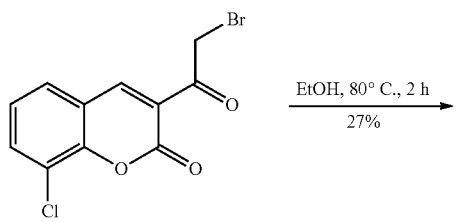

-continued

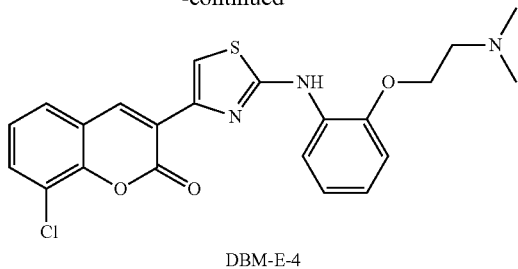

DBM-E-4

Step 1: N,N-dimethyl-2-(2-nitrophenoxy)ethanamine

To a solution of 2-nitrophenol (13.9 g, 10 mmol), 2-(dimethylamino)ethanol (10.7 g, 12 mmol), and PPh$_3$ (29 g, 11 mmol) in dry THF (200 mL) was added DIAD (22 g, 11 mmol) dropwise at 0° C. Then, the mixture was stirred at rt for 17 hrs. The solvent was removed. The residue was dissolved in 1 N HCl aq. and washed with EtOAc. The water layer was neutralized with saturated NaHCO$_3$ and extracted with EtOAc (2×). The organic layers were collected, washed with brine, dried (Na$_2$SO$_4$), and concentrated to afford N,N-dimethyl-2-(2-nitrophenoxy)ethanamine (2.1 g, 10%) as a yellow oil. ESI-MS (EI$^+$, m/z): 211.0 [M+1]$^+$.

Step 2: 2-(2-(dimethylamino)ethoxy)aniline

To a solution of N,N-dimethyl-2-(2-nitrophenoxy)ethanamine (1.0 g, 4.76 mmol) in EtOH (10 mL) was added Pd/C (800 mg, 10%). The mixture was stirred at 50° C. for 2 hrs under H$_2$. The reaction mixture was cooled down to rt and then filtered. The filtrate was concentrated to afford 2-(2-(dimethylamino)ethoxy)aniline (730 mg, 85%) as a yellow oil. ESI-MS (EI$^+$, m/z): 181.0 [M+1]$^+$.

Step 3: N-(2-(2-(dimethylamino)ethoxy)phenylcarbamothioyl)benzamide 2-(2-(dimethylamino)ethoxy)aniline (550 mg, 3 mmol) and benzoyl isothiocyanate (727 mg, 3.6 mmol) were reacted. The resulting mixture was then purified by filtration to provide N-(2-(2-(dimethylamino)ethoxy)phenylcarbamothioyl)benzamide (360 mg, 35%) as a white solid. ESI-MS (EI$^+$, m/z): 344.0 [M+1]$^+$.

Step 4: 1-(2-(2-(dimethylamino)ethoxy)phenyl)thiourea

N-(2-(2-(dimethylamino)ethoxy)phenylcarbamothioyl) benzamide (343 mg, 1.0 mmol) was reacted with a solution of NaOMe in MeOH (1 mL, 30%), and the resulting mixture was purified by filtration to provide 1-(2-(2-(dimethylamino)ethoxy)-phenyl)thiourea (160 mg, 67%) as a white solid. ESI-MS (EI$^+$, m/z): 240.0 [M+1]$^+$.

Step 5: 8-chloro-3-(2-(2-(2-(dimethylamino)ethoxy)phenylamino)thiazol-4-yl)-2H-chromen-2-one 3-(2-bromoacetyl)-8-chloro-2H-chromen-2-one (~279 mg, 50%, 0.53 mmol) and 1-(2-(2-(dimethylamino)ethoxy)phenyl)thiourea (106 mg, 0.44 mmol) were reacted in ethanol at 80° C. The product was then purified by filtration to provide 8-chloro-3-(2-(2-(2-(dimethylamino)ethoxy)phenylamino)thiazol-4-yl)-2H-chromen-2-one (60 mg, 31%) as a yellow solid. ESI-MS (EI$^+$, m/z): 442.0 [M+1]$^+$; $^1$H NMR (500 MHz, CF$_3$COOD): δ 3.64 (s, 6H), 4.27 (s, 2H), 5.02 (s, 2H), 7.65 (d, J=8.0 Hz, 1H), 7.75 (t, J=8.0 Hz, 1H), 7.94-7.99 (m, 2H), 8.12 (s, 1H), 8.14 (d, J=8.0 Hz, 1H), 8.20 (d, J=7.5 Hz, 1H), 8.33 (d, J=7.5 Hz, 1H), 9.03 (s, 1H)

DBM-E-5 was prepared according to the procedure listed below and the synthetic scheme shown in Scheme 6.

Scheme 6:

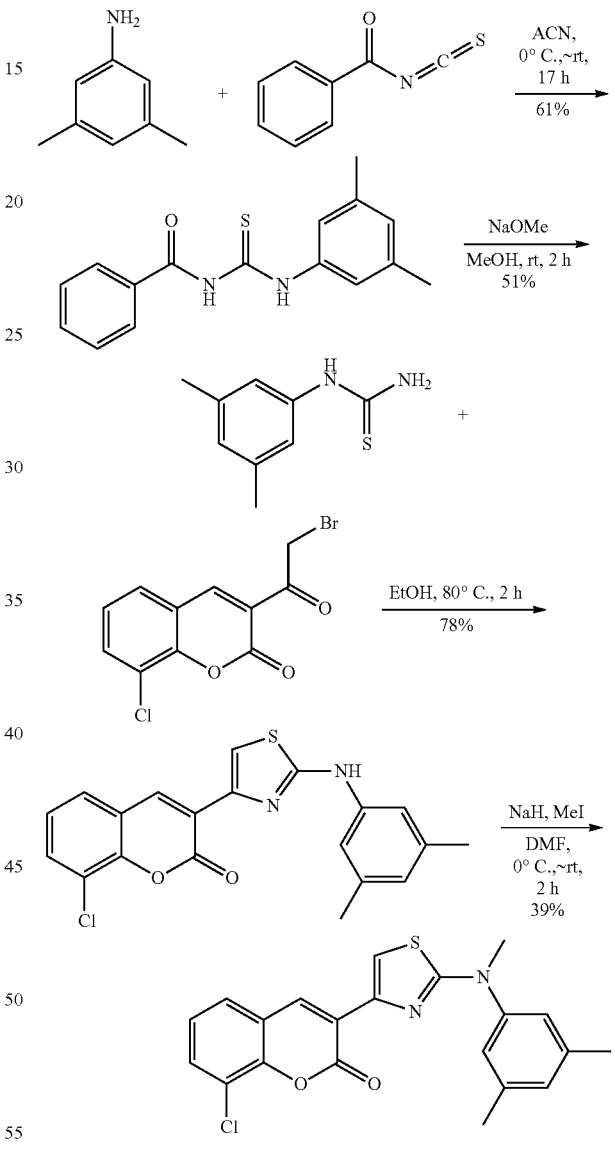

DBM-E-5

Step 1: N-(3,5-dimethylphenylcarbamothioyl)benzamide 3,5-dimethylaniline (2.42 g, 20 mmol) and benzoyl isothiocyanate (4.24 g, 26 mmol) in acetonitrile were reacted at a temperature of from 0° C. to room temperature over 17 hours. The resulting mixture was then purified by filtration to provide N-(3,5-dimethylphenylcarbamothioyl)benzamide (3.5 g, 61%) as a white solid. ESI-MS (EI+, m/z): 285.1 [M+1]+.

Step 2: 1-(3,5-dimethylphenyl)thiourea

N-(3,5-dimethylphenylcarbamothioyl)benzamide (3.5 g, 12.3 mmol) and a solution of NaOMe in MeOH (4 mL, 30%) were mixed at room temperature for two hours. The resulting mixture was then purified by filtration to provide 1-(3,5-dimethylphenyl)thiourea (1.1 g, 51%) as a white solid. ESI-MS (EI+, m/z): 181.0 [M+1]+.

Step 3: 8-chloro-3-(2-(3,5-dimethylphenylamino)thiazol-4-yl)-2H-chromen-2-one 3-(2-bromoacetyl)-8-chloro-2H-chromen-2-one (~1 g, 50%, 1.67 mmol) and 1-(3,5-dimethylphenyl)thiourea (600 mg, 3.33 mmol) were reacted in ethanol at 80° C. The product was then purified by filtration to provide 8-chloro-3-(2-(3,5-dimethylphenylamino)thiazol-4-yl)-2H-chromen-2-one (500 mg, 78%) as a yellow solid. ESI-MS (EI+, m/z): 383.0 [M+1]+;

Step 4: 8-chloro-3-(2-((3,5-dimethylphenyl)(methyl)amino)thiazol-4-yl)-2H-chromen-2-one To a solution of 8-chloro-3-(2-(3,5-dimethylphenylamino)thiazol-4-yl)-2H-chromen-2-one (150 mg, 0.39 mmol) in dry DMF (10 mL) was added NaH (31 mg, 60%, 0.78 mmol) at 0° C. The mixture was then stirred at 0° C. for 15 min. MeI (56 mg, 0.39 mmol) was added and the mixture was stirred at rt for 2 hrs. The reaction solution was quenched with saturated NH4Cl solution, diluted with EtOAc (80 mL), washed with H2O (2×) and brine (2×), dried (Na2SO4), filtered, and concentrated to give 8-chloro-3-(2-((3,5-dimethylphenyl)(methyl)amino)thiazol-4-yl)-2H-chromen-2-one (60 mg, 39%) as a yellow solid. ESI-MS (EI+, m/z): 397.0 [M+1]+; 1H NMR (500 MHz, DMSO-d6): δ 2.31 (s, 6H), 3.56 (s, 3H), 6.98 (s, 1H), 7.13 (s, 2H), 7.39 (t, J=8.0 Hz, 1H), 7.63 (s, 1H), 7.77 (d, J=8.0 Hz, 1H), 7.89 (d, J=7.5 Hz, 1H), 8.69 (s, 1H).

DBM-E-6 was prepared according to the procedure listed below and the synthetic scheme shown in Scheme 7.

Scheme 7:

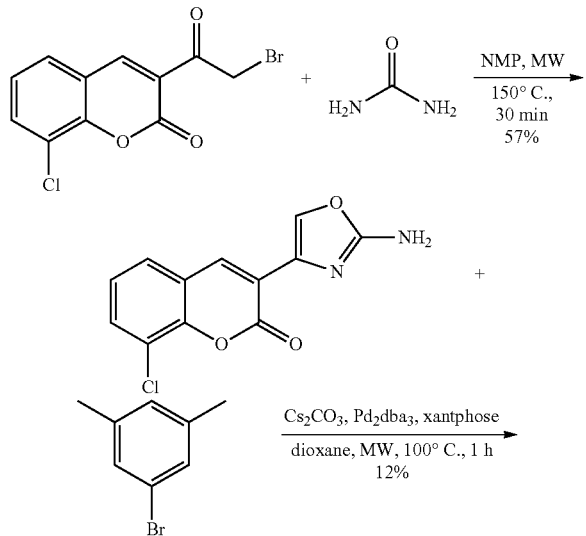

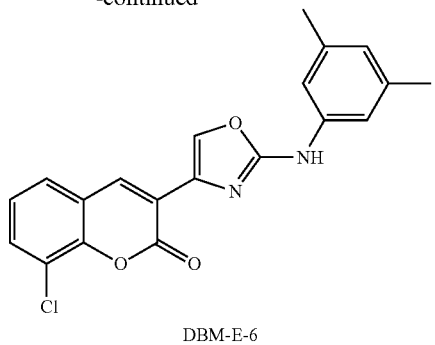

DBM-E-6

Step 1: 3-(2-aminooxazol-4-yl)-8-chloro-2H-chromen-2-one

To an oven-dried microwave vial was added 3-(2-bromoacetyl)-8-chloro-2H-chromen-2-one (600 mg, 50%, 1 mmol), urea (90 mg, 1.5 eq), and dry NMP (2 mL). The vial was capped and purged with nitrogen. The reaction mixture was heated to 150° C. for 30 minutes under microwave irradiation. Then, the mixture was allowed to cool and purified by pre-HPLC to afford 3-(2-aminooxazol-4-yl)-8-chloro-2H-chromen-2-one (150 mg, 57%) as a pale yellow solid. ESI-MS (EI+, m/z): 263.0 [M+1]+

Step 2: 8-chloro-3-(2-(3,5-dimethylphenylamino)oxazol-4-yl)-2H-chromen-2-one To an oven-dried microwave vial was added 3-(2-aminooxazol-4-yl)-8-chloro-2H-chromen-2-one (100 mg, 0.38 mmol), 1-bromo-3,5-dimethylbenzene (702 mg, 3.8 mmol), Cs2CO3 (249 mg, 0.76 mmol), Pd2(dba)3 (35 mg, 0.038 mmol), xantphose (44 mg, 0.076 mmol), and dry dioxane (3 mL). The vial was capped and purged with nitrogen. The reaction mixture was heated to 100° C. for 1 hour under microwave irradiation. The mixture was allowed to cool and diluted with EtOAc (100 mL), washed with H2O (2×) and brine (2×), dried (Na2SO4), filtered, and concentrated. The residue was purified by silica gel column chromatography (EtOAc/PE=0~10%) to get a crude product. The crude product was purified by pre-HPLC to afford 8-chloro-3-(2-(3,5-dimethylphenylamino)-oxazol-4-yl)-2H-chromen-2-one (17 mg, 12%) as a yellow solid. ESI-MS (EI+, m/z): 367.1 [M+1]+; 1HNMR (400 MHz, DMSO-d6): δ 2.30 (s, 6H), 6.64 (s, 1H), 7.34 (s, 1H), 7.41 (t, J=8.0 Hz, 2H), 7.77-7.79 (m, 1H), 7.95 (d, J=7 Hz, 1H), 8.20 (s, 1H), 8.50 (s, 1H), 10.18 (s, 1H).

DBM-E-7 was prepared according to the procedure listed below and the synthetic scheme shown in Scheme 8.

Scheme 8:

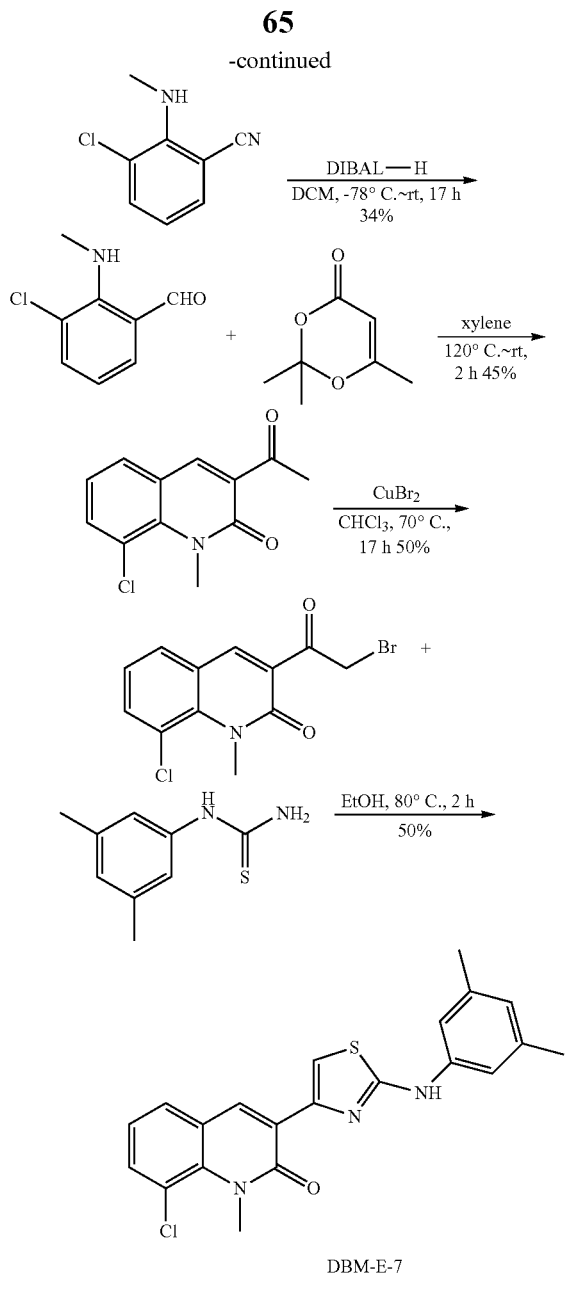

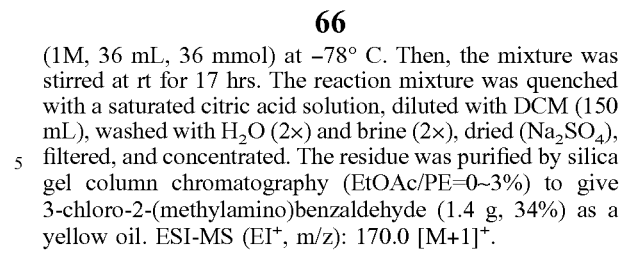

DBM-E-7

Step 1: 3-chloro-2-(methylamino)benzonitrile

To a solution of 2-amino-3-chlorobenzonitrile (5.0 g, 32.9 mmol) in dry DMF (60 mL) was added NaH (1.97 g, 60%, 49.3 mmol) at 0° C. Then, the mixture was stirred at 0° C. for 15 min. MeI (4.67 g, 32.9 mmol) was added and the mixture was stirred at rt for 2 hrs. The reaction solution was quenched with saturated NH₄Cl solution, diluted with EtOAc (200 mL), washed with H₂O (2×) and brine (2×), dried (Na₂SO₄), filtered, and concentrated. The residue was purified by silica gel column chromatography (EtOAc/PE=0~5%) to give 3-chloro-2-(methylamino)benzonitrile (4.8 g, 88%) as a white solid. ESI-MS (EI⁺, m/z): 167.0 [M+1]⁺.

Step 2: 3-chloro-2-(methylamino)benzaldehyde

To a solution of 3-chloro-2-(methylamino)benzonitrile (4 g, 24 mmol) in dry DCM (50 mL) was added DIBAL-H (1M, 36 mL, 36 mmol) at −78° C. Then, the mixture was stirred at rt for 17 hrs. The reaction mixture was quenched with a saturated citric acid solution, diluted with DCM (150 mL), washed with H₂O (2×) and brine (2×), dried (Na₂SO₄), filtered, and concentrated. The residue was purified by silica gel column chromatography (EtOAc/PE=0~3%) to give 3-chloro-2-(methylamino)benzaldehyde (1.4 g, 34%) as a yellow oil. ESI-MS (EI⁺, m/z): 170.0 [M+1]⁺.

Step 3: 3-acetyl-8-chloro-1-methylquinolin-2(1H)-one

A solution of 3-chloro-2-(methylamino)benzaldehyde (800 mg, 4.7 mmol) in xylene (30 mL) at 120° C. was treated with 2,2,6-trimethyl-4H-1,3-dioxin-4-one (6.7 g, 47 mmol). The reaction mixture was heated at 120° C. for 2 hrs and then cooled to rt. The solvent was removed and the residue was purified by silica gel column chromatography (EtOAc/PE=0~3%) to give 3-acetyl-8-chloro-1-methylquinolin-2 (1H)-one (500 mg, 45%) as a yellow solid. ESI-MS (EI⁺, m/z): 236.0 [M+1]⁺; ¹H NMR (500 MHz, DMSO-d₆): δ 2.61 (s, 3H), 3.86 (s, 3H), 7.31 (t, J=8 Hz, 1H), 7.79-7.81 (m, 1H), 7.92-7.94 (m, 1H), 8.41 (s, 1H).

Step 4: 3-(2-bromoacetyl)-8-chloro-1-methylquinolin-2(1H)-one

To a solution of 3-acetyl-8-chloro-1-methylquinolin-2 (1H)-one (432 mg, 1.84 mmol) in CHCl₃ (20 mL) was added CuBr₂ (404 mg, 1.84 mmol) at rt. The mixture was stirred at 70° C. for 17 hrs. The solvent was evaporated, the crude product was diluted with EtOAc (100 mL), washed with water (2×), brine (2×), dried (Na₂SO₄), and concentrated to provide 3-(2-bromoacetyl)-8-chloro-1-methylquinolin-2 (1H)-one (~500 mg, 50%), which was used directly in the next step. ESI-MS (EI⁺, m/z): 313.9 [M+H]⁺.

Step 5: 8-chloro-3-(2-(3,5-dimethylphenylamino) thiazol-4-yl)-1-methylquinolin-2(1H)-one 3-(2-bromoacetyl)-8-chloro-1-methylquinolin-2(1H)-one (~200 mg, 50%, 0.32 mmol) and 1-(3,5-dimethylphenyl) thiourea (115 mg, 0.64 mmol) were reacted in ethanol at 80° C. The product was then purified by filtration to provide 8-chloro-3-(2-(3,5-dimethylphenylamino)thiazol-4-yl)-1-methylquinolin-2(1H)-one (50 mg, 50%) as a yellow solid. ESI-MS (EI⁺, m/z): 396.0 [M+1]⁺; ¹HNMR (500 MHz, DMSO-d₆): δ 2.31 (s, 6H), 3.94 (s, 3H), 6.64 (s, 1H), 7.29-7.35 (m, 3H), 7.69-7.71 (m, 1H), 7.81 (d, J=7.0 Hz, 1H), 7.99 (s, 1H), 8.58 (s, 1H), 10.16 (s, 1H).

DBM-E-8 was prepared according to the procedure listed below and the synthetic scheme shown in Scheme 9.

Scheme 9:

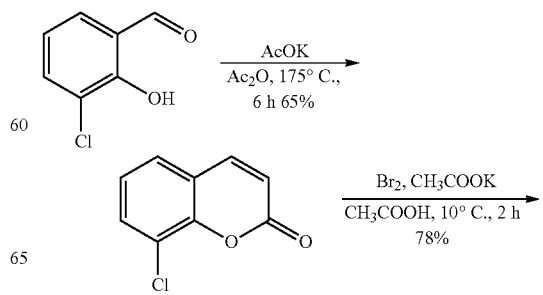

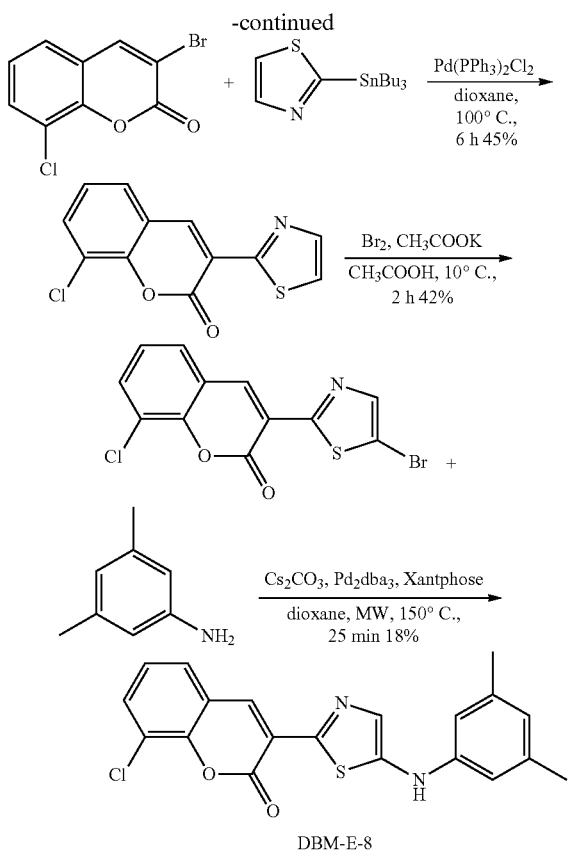

DBM-E-8

Step 1: 8-chloro-2H-chromen-2-one

A mixture of 3-chloro-2-hydroxybenzaldehyde (1 g, 6.4 mmol) and $CH_3COOH$ (1.3 g, 12.8 mmol) in $Ac_2O$ (45 mL) was heated to 175° C. for 6 hrs. The mixture was then cooled down to rt. The precipitate which formed was collected to give 8-chloro-2H-chromen-2-one (1.02 g, 88%) as a brown solid. ESI-MS (EI+, m/z): 181.0 [M+1]+.

Step 2: 3-bromo-8-chloro-2H-chromen-2-one

To a mixture of 8-chloro-2H-chromen-2-one (1 g, 5.56 mmol) and $CH_3COOK$ (1.09 g, 11.1 mmol) in $CH_3COOH$ (30 mL) was added $Br_2$ (4.4 g, 27.8 mmol). The mixture was stirred at 50° C. for 4 hrs. The reaction mixture was cooled to rt and poured into water (100 mL) and filtered to get a brown solid. The crude product was purified by silica gel column chromatography (EtOAc/PE=0~5%) to give 3-bromo-8-chloro-2H-chromen-2-one (640 mg, 45%) as a yellow solid. ESI-MS (EI+, m/z): 260.9 [M+1]+.

Step 3: 8-chloro-3-(thiazol-2-yl)-2H-chromen-2-one

A mixture of 3-bromo-8-chloro-2H-chromen-2-one (620 mg, 2.4 mmol), 2-(tributylstannyl)thiazole (1.8 g, 4.8 mmol), and $Pd(PPh_3)_4$ (276 mg, 0.24 mmol) in dry dioxane (20 mL) was heated to 100° C. for 6 hrs. The reaction mixture was then cooled to rt and concentrated. The residue was purified by silica gel column chromatography (EtOAc/PE=0~30%) to give 8-chloro-3-(thiazol-2-yl)-2H-chromen-2-one (500 mg, 79%) as a yellow solid. ESI-MS (EI+, m/z): 264.0 [M+1]+.

Step 4: 3-(5-bromothiazol-2-yl)-8-chloro-2H-chromen-2-one

To a mixture of 8-chloro-3-(thiazol-2-yl)-2H-chromen-2-one (400 mg, 1.52 mmol) and $CH_3COOK$ (447 mg, 4.56 mmol) in $CH_3COOH$ (15 ml) was added $Br_2$ (479 mg, 3.04 mmol). Then, the mixture was stirred at rt for 2 hrs. The reaction mixture was poured into water (100 mL) and filtered to get a brown solid. The crude product was purified by silica gel column chromatography (EtOAc/PE=0~20%) to give 3-(5-bromothiazol-2-yl)-8-chloro-2H-chromen-2-one (250 mg, 48%) as a yellow solid. ESI-MS (EI+, m/z): 342.0 [M+1]+.

Step 5: 8-chloro-3-(5-(3,5-dimethylphenylamino)thiazol-2-yl)-2H-chromen-2-one 3-(5-bromothiazol-2-yl)-8-chloro-2H-chromen-2-one (100 mg, 0.3 mmol) and 3,5-dimethylaniline (182 mg, 1.5 mmol) were reacted in a microwave in the presence of $Cs_2CO_3$ (293 mg, 0.9 mmol), $Pd_2(dba)_3$ (21 mg, 0.03 mmol.), xantphose (52 mg, 0.09 mmol), and dioxane (2 mL) at 150° C. for 25 minutes. The mixture was then purified by pre-HPLC to provide 8-chloro-3-(5-(3,5-dimethylphenylamino)thiazol-2-yl)-2H-chromen-2-one (25 mg, 22%) as a yellow solid. ESI-MS (EI+, m/z): 383.1 [M+1]+; 1H NMR (500 MHz, DMSO-d6): δ 2.25 (s, 6H), 6.56 (s, 1H), 6.74 (s, 2H), 7.43 (t, J=8 Hz, 1H), 7.63 (s, 1H), 7.79-7.81 (m, 1H), 7.93-7.94 (m, 1H), 8.81 (s, 1H), 9.15 (s, 1H).

DBM-E-10 was prepared according to the procedure listed below and the synthetic scheme shown in Scheme 10.

Scheme 10:

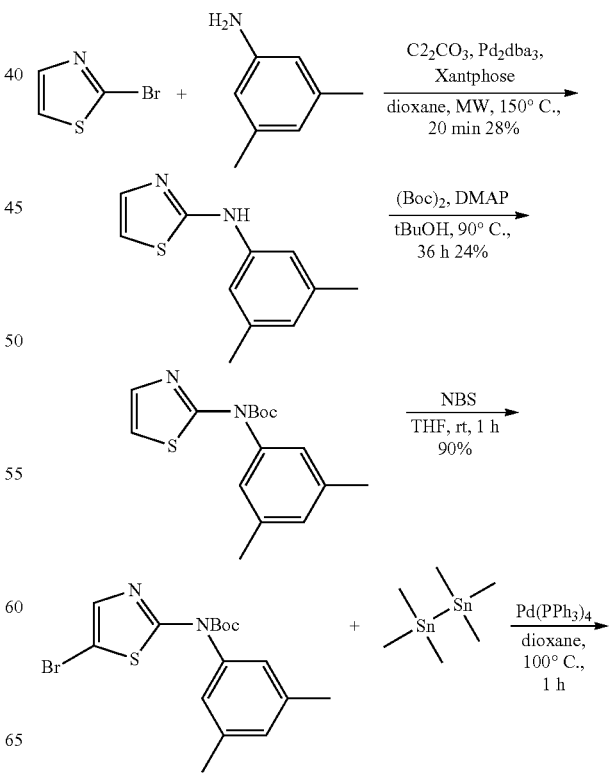

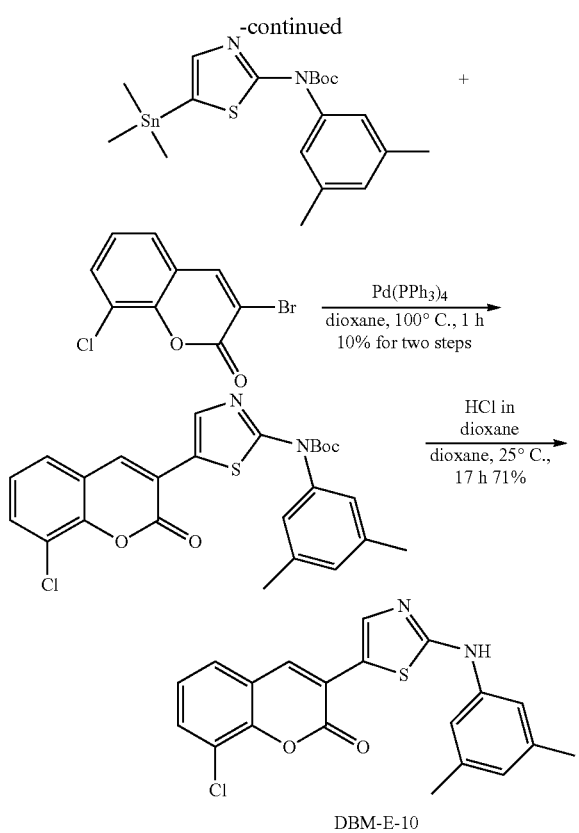

Step 1: N-(3,5-dimethylphenyl)thiazol-2-amine

2-Bromothiazole (3.26 g, 20 mmol), 3,5-dimethylaniline (3.6 g, 30 mmol) and p-toluenesulfonic acid (1.7 g, 10 mmol) were dissolved in i-propanol (50 mL). The mixture was stirred at 80° C. for 17 hrs. The reaction mixture was diluted with EtOAc (200 mL), washed with H$_2$O (2×) and brine (2×), dried (Na$_2$SO$_4$), filtered, and concentrated. The residue was purified by silica gel column chromatography (EtOAc/PE=0~20%) to give N-(3,5-dimethylphenyl)thiazol-2-amine (1.1 g, 27%) as a white solid. ESI-MS (EI$^+$, m/z): 205.0 [M+1]$^+$.

Step 2: tert-butyl 3,5-dimethylphenyl(thiazol-2-yl)carbamate

A mixture of N-(3,5-dimethylphenyl)thiazol-2-amine (1.02 g, 5 mmol), (Boc)$_2$O (5.45 g, 25 mmol) and DMAP (1.52 g, 12.5 mmol) in t-BuOH (20 mL) was heated to 80° C. for 36 hrs. The solvent was removed and the residue was purified by silica gel column chromatography (EtOAc/PE=0~5%) to give tert-butyl 3,5-dimethylphenyl(thiazol-2-yl)carbamate (360 mg, 24%) as a white solid. ESI-MS (EI$^+$, m/z): 305.0 [M+1]$^+$.

Step 3: tert-butyl 5-bromothiazol-2-yl(3,5-dimethylphenyl)carbamate

To a mixture of tert-butyl 3,5-dimethylphenyl(thiazol-2-yl)carbamate (390 mg, 1.28 mmol) in THF (15 mL) was added NBS (252 mg, 1.41 mmol) at rt. Then the mixture was stirred at rt for 1 h. The solvent was removed and the residue was purified by silica gel column chromatography (EtOAc/PE=0~5%) to give tert-butyl 5-bromothiazol-2-yl(3,5-dimethylphenyl)carbamate (445 mg, 90%) as a pale yellow solid. ESI-MS (EI$^+$, m/z): 385.0 [M+1]$^+$.

Step 4: tert-butyl 3,5-dimethylphenyl(5-(trimethylstannyl)thiazol-2-yl)carbamate A mixture of tert-butyl 5-bromothiazol-2-yl(3,5-dimethylphenyl)carbamate (445 mg, 1.17 mmol), 1,1,1,2,2,2-hexamethyldistannane (579 mg, 1.76 mmol), and Pd(PPh$_3$)$_2$Cl$_2$ (83 mg, 0.12 mmol) in dioxane (15 mL) was stirred at 100° C. for 1 h. Then the mixture was cooled to rt and quenched with a saturated KF solution. The mixture was stirred at rt for 1 h, diluted with EtOAc (100 mL), washed with H$_2$O (2×) and brine (2×), dried (Na$_2$SO$_4$), filtered, and concentrated. The crude product tert-butyl 3,5-dimethylphenyl(5-(trimethylstannyl)thiazol-2-yl)carbamate (~500 mg) was used directly in the next step. ESI-MS (EI$^+$, m/z): 469.0 [M+1]$^+$.

Step 5: tert-butyl-5-(8-chloro-2-oxo-2H-chromen-3-yl)thiazol-2-yl(3,5-dimethylphenyl) carbamate A mixture of tert-butyl 3,5-dimethylphenyl(5-(trimethylstannyl)thiazol-2-yl) carbamate (~500 mg), 3-bromo-8-chloro-2H-chromen-2-one (300 mg, 1.16 mmol), and Pd(PPh$_3$)$_2$Cl$_2$ (83 mg, 0.12 mmol) in dioxane (15 mL) was stirred at 100° C. for 1 h. Then, the mixture was cooled to rt, diluted with EtOAc (100 mL), washed with H$_2$O (2×) and brine (2×), dried (Na$_2$SO$_4$), filtered, and concentrated. The residue was purified by pre-HPLC to give tert-butyl5-(8-chloro-2-oxo-2H-chromen-3-yl)thiazol-2-yl(3,5-dimethylphenyl)carbamate (30 mg, 10% for two steps) as a yellow solid. ESI-MS (EI$^+$, m/z): 483.0 [M+1]$^+$.

Step 5: 8-chloro-3-(2-(3,5-dimethylphenylamino) thiazol-5-yl)-2H-chromen-2-one To a solution of tert-butyl-5-(8-chloro-2-oxo-2H-chromen-3-yl)thiazol-2-yl(3,5-dimethylphenyl)carbamate (25 mg, 0.05 mmol) in dioxane (2 mL) was added a solution of HCl in dioxane (4M, 60 mL). The mixture was stirred at 25° C. for 17 hrs. Then the solvent was removed. The solid was washed with Et$_2$O to afford 8-chloro-3-(2-(3,5-dimethylphenylamino)thiazol-5-yl)-2H-chromen-2-one (17 mg, 71%) as a yellow solid. ESI-MS (EI$^+$, m/z): 383.1 [M+1]$^+$; $^1$H NMR (400 MHz, CF$_3$COOD): δ 2.91 (s, 6H), 7.58 (s, 2H), 7.71 (s, 1H), 7.96 (t, J=8.0 Hz, 1H), 8.16 (d, J=8.0 Hz, 1H), 8.30 (d, J=8.0 Hz, 1H), 8.61 (s, 1H), 8.82 (s, 1H).

A synthetic scheme for DBM-E-11 is shown in Scheme 11.

Scheme 11:

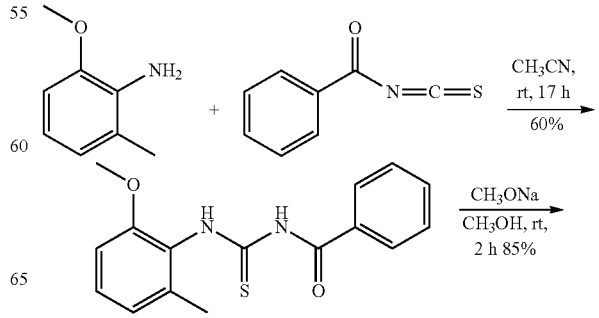

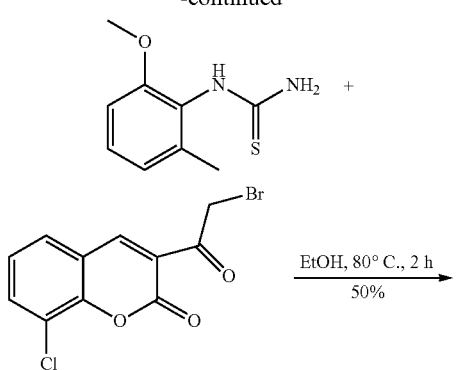
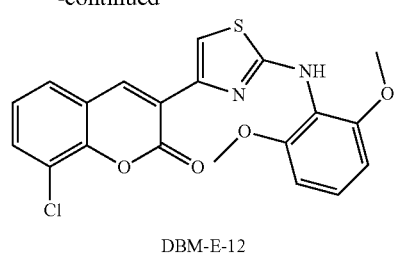
DBM-E-13 was prepared according to the procedure listed below and the synthetic scheme shown in Scheme 13.
A synthetic scheme for DBM-E-12 is shown in Scheme 12.
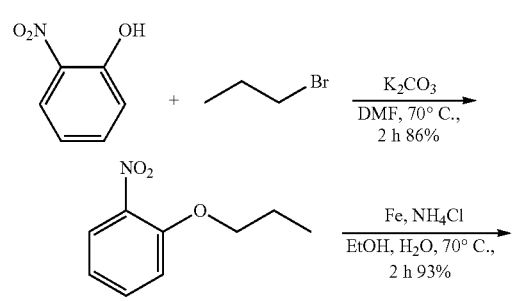

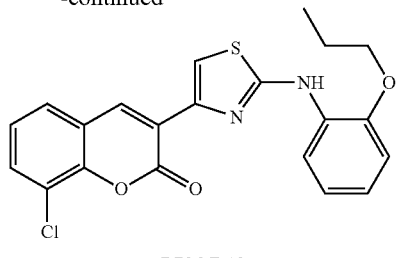

DBM-E-13

Step 1: 1-nitro-2-propoxybenzene

A mixture of 2-nitrophenol (3 g, 21.6 mmol), 1-bromopropane (3.9 g, 32.4 mmol), and $K_2CO_3$ (8.9 g, 64.8 mmol) in DMF (50 mL) was stirred at 70° C. for 2 hrs. The reaction mixture was cooled to rt, diluted with EtOAc (150 mL), washed with $H_2O$ (2×) and brine (2×), dried ($Na_2SO_4$), filtered, and concentrated. The residue was purified by silica gel column chromatography (EtOAc/PE=0~3%) to give 1-nitro-2-propoxybenzene (3.36 g, 86%) as a yellow oil. ESI-MS (EI$^+$, m/z): 182.0 [M+1]$^+$.

Step 2: 2-propoxyaniline

A mixture of 1-nitro-2-propoxybenzene (1.5 g, 8.3 mol), Fe (2.32 g, 41.5 mmol), $NH_4Cl$ (2.19 g, 41.5 mmol) in EtOH (20 mL) and $H_2O$ (2 mL) was stirred at 90° C. for 2 hrs. The reaction mixture was filtered. The filtrate was concentrated and the residue was diluted with DCM (100 mL), dried ($Na_2SO_4$), filtered, and concentrated to afford 2-propoxyaniline (1.16 g, 93%) as yellow oil. ESI-MS (EI$^+$, m/z): 152.0 [M+1]$^+$.

Step 3: N-(2-propoxyphenylcarbamothioyl)benzamide 2-propoxyaniline (1.16 g, 7.68 mmol) and benzoyl isothiocyanate (1.63 g, 10.0 mmol) were reacted in acetonitrile at a temperature of from 0° C. to room temperature over 3 hours. The mixture was then purified by filtration to provide N-(2-propoxyphenylcarbamothioyl)benzamide (1.36 g, 56%) as a white solid. ESI-MS (EI$^+$, m/z): 315.0 [M+1]$^+$.

Step 4: 1-(2-propoxyphenyl)thiourea

N-(2-propoxyphenylcarbamothioyl)benzamide (1.36 g, 4.3 mmol) was reacted with a solution of NaOMe in MeOH (4 mL, 30%). The resulting mixture was then purified by filtration to provide 1-(2-propoxyphenyl)thiourea (650 mg, 71%) as a white solid. ESI-MS (EI$^+$, m/z): 211.0 [M+1]$^+$.

Step 5: 8-chloro-3-(2-(2-propoxyphenylamino)thiazol-4-yl)-2H-chromen-2-one 3-(2-bromoacetyl)-8-chloro-2H-chromen-2-one (~300 mg, 50%, 0.5 mmol) and 1-(2-propoxyphenyl)thiourea (158 mg, 0.75 mmol) were reacted in ethanol at 80° C. The product was then purified by filtration to provide 8-chloro-3-(2-(2-propoxyphenylamino)thiazol-4-yl)-2H-chromen-2-one (115 mg, 56%) as a yellow solid. ESI-MS (EI$^+$, m/z): 413.0 [M+1]$^+$; $^1$H NMR (400 MHz, DMSO-$d_6$): δ 0.99 (t, J=7.2 Hz, 3H), 1.78-1.84 (m, 2H), 4.03 (t, J=6.8 Hz, 2H), 7.01-7.05 (m, 3H), 7.39 (t, J=8 Hz, 1H), 7.76-7.79 (m, 2H), 7.93 (d, J=7.6 Hz, 1H), 8.41-8.44 (m, 1H), 8.64 (s, 1H), 9.49 (s, 1H).

A synthetic scheme for DBM-E-14 is shown in Scheme 14.

Scheme 14:

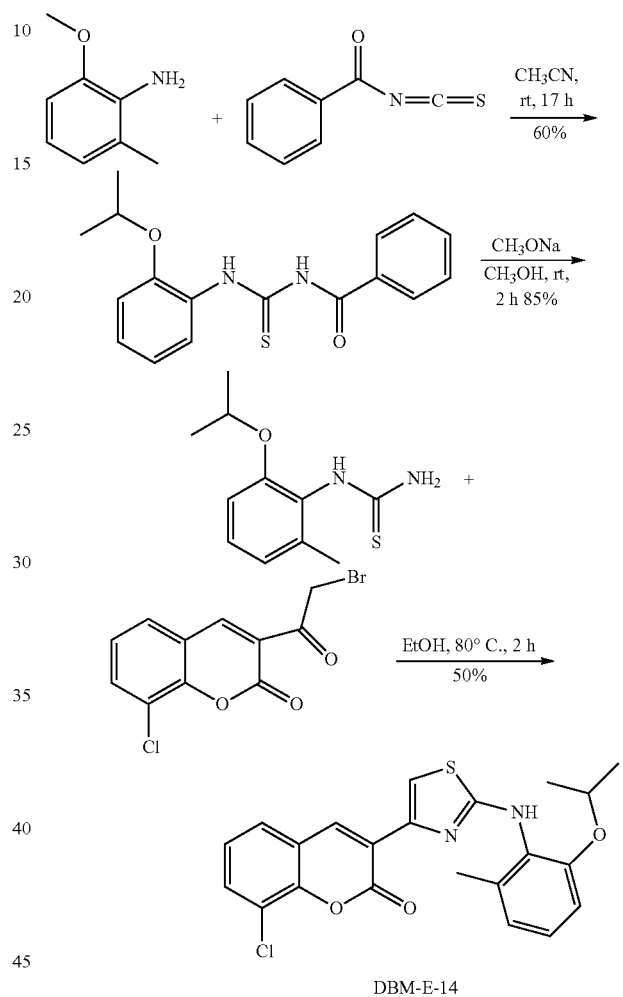

DBM-E-14

A synthetic scheme for DBM-E-15 is shown in Scheme 15.

Scheme 15:

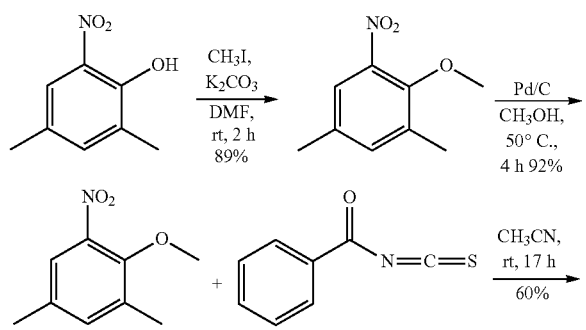

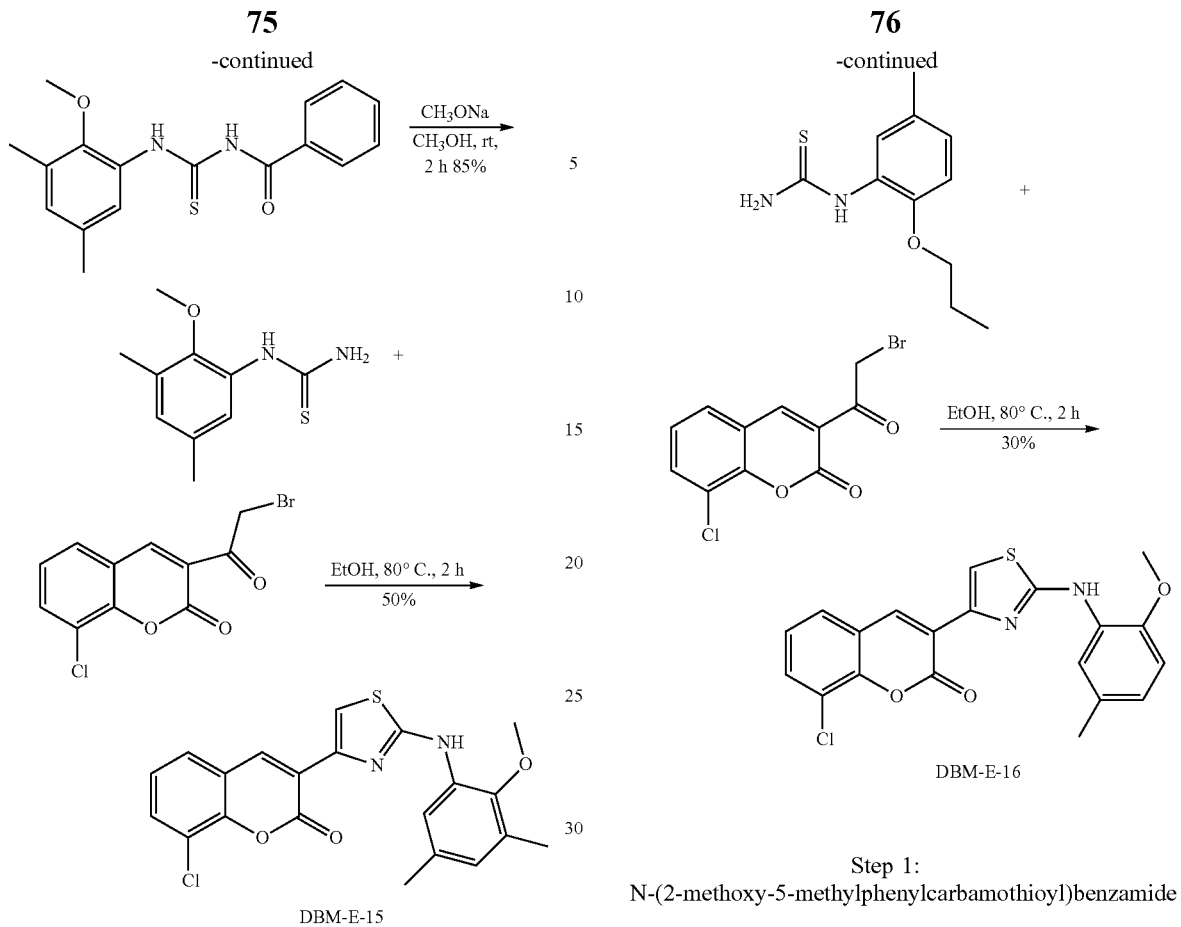

DBM-E-16 was prepared according to the procedure listed below and the synthetic scheme shown in Scheme 16.

Scheme 16:

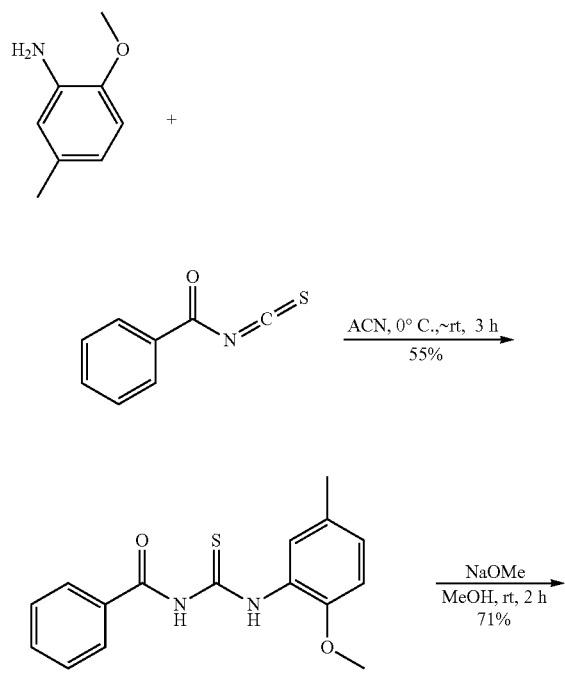

Step 1: N-(2-methoxy-5-methylphenylcarbamothioyl)benzamide 2-methoxy-5-methylaniline (500 mg, 3.65 mmol) and benzoyl isothiocyanate (773 mg, 4.74 mmol were reacted in acetonitrile at a temperature of from 0° C. to room temperature over 2 hours. The mixture was then purified by filtration to provide N-(2-methoxy-5-methylphenylcarbamothioyl) benzamide (600 mg, 55%) as a white solid. ESI-MS (EI+, m/z): 301.1 [M+1]+.

Step 2: 1-(2-methoxy-5-methylphenyl)thiourea

N-(2-methoxy-5-methylphenylcarbamothioyl)-benzamide (600 mg, 2 mmol) was reacted with a solution of NaOMe in MeOH (0.7 mL, 30%). The resulting mixture was then purified by filtration to provide 1-(2-methoxy-5-methylphenyl)thiourea (300 mg, 76%) as a white solid. ESI-MS (EI+, m/z): 197.0 [M+1]+.

Step 3: 8-chloro-3-(2-(2-methoxy-5-methylphenylamino)thiazol-4-yl)-2H-chromen-2-one 3-(2-bromoacetyl)-8-chloro-2H-chromen-2-one (~300 mg, 50%, 0.5 mmol) and 1-(2-methoxy-5-methylphenyl) thiourea (197 mg, 1 mmol) were reacted in ethanol at 80° C. The product was then purified by filtration to provide 8-chloro-3-(2-(2-methoxy-5-methylphenylamino)thiazol-4-yl)-2H-chromen-2-one (60 mg, 30%) as a yellow solid. ESI-MS (EI+, m/z): 399.0 [M+1]+; $^1$H NMR (400 MHz, DMSO-$d_6$): δ 2.36 (s, 3H), 3.84 (s, 3H), 6.82 (d, J=8.4 Hz, 1H), 6.93 (d, J=8.4 Hz, 1H), 7.39 (t, J=8.0 Hz, 1H), 7.75-7.77 (m, 2H), 7.83 (d, J=7.6 Hz, 1H), 8.29 (s, 1H), 8.58 (s, 1H), 9.62 (s, 1H).

A synthetic scheme for DBM-E-17 is shown in Scheme 17.

Scheme 17:
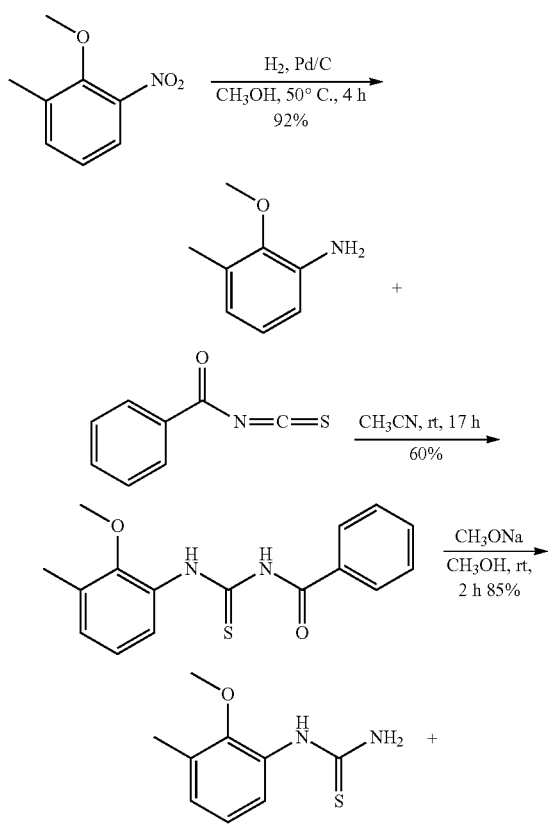
A synthetic scheme for DBM-E-18 is shown in Scheme 18.
Scheme 18:
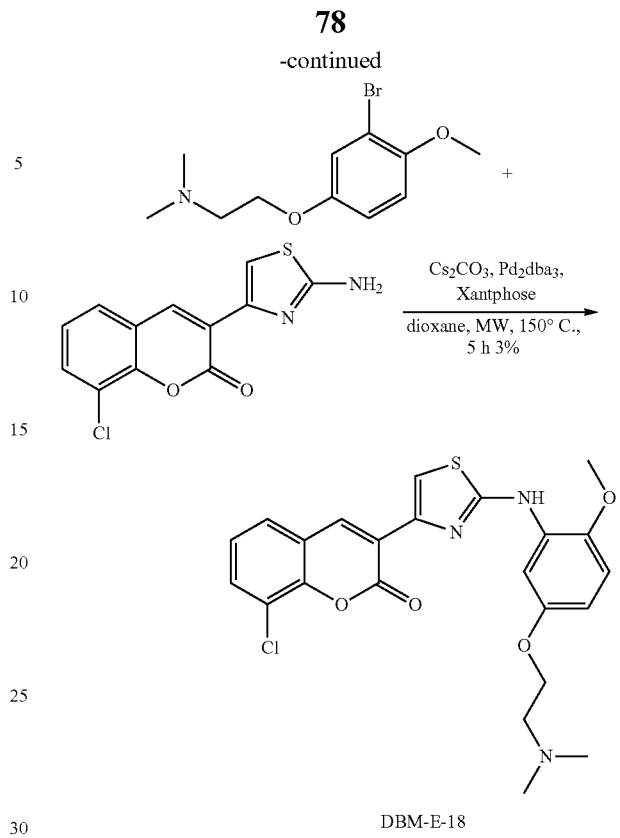
DBM-E-20 was prepared according to the procedure listed below and the synthetic scheme shown in Scheme 19.
Scheme 19:
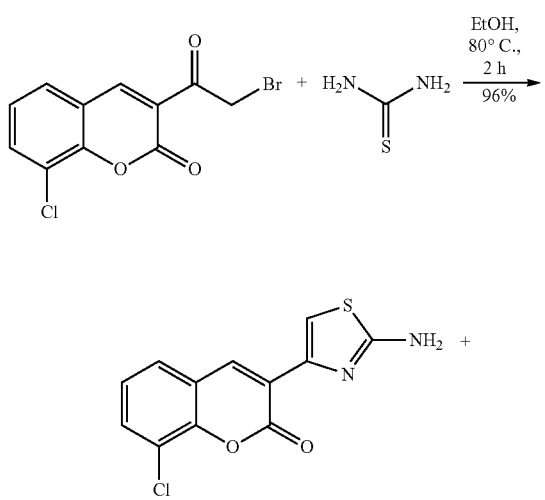
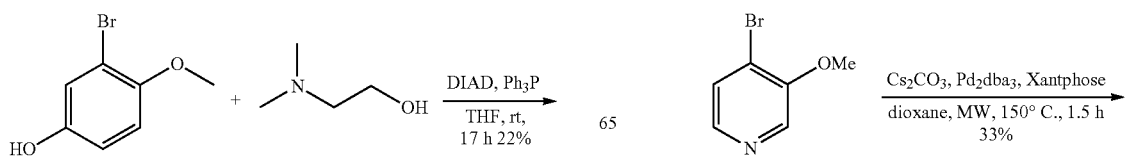

-continued

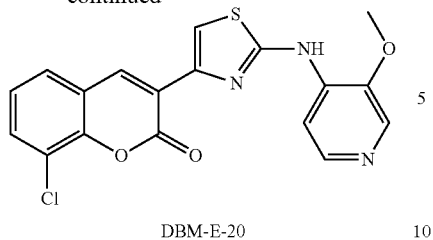

DBM-E-20

Step 1: 3-(2-aminothiazol-4-yl)-8-chloro-2H-chromen-2-one

A mixture of 3-(2-bromoacetyl)-8-chloro-2H-chromen-2-one (~1.4 g, 50%, 2.33 mmol) and thiourea (355 mg, 4.67 mmol) in EtOH (25 mL) was stirred at 80° C. for 2 hrs. The precipitate which formed was collected to give 3-(2-aminothiazol-4-yl)-8-chloro-2H-chromen-2-one (630 mg, 96%) as a yellow solid. ESI-MS (EI⁺, m/z): 279.0 [M+1]⁺;

Step 2: 8-chloro-3-(2-(3-methoxypyridin-4-ylamino)thiazol-4-yl)-2H-chromen-2-one 3-(2-aminothiazol-4-yl)-8-chloro-2H-chromen-2-one (100 mg, 0.36 mmol) and 4-bromo-3-methoxypyridine hydrochloride (80 mg, 0.36 mmol) were reacted in a microwave in the presence of Cs$_2$CO$_3$ (351 mg, 1.08 mmol), Pd$_2$(dba)$_3$ (25 mg, 0.036 mmol), xantphose (41 mg, 0.072 mmol), and dry dioxane (2 mL) at 150° C. for 1.5 hr. The mixture was then purified by pre-HPLC to provide 8-chloro-3-(2-(3-methoxypyridin-4-ylamino)thiazol-4-yl)-2H-chromen-2-one (45 mg, 33%) as a yellow solid. ESI-MS (EI⁺, m/z): 386.1 [M+1]⁺; ¹H NMR (400 MHz, DMSO-d$_6$): δ 3.98 (s, 3H), 7.42 (t, J=8 Hz, 1H), 7.77-7.79 (m, 1H), 7.92 (s, 1H), 8.00 (d, J=7 Hz, 1H), 8.21-8.26 (m, 2H), 8.68-8.74 (m, 2H), 10.27 (s, 1H).

A synthetic scheme for DBM-E-22 is shown in Scheme 20.

Scheme 20:

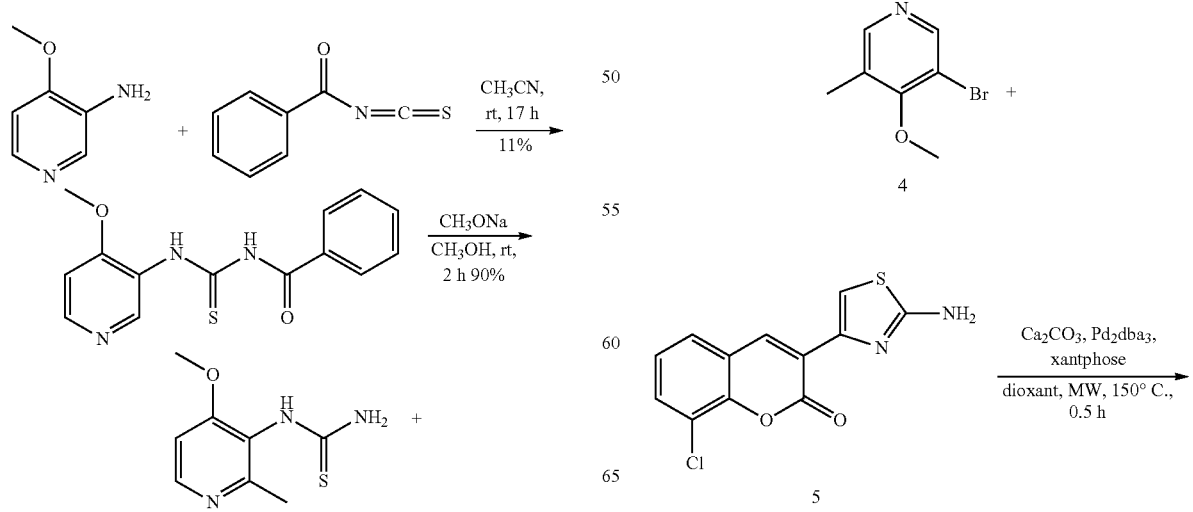

-continued

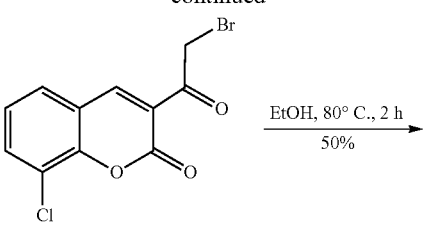

EtOH, 80° C., 2 h
50%

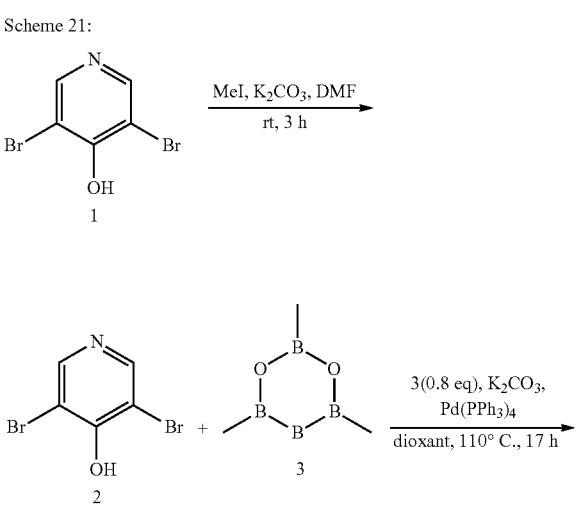

DBM-E-22

A synthetic scheme for DBM-E-23 is shown in Scheme 21.

Scheme 21:

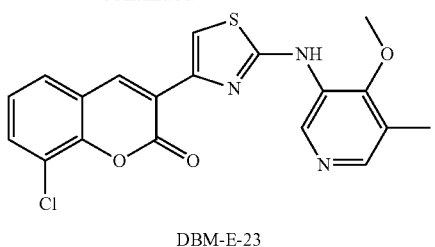

DBM-E-23

A synthetic scheme for DBM-E-9 is shown in Scheme 22.

Scheme 22:

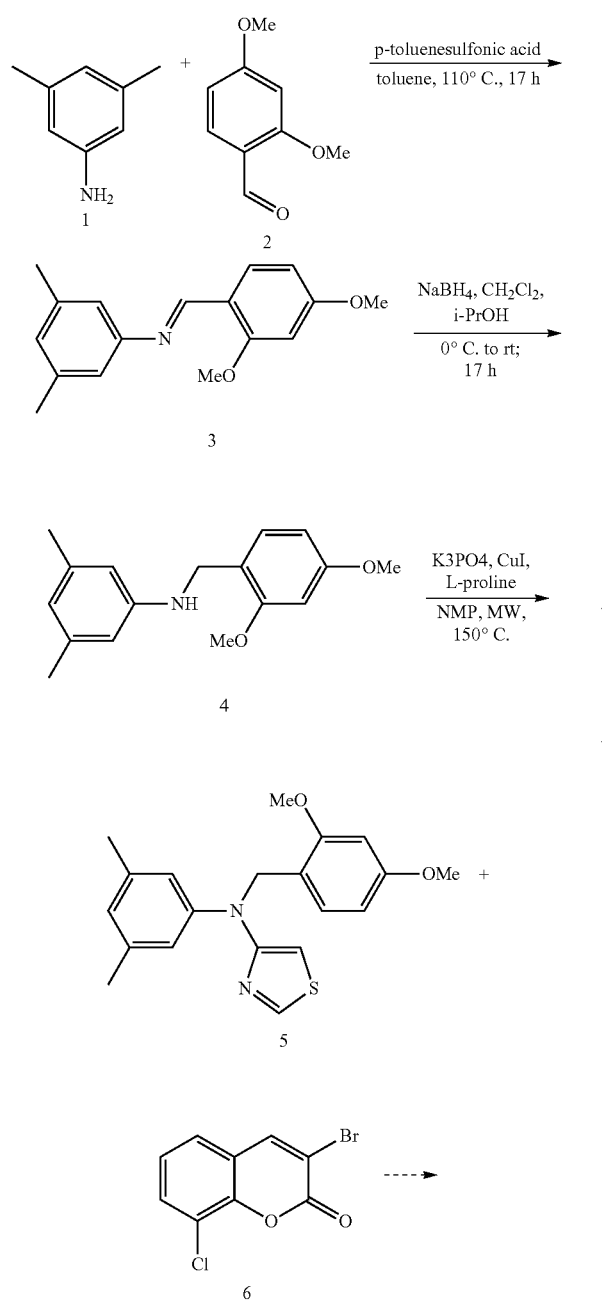

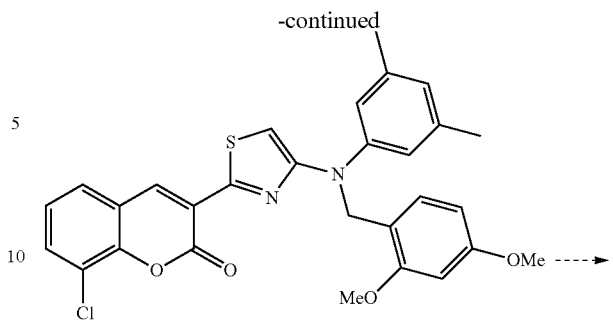

DBM-E-9

Example 2: Assay Design

The compounds described herein are effective for inhibiting cellular proliferation in hyperproliferative cell types. To study the effects of these compounds, an assay was developed to differentiate the effects of the compounds on proliferating versus confluent cells. The assay design generates a proliferating density 24 hours after seeding and provides a 3-day active cell growth/doubling window in which to gauge the anti-proliferative effect of the compounds described herein. For studies of proliferating cells, a seeding density of 1,000-2,000 human hyperproliferative cells per well of 96-well full area well plates was shown to provide a linearity in the doubling of cell number across a 3-day (72 hour) active cell growth/doubling period after a 24-hour seeding period in which cells attach before starting to proliferate. In this 3-day growth window, cell number increases with daily doublings across the 72-hour period (see FIG. 1).

In each assay design, compounds were added at the 24-hour timepoint after cell seeding. The effect of the compounds, relative to vehicle control and to VelCade (a proteasome inhibitor approved in the U.S. for treating relapsed multiple myeloma and mantle cell lymphoma) as a positive control, was assessed across the 3-day growth window for proliferating cells and on an already near confluent culture of cells for the same time period. Normal cells were handled in the same manner, with some adjustment of seeding density needed in select cases. This assay design holds for the data series presented below.

Cell number at the end of the assay was determined using the CELLTITER-GLO Luminescent Cell Viability Assay (Promega; Madison, Wis.). The CELLTITER-GLO Luminescent Cell Viability Assay is a homogeneous method of determining the number of viable cells in culture based on quantitation of the ATP present, an indicator of metabolically active cells. $IC_{50}$ values were calculated. Cell number (number of cells per well) was converted to the % of DMSO matched controls. Each measurement was performed in triplicate. Typical dosage ranges tested were from 250 picomolar to 50 micromolar.

Example 3

The compounds described herein demonstrate nanomolar (nM) selectivity in causing growth arrest of hyperproliferative cancer cells but is without effect on growth and viability of 'normal' non-cancerous human cells until mid-micromolar (μM) concentrations. Two early analogs, Compound DBM 227 and Compound DBM 228, have been evaluated and validated externally by the NCI Developmental Therapeutics Program where they demonstrate nM potency with an average $GI_{50}$ of 250 nM in the NCI-60 cell panel (22 cell lines had $GI_{50}$ values ≤100 nM). For example, Compound DBM-228 was profiled on the NCI 60 human cancer cell line panel (see Table 1). $GI_{50}$ means the growth inhibition of 50%, and represents the drug concentration resulting in a 50% reduction in the net cytosolic ATP increase (as measured by CELLTITER-GLO® (Promega, Madison, Wis.)) in control cells during the drug incubation. TGI means the drug concentration resulting in total growth inhibition or "cytostasis." $LC_{50}$ is the concentration of drug resulting in a 50% reduction in the measured cytosolic ATP at the end of the drug treatment as compared to that at the beginning, indicating a net loss of cells following treatment (cytotoxicity).

TABLE 1

| Panel and Cell Lines | $GI_{50}$ | TGI | $LC_{50}$ |
|---|---|---|---|
| Leukemia Lines | | | |
| CCRF-CEM | 177 nM | 15.4 uM | >100 uM |
| HL-60 | 34 nM | 137 nM | 825 nM |
| K-562 | 43 nM | 16.1 uM | >100 uM |
| MOLT-4 | 168 nM | 17.8 uM | >100 uM |
| RPMI-8226 | 238 nM | 43.9 uM | >100 uM |
| Non-Small Cell Lung Cancer Lines | | | |
| A549 | 97 nM | 22.6 uM | >100 uM |
| HOP-62 | 537 nM | 44.8 uM | >100 uM |
| HOP-92 | 1.45 uM | 24.7 uM | >100 uM |
| NCI-H226 | 11.2 uM | 37.2 uM | >100 uM |
| NCI-H23 | 504 nM | 15.8 uM | 63.1 uM |
| NCI-H322M | 672 nM | 25.9 uM | 93.3 uM |
| NCI-H460 | 91.2 nM | 14.2 uM | >100 uM |
| NCI-H522 | 24.7 nM | 94 nM | >100 uM |
| Colon Cancer Lines | | | |
| COLO 205 | 337 nM | 1.8 uM | >100 uM |
| HCC-2998 | 1.05 uM | 16.5 uM | >100 uM |
| HCT-116 | 79.5 nM | 10 uM | >100 uM |
| HCT-15 | 128 nM | 17.3 uM | >100 uM |
| HT29 | 308 nM | 1.6 uM | 24.7 uM |
| KM12 | 70.5 nM | 13.4 uM | >100 uM |
| SW-620 | 64 nM | >100 uM | >100 uM |
| CNS Cancer Lines | | | |
| SF-268 | 770 nM | 55.3 uM | >100 uM |
| SF-295 | 42.4 nM | 1.49 uM | 41.5 uM |
| SF-539 | 109 nM | 850 nM | 29.8 uM |
| SNB-19 | 182 nM | 35 uM | >100 uM |
| SNB-75 | 48.1 nM | ND | >100 uM |
| U251 | 46.8 nM | 10.6 uM | 35.7 uM |
| Melanoma Lines | | | |
| LOX IMVI | 900 nM | 50.8 uM | >100 uM |
| MALME-3M | 16.8 uM | 49.6 uM | >100 uM |
| M14 | 70.8 nM | ND | 49.9 uM |
| MDA-MB-435 | 23.1 nM | 67.9 uM | 69.5 uM |
| SK-MEL-2 | 86 nM | 28.4 uM | 99.5 uM |
| SK-MEL-28 | 88.9 nM | 31 uM | 99.3 uM |
| SK-MEL-5 | 76.8 nM | 2.3 uM | 26.8 uM |

TABLE 1-continued

| | | | |
|---|---|---|---|
| UACC-257 | ND | 33.7 uM | >100 uM |
| UACC-62 | 51.1 nM | 28.2 uM | >100 uM |
| Ovarian Cancer Lines | | | |
| IGROV1 | 1.23 uM | 23.4 uM | >100 uM |
| OVCAR-3 | 45.6 nM | 322 nM | 24.2 uM |
| OVCAR-4 | 1.35 uM | 25 uM | >100 uM |
| OVCAR-5 | 592 nM | 15.7 uM | 51.9 uM |
| OVCAR-8 | 310 nM | 13.2 uM | >100 uM |
| NCI/ADR-RES | 45.9 nM | 327 nM | >100 uM |
| SK-OV-3 | 410 nM | 22 uM | >100 uM |
| Renal Cancer Lines | | | |
| 786-0 | 709 nM | 15.9 uM | 89.4 uM |
| A498 | 35.4 nM | 4.42 uM | >100 uM |
| ACHN | 1.49 nM | 15.9 uM | 42.7 uM |
| CAKI-1 | 115 nM | 27.9 uM | >100 uM |
| RXF 393 | 218 nM | 15.2 uM | 52.6 uM |
| SN12C | 526 nM | >100 uM | >100 uM |
| TK-10 | 10 uM | 23.5 uM | 55 uM |
| UO-31 | 1.46 uM | 43 uM | >100 uM |
| Prostate Cancer Lines | | | |
| PC-3 | 270 nM | 36 uM | >100 uM |
| DU-145 | 356 nM | 5.31 uM | 41 uM |
| Breast Cancer Lines | | | |
| MCF7 | 54.5 nM | >100 uM | >100 uM |
| MDA-MB-231 | 1.37 uM | 12 uM | >100 uM |
| HS 578T | 13.7 uM | >100 uM | >100 uM |
| BT-549 | 239 nM | 12.3 uM | >100 uM |
| T-47D | ND | 55.9 uM | >100 uM |
| MDA-MB-468 | 47.1 nM | 800 nM | 60.9 uM |

| Complementary DBM In Vitro Profiling Data | GI50 | TGI | LC50 |
|---|---|---|---|
| CNS Cancer Lines | | | |
| T98G | 467 nM | 3.97 uM | 17.6 uM |
| U251MG | 197 nM | >30 uM | >30 uM |
| U118MG | 2.71 uM | 7.85 uM | >30 uM |
| Hematologic Cancer Lines | | | |
| ARH-77 | 154 nM | 339 nM | >30 uM |
| RPMI-8826 | 271 nM | 312 nM | >30 uM |
| U266 | 79.6 nM | 116 nM | 161 nM |
| Ovarian Cancer Lines | | | |
| SK-OV-3 | 845 nM | >30 uM | >30 uM |
| Renal Cancer Lines | | | |
| CAKI-1 | 142 nM | 1.92 uM | 5.21 uM |
| Hypopharyngeal Cancer Lines | | | |
| FaDu | 1.4 uM | 8.74 uM | 27.5 uM |

Figure 2:
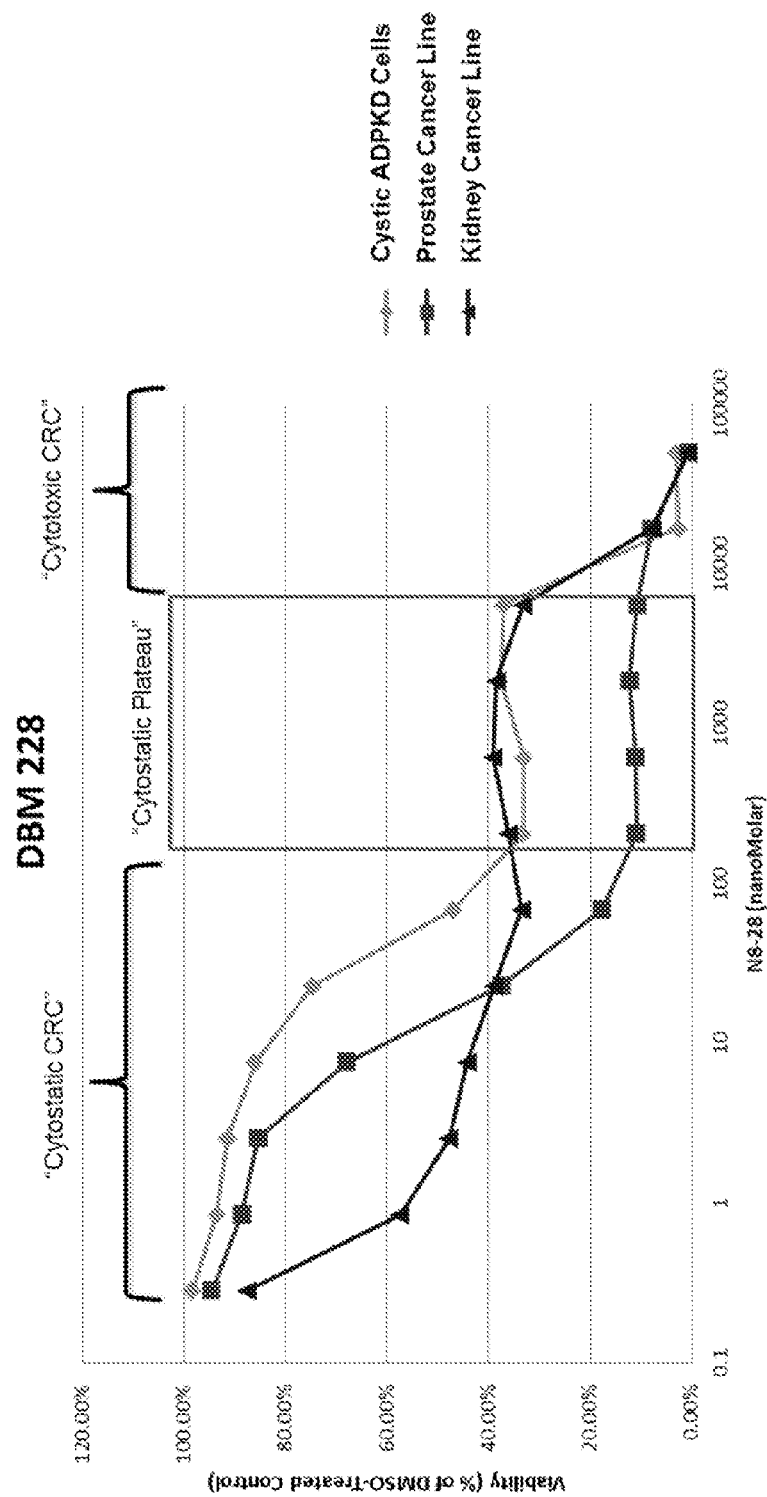
FIG. 2 is a plot showing the viability of Compound DBM 228 in cystic ADPKD cells, in a prostate cancer line, and in a kidney cancer line.

Example 4: Effect of Compound DBM 228 on Human Hyperproliferative Cell Platforms The compounds as described herein were tested on primary human ADPKD cystic epithelial cell lines as well as two common cancer cell lines from the prostate (ARCaP-M) and kidney (CAKI-1). See FIG. 2. The nanomolar ranges generates a cytostatic CRC where the cells are growth arrested but not killed. At and around the 1 micromolar dose in this extended 12-point CRC, there is a cytostatic plateau. At higher mid-micromolar concentrations, there is a cytotoxic effect.

Example 5: Effect of Compound DBM 101 on Proliferating Versus Confluent Human Cystic ADPKD and Non-Cystic Renal Epithelial Cells In Vitro The compounds as described herein were tested on confluent cystic ADPKD cells, proliferating cystic ADPKD cells, confluent normal renal cells, and proliferating normal renal cells. See FIG. 3.

Figure 3:
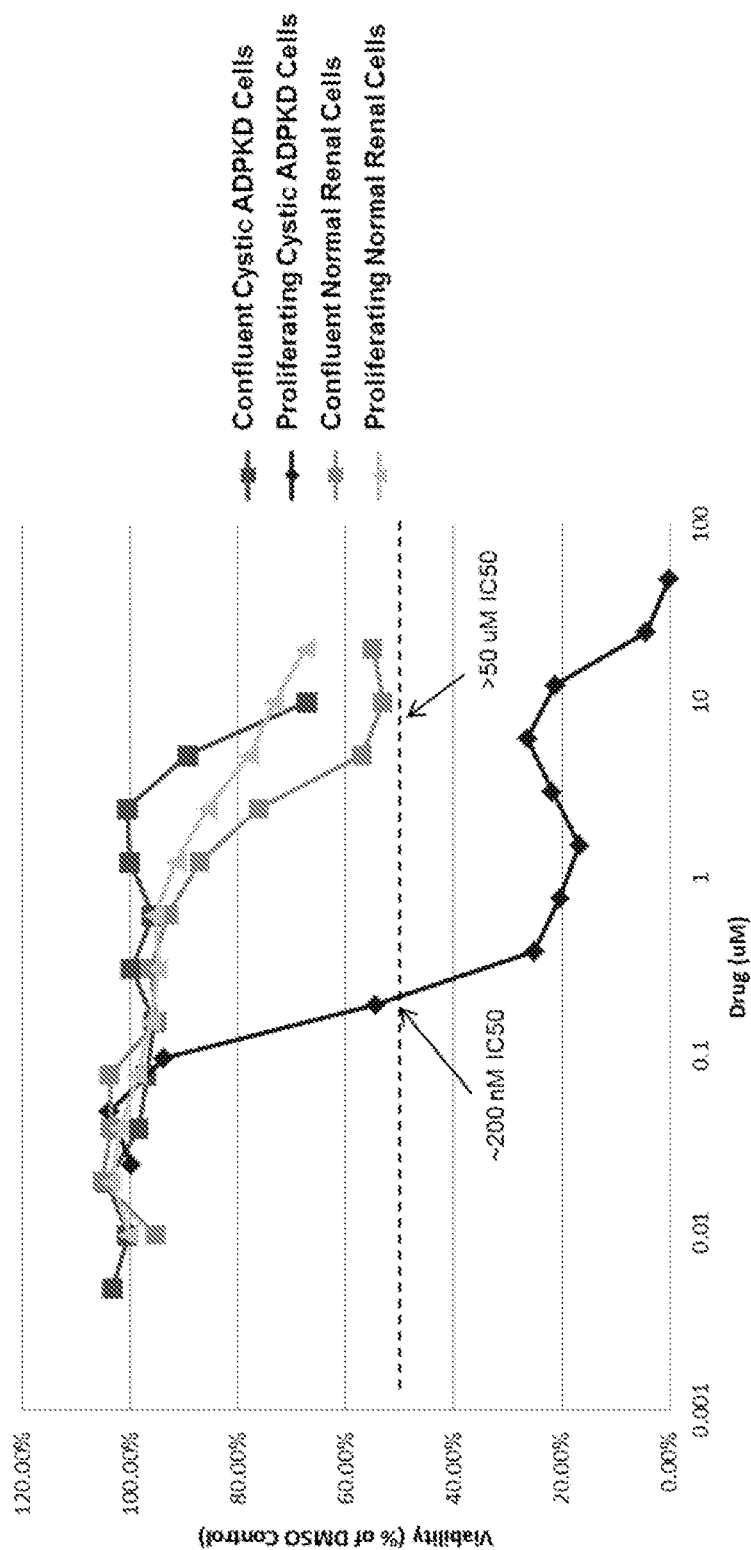
FIG. 3 is a plot showing the viability of Compound DBM 101 in confluent cystic ADPKD cells, in proliferating cystic ADPKD cells, in confluent normal renal cells, and in proliferating normal renal cells.

As shown in FIG. 3, the cytostatic effects of the compounds described herein are selective for hyperproliferative 'diseased' cells at potent nanomolar doses. In sharp contrast, confluent diseased cells and proliferating and confluent normal cells were only partially affected and at mid-micromolar doses.

Example 6: Potency and Efficiency of Compounds

The compounds described herein demonstrate significant potency and efficacy (1 uM $GI_{50}$). For a typical screening experiment to identify the compounds, cells were seeded into 96- or 384-well microtiter plates at plating densities pre-determined for each cell line to ensure drug exposure occurs during the proliferative phase well before confluency is reached. After seeding, cells were incubated for 24 h prior to addition of experimental drugs. After 24 h, a test plate was assayed (CellTiterGlo—measurement of cytosolic ATP) to determine a baseline measurement of the cell population for each cell line at the time of drug addition. Experimental drugs were then added and cells were cultured for a 48 h drug exposure window. After 48 h, cells were assayed and three dose-response parameters were calculated for each experimental agent: (1) growth inhibition of 50% ($GI_{50}$) is the drug concentration resulting in a 50% reduction in the net cytosolic ATP increase (as measured by CellTiterGlo) in control cells during the drug incubation, (2) the drug concentration resulting in total growth inhibition (TGI) or "cytostasis", and (3) $LC_{50}$ or the concentration of drug resulting in a 50% reduction in the measured cytosolic ATP at the end of the drug treatment as compared to that at the beginning indicating a net loss of cells following treatment ("cytotoxicity"). Values were calculated for each of these three parameters if the level of activity was reached; however, if the effect was not reached or was exceeded, the value for that parameter was expressed as greater or less than the maximum or minimum concentration tested. Results are shown in FIG. 4 and Table 2.

TABLE 2

| nM | DBM 227 | DBM 228 | DBM 308 | DBM 318 | DBM 701 | DBM 707 | DBM 717 | DBM 328 |
| --- | --- | --- | --- | --- | --- | --- | --- | --- |
| $GI_{50}$ | 137 | 160 | 166 | 133 | 122 | 131 | 135 | 2106 |
| TGI | 404 | 271 | 247 | 164 | 153 | 183 | 232 | >4,000 |
| $LC_{50}$ | >4,000 | >4,000 | >4,000 | 226 | 193 | 544 | >4,000 | >4,000 |

Figure 4:
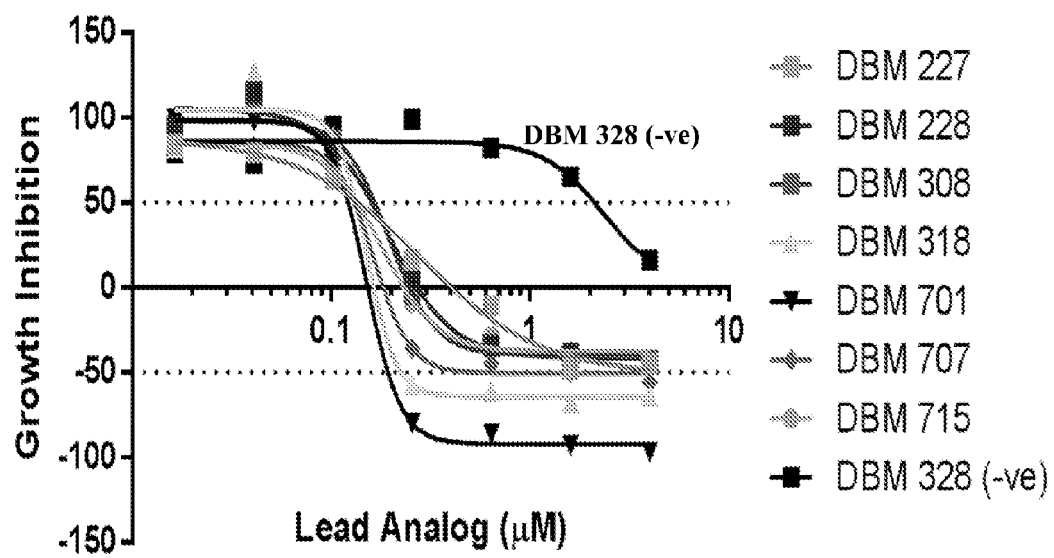
FIG. 4 is a plot showing the growth inhibition of myeloma cells treated with Compound DBM 227, Compound DBM 228, Compound DBM 308, Compound DBM 318, Compound DBM 701, Compound DBM 707, Compound DBM 717, and Compound DBM 328.

As demonstrated in FIG. 4, Compounds DBM 308, DBM 318, DBM 701, DBM 707, and DBM 715 display significant efficacy and potency. Furthermore, these compounds were designed to remove problematic functional groups which may have hampered successful drug development. A dramatic difference in effect was observed when primary normal human cells (i.e., respiratory and renal epithelial cells, dermal keratinocytes, liver hepatocytes, and brain astrocytes) were treated in parallel with these anti-proliferative compounds. The cytostatic effect was not observed in the nM range with any of the best in-class analogs and did not emerge until low µM; cytotoxicity did not occur until the mid-to-high µM range. Given that the most potent analogs have an average $GI_{50}$ of ~250 nM across the NCI-60 panel, there is at least a 2-log separation in effect, or selectivity, on these hyperproliferative cancer cells versus 'normal' human cells.

Example 7: Concentration-Response Effects of Compounds

Figure 5A:
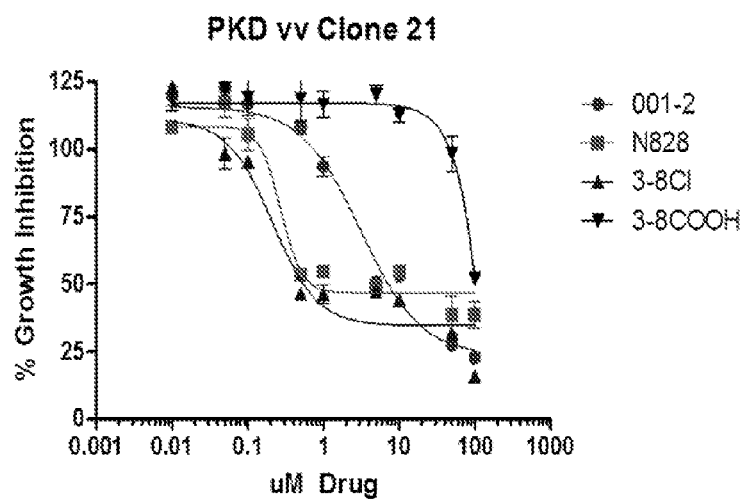
FIG. 5A is a plot showing the growth inhibition of cloned polycystic kidney tissue cells treated with Compound DBM 101 (001-2), Compound DBM 228 (N828), Compound DBM 308 (3-8Cl), and Compound DBM 328 (3-8COOH).
Figure 5B:
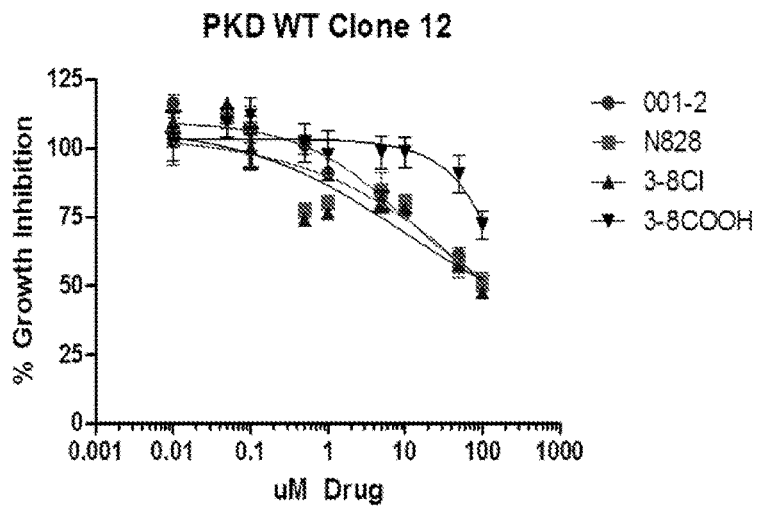
FIG. 5B is a plot showing the growth inhibition of cloned non-cystic kidney tissue cells treated with Compound DBM 101 (001-2), Compound DBM 228 (N828), Compound DBM 308 (3-8Cl), and Compound DBM 328 (3-8COOH).

The concentration-response effects of Compound DBM 228, Compound DBM 308, Compound DBM 101, and Compound DBM 328 were determined in primary cultures derived as 'clones' from cystic versus non-cystic kidney tissue. CRC graphs, $IC_{50}$ values, and the percent maximum inhibition versus lowest doses without effect were calculated with GraphPad Prism software. Compound DBM 308 emerged as a potent and effective analog in this 72 hour treatment and in terms of cytostatic effect. There was also a marked separation in effect between hyperproliferative PKD cells (FIG. 5A and Table 3) and WT cells (FIG. 5B and Table 4).

TABLE 3

| Drug | $IC_{50}$ (µM) | Max inhibition |
| --- | --- | --- |
| 001-2 (DBM 101) | 7.2 | 77% |
| N828 (DBM 308) | 0.69 | 61% |
| 3-8Cl (DBM 308) | 0.54 | 84% |
| 3-8COOH (DBM 328) | 78 | 48% |

TABLE 4

| Drug | $IC_{50}$ (µM) | Max inhibition |
| --- | --- | --- |
| 001-2 (DBM 101) | >100 | 48% |
| N828 (DBM 308) | >100 | 49% |
| 3-8Cl (DBM 308) | >100 | 52% |
| 3-8COOH (DBM 328) | >100 | 28% |

Figure 6:
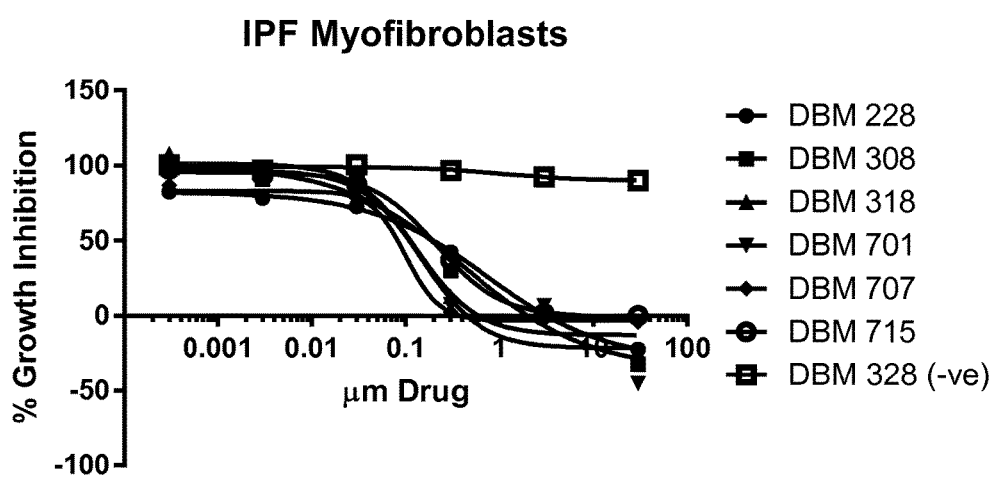
FIG. 6 is a plot showing the growth inhibition of primary human idiopathic pulmonary fibrosis myofibroblasts treated with Compound DBM 228, Compound DBM 308, Compound DBM 318, Compound DBM 701, Compound DBM 707, Compound DBM 715, and Compound DBM 328.

Example 8: Effects of Compounds on the Growth of Primary Human Idiopathic Pulmonary Fibrosis Myofibroblasts In Vitro The anti-proliferative effects of Compounds DBM 228, DBM 308, DBM 318, DBM 701, DBM 707, DBM 715, and DBM 328 were determined on human idiopathic pulmonary fibrosis myofibroblasts. Compound DBM 328 served as a negative control and was without effect throughout the CRC. The results are shown in FIG. 6.

Figure 7:
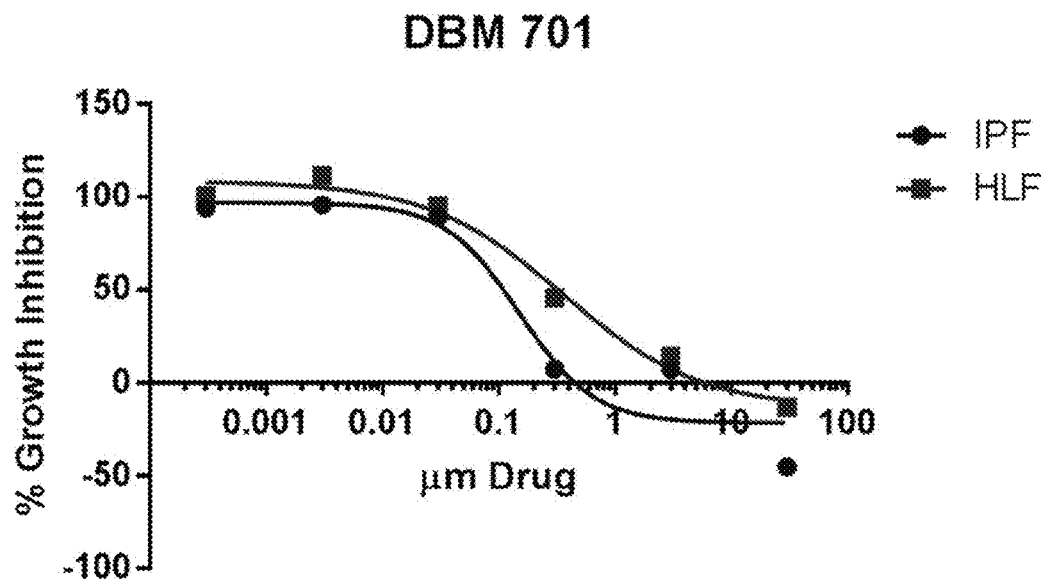
FIG. 7 is a plot showing the growth inhibition of primary human idiopathic pulmonary fibrosis myofibroblasts and primary human chronic obstructive pulmonary disease (COPD) fibroblasts treated with Compound DBM 701.

Example 9: Effects of Compound DBM 701 on the Growth of Primary Human Idiopathic Pulmonary Fibrosis Myofibroblasts In Vitro Versus Primary Human COPD Fibroblasts The separation in effect of Compound DBM 701 on the growth of primary human idiopathic pulmonary fibrosis (IPF) myofibroblasts was determined and compared to that of primary human COPD fibroblasts. The results are shown in FIG. 7 and Table 5. There was less separation in effect between IPF hyperproliferative myofibroblasts and fibroblasts isolated from COPD lungs; however, a significant separation was observed.

TABLE 5

|  | GI$_{50}$ (µM) | TGI (µM) | LC$_{50}$ (µM) |
| --- | --- | --- | --- |
| IPF | 0.109 | 0.450 | >30 |
| COPD | 0.318 | 5.9 | >30 |

Figure 8:
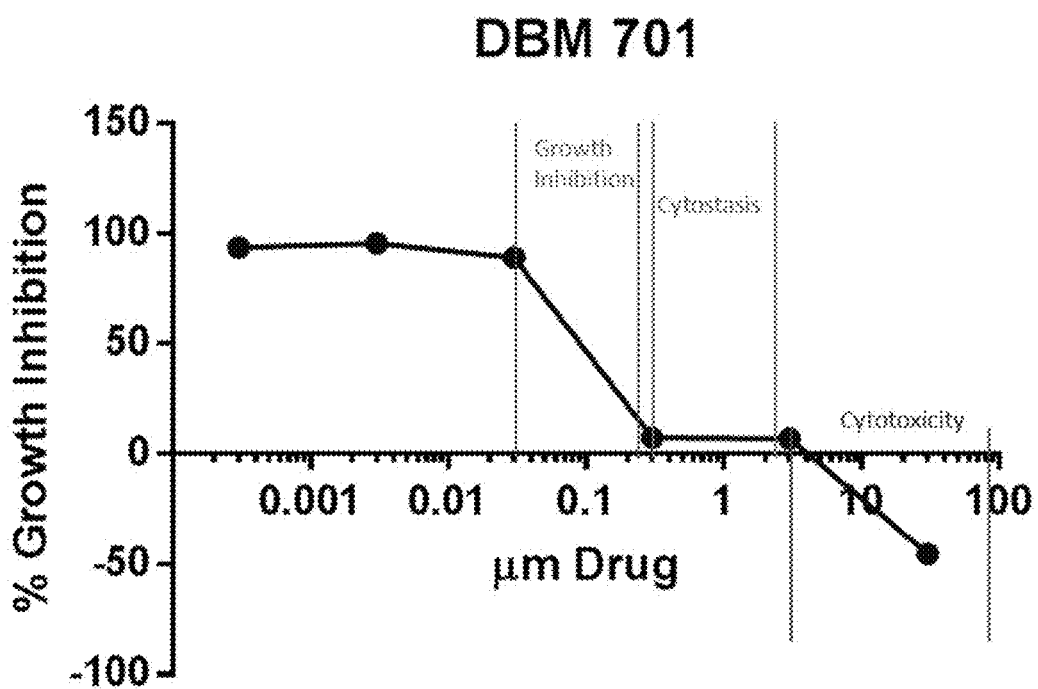
FIG. 8 is a plot showing the growth inhibition of primary human idiopathic pulmonary fibrosis myofibroblasts treated with Compound DBM 701.

The 'double' CRC was observed with Compound DBM 701 on the growth of primary human idiopathic pulmonary fibrosis (IPF) myofibroblasts. Growth inhibition and cytostasis was observed in the nanomolar range up to 1 micromolar and cytotoxicity was starting to emerge in the micromolar range for Compound DBM 701 (FIG. 8).

Figure 9:
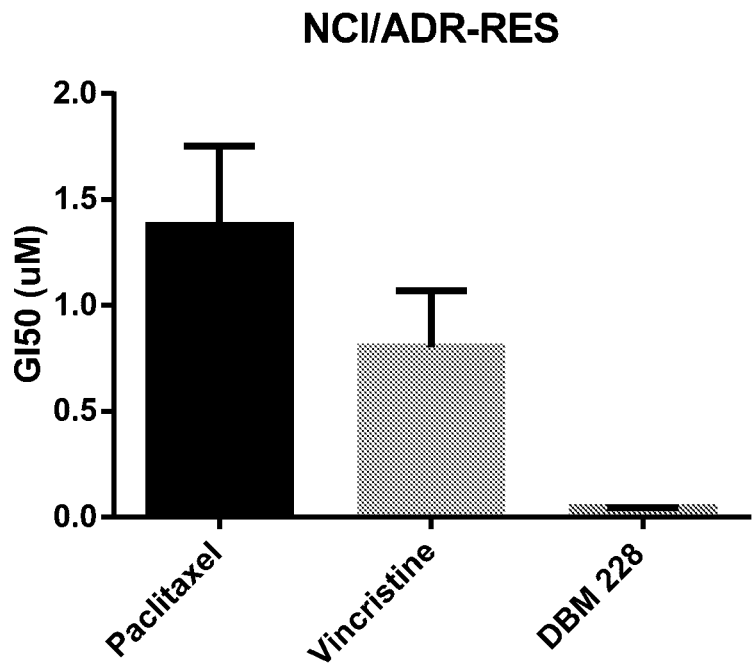
FIG. 9 is a graph showing the inhibition of the multi-drug resistant NCI/ADR-RES ovarian carcinoma cell line after treatment with paclitaxel, vincristine, and Compound DBM 228.

Example 10: In Vitro Anti-Proliferative Efficacy Against Multi-Drug Resistant Cancer A major limitation with the anti-mitotic drugs in particular and in conventional chemotherapeutics in general, is their susceptibility to cellular mechanisms of adaptive/intrinsic multi-drug resistance (i.e., MDR efflux pumps such as p-glycoprotein, MRP1). The compounds described herein, however, including Compound DBM 227 and Compound DBM 228, demonstrated superior potency in the NCI-ADR/RES cell line (100 nM and 44.5 nM, respectively). This cell line expresses high levels of MDR1 and P-glcyoprotein and represents a good model for profiling compounds in an in vitro cell model of cancer multi-drug resistance. In drug-responsive cells found within the NCI-60 panel, agents such as paclitaxel and vincristine demonstrate potent cytotoxicity with GI$_{50}$ values often in the range of 1-10 nM. However, in the multi-drug resistant NCI-ADR/RES cell line, the potency of these common drugs is significantly right-shifted, whereas Compound DBM 228 remained potent (FIG. 9). The compound also displayed significant potency in the OVCAR-3 and SK-OV-3 cell lines (50 nM and 330 nM GI$_{50}$, respectively) which are known to demonstrate resistance to several clinically relevant drugs including adriamycin, melphalan and cisplatin. Thus, the compounds described herein can be effective in treating multi-drug resistant cancer.

Figure 10:
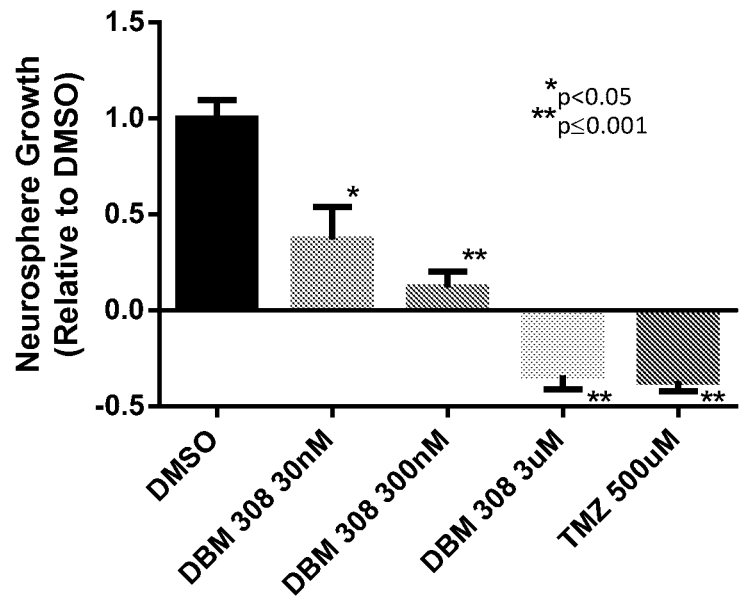
FIG. 10 is a graph showing the neurosphere growth of primary human glioblastoma multiforme cells after treatment with various doses of Compound DBM 308 (30 nM, 300 nM, and 3 µM), temozolomide (TMZ) (500 µM), and DMSO.

Example 11: Dose-dependent Growth Arrest to Cytotoxic Effect on Primary Human Glioblastoma Multiforme (GBM) Cells The compounds described herein are much more potent than known first-line anti-cancer drugs, such as temozolomide (TMZ) which was only cytotoxic and at high micromolar doses. As shown in FIG. 10, Compound DBM 308 demonstrates a dose-dependent growth arrest to cytotoxic effect on primary human glioblastoma multiforme (GBM) cells grown in vitro on 3D neurospheres. Compound DBM 308 has a cytostatic effect at nanomolar doses and an equivalent cytotoxic effect to TMZ (but at 3 micromolar versus 500 micromolar). Data are expressed as mean±SEM and represent at least two independent experiments with sample replicates.

Example 12: Cell Cycle Arrest

Figure 11A:
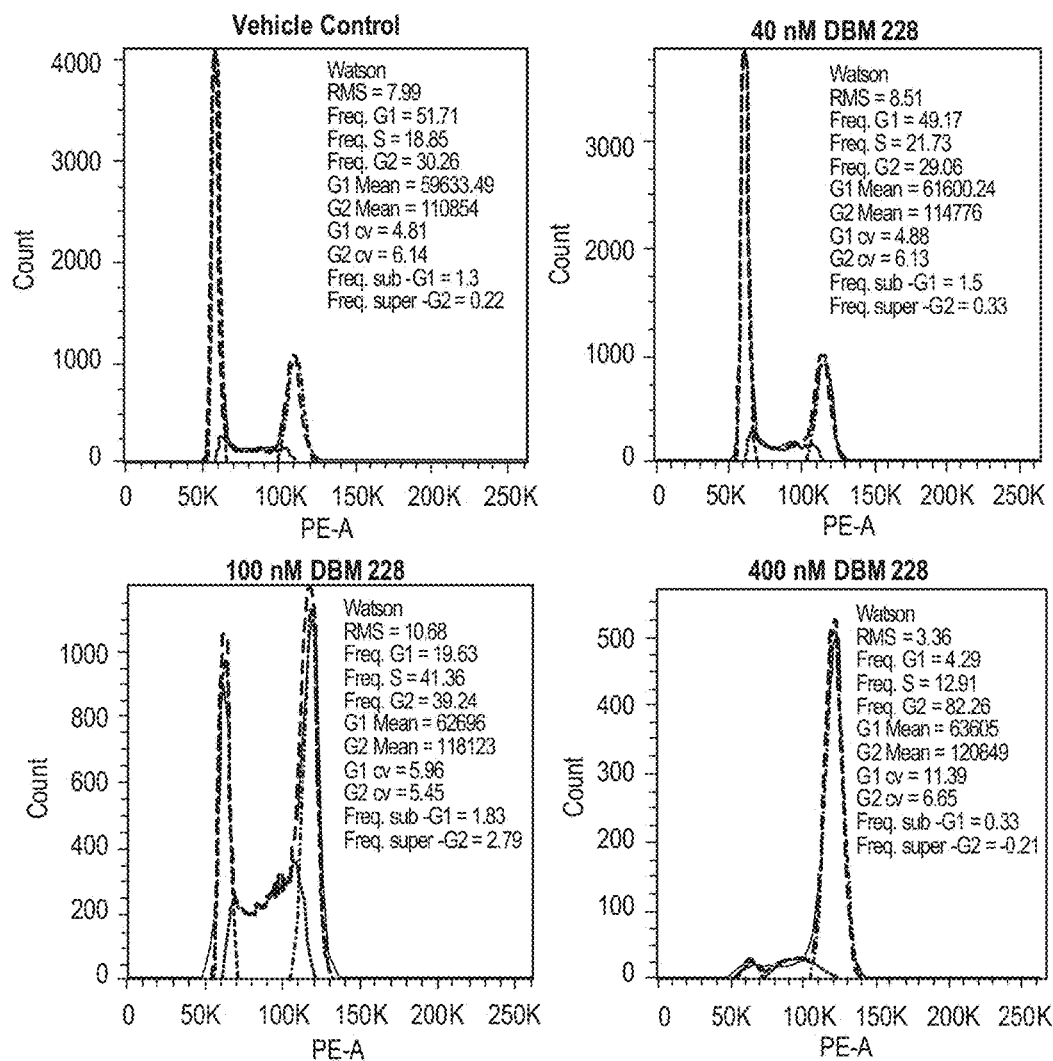
FIG. 11A contains graphs showing U251MG glioblastoma cells tested with increasing concentrations of Compound DBM 228 (upper left panel: control; upper right panel: 40 nM Compound DBM 228; lower left panel: 100 nM Compound DBM 228; lower right panel: 400 nM Compound DBM 228).

Cell cycle analysis was performed on U251-MG cells to determine at what point in the cell cycle the compounds described herein were acting. U251MG glioblastoma cells were treated for 24 h with increasing concentrations of Compound DBM 228. Propidium iodide-based cell cycle analysis revealed G2/M arrest (see FIG. 11A and Table 6).

TABLE 6

|  | Control (DMSO) | 40 nM | 100 nM | 400 nM |
| --- | --- | --- | --- | --- |
| Pre-G$_0$/G$_1$ | 1.7% | 3.2% | 13.6% | 43.1% |
| G$_0$/G$_1$ | 54.1% | 52.2% | 19.7% | 1.8% |
| S | 13.3% | 14.4% | 25.6% | 5.8% |
| G$_2$/M | 30.9% | 30.2% | 41.1% | 49.3% |

Table 6 shows the percentage of cells identified in different phases of the cell cycle. Increased percentages of cells were observed in G2/M phase, indicating G2/M phase block. However, at higher nM doses, the cells appear to progress toward apoptosis and programmed cell death, given the higher % of cells in pre-G0/G1.

Figure 11B:
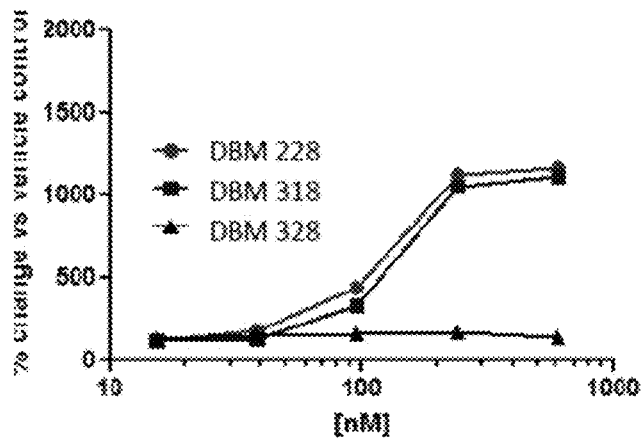
FIG. 11B is a graph showing the percent change in caspase 3/7 activation in U251MG cells treated with Compound DBM 228, Compound DBM 318, and Compound DBM 328.
Figure 11C:
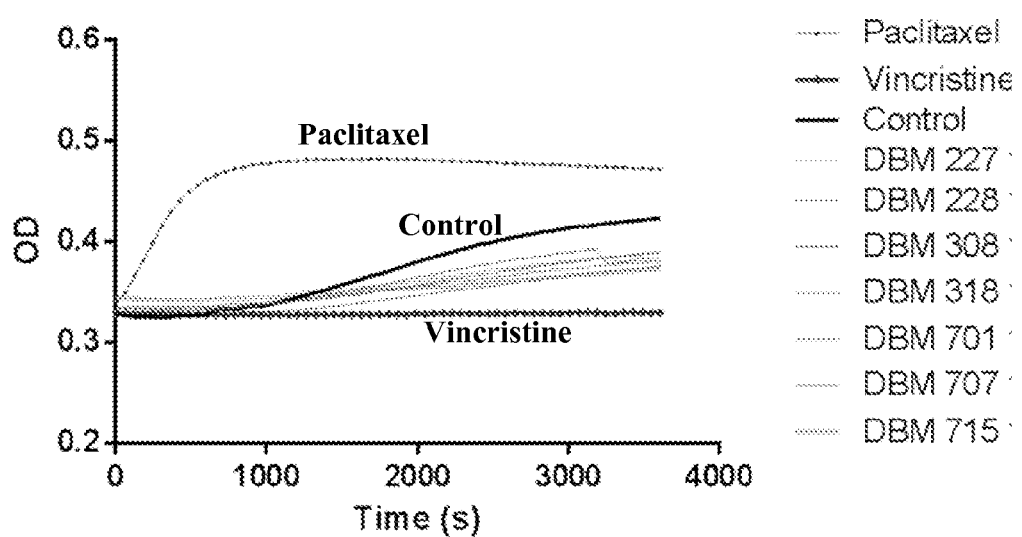
FIG. 11C is a graph showing the inhibition of biochemical tubulin polymerization after treatment with paclitaxel, vincristine, a control (Compound DBM 328), Compound DBM 227, Compound DBM 228, Compound DBM 308, Compound DBM 318, Compound DBM 701, Compound DBM 707, and Compound DBM 715.

Following 24 hours of treatment with Compound DBM 228, Compound DBM 318, and Compound DBM 328, caspase 3/7 activation in U251MG cells was determined. The detection of caspase 3/7 activation in U251MG cells indicates activation of apoptosis. The results are shown in FIG. 11B. Tubulin polymerization was determined for Compounds DBM 227, DBM 228, DBM 308, DBM 318, DBM 701, DBM 707, DBM 715, paclitaxel, vincristine, and negative control Compound DBM 328. Biochemical tubulin polymerization was modestly inhibited by Compounds DBM 227, DBM 228, DBM 308, DBM 318, DBM 701, DBM 707, and DBM 715. Paclitaxel served as polymerization enhancer control and vincristine served as polymerization inhibitor control. The negative control, DBM 328, also inhibited microtubule polymerization.

Figure 12:
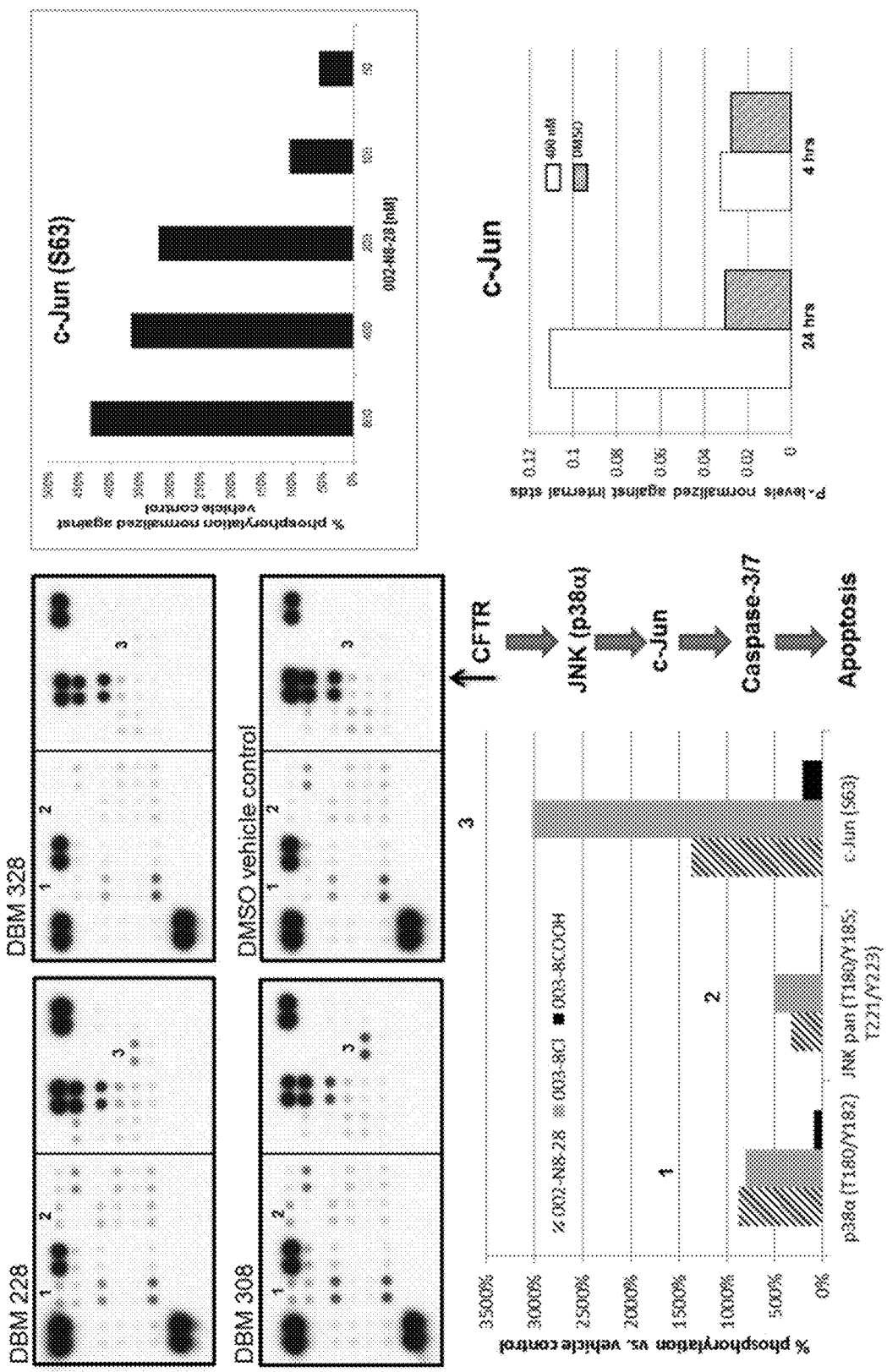
FIG. 12 contains the results of an intracellular signaling molecule phosphor-array for human hyperproliferative GBM cancer cells after treatment with Compound DBM 228, Compound DBM 328, Compound DBM 308, or a DMSO vehicle control (upper left panel); a plot of the percent phosphorylation vs. vehicle control for Compound DBM 228 (002-N8-28), Compound DBM 308 (003-8Cl), and Compound DBM 328 (003-8COOH) for p38α, JNK pan, and c-Jun phosphorylation (lower left panel); a dose-response effect is provided for Compound DBM 228 (002-N8-28) for potentiation of c-Jun phosphorylation (upper right panel); and a plot of the time dependence of the effect for Compound DBM 228's (002-N8-28) potentiation of c-Jun phosphorylation.

Example 13: Intracellular Signaling Molecule Phospho-Array in Drug-Treated Versus Vehicle-Treated Human Hyperproliferative GBM Cancer Cells An intracellular signaling molecule phospho-array was performed in compound-treated human hyperproliferative GBM cancer cells and in vehicle-treated human hyperproliferative GBM cancer cells. The tested compounds included Compound DBM 228 (002-N8-28), Compound DBM 328 (003-8COOH), and Compound DBM 308 (003-8Cl). DMSO served as the vehicle control. The results are shown in FIG. 12. The numbers reflect pairs of spots in the typical dot blots that correspond to major kinases and other signaling proteins. Compound DBM 328 (003-8COOH) is a negative control for this array experiment to complement the DMSO vehicle control. A dose-response effect is provided for Compound DBM 228 (002-N8-28) for potentiation of c-Jun phosphorylation (see top right panel of FIG. 12) as well as the time-dependence of the effect requiring 24 hours (see bottom right panel of FIG. 12).

Example 14: Vimentin Phosphorylation and Diassembly in Human Hyperproliferative Diseases Vimentins are a class of intermediate filaments that are widely expressed in a variety of cultured cells, including mesenchymal and tumor cells. They constitute part of the cytoskeleton's scaffolding network, where their roles include maintenance of cell shape, division, migration, secretion, signaling molecule distribution, wound healing, and smooth muscle force development. The intracellular organization of filamentous vimentin networks is regulated by phosphorylation events by a series of protein kinases and phosphatases.

In particular, vimentin phosphorylation has a role in regulating spatial reorganization via disassembly of vimentin filaments in vitro. Disassembly of vimentin filaments also leads to an increase in single 'activated' subunits, which signal caspase-dependent apoptotic events. Vimentin represents the most common intermediate filament present in mitosis, where hyperphosphorylation of vimentin is observed. For example, phosphorylation of vimentin at specific serine residues has been demonstrated to occur at the cleavage furrow during cytokinesis.

Specific kinases and phosphatases are implicated in vimentin regulation. For example, P21-activated kinases and cyclin dependent kinases (cdk) regulate vimentin at S56. In addition, Cdk5 mediates vimentin phosphorylation at Ser-56, where vimentin participates in GTP-induced secretion by neutrophils.

A custom, high sensitivity and comprehensive proteomics study was performed to analyze the effect of Compound DBM 308 on vimentin. Vehicle and Compound DBM 328 (an inactive analog) controls were performed in parallel. The proteomics data showed a 24.22 fold up-regulation in vimentin phosphorylated at a critical serine residue 56. The DMSO vehicle control was 1.0 and the inactive analog Compound DBM 308 control was 1.4 (P=0.0006–most significant change in the data–99% of proteins in the proteomics array were unaffected). The proteomics data revealed that several kinases, such as Cdk5, were differentially regulated in Compound DBM 308 treated cells versus the controls.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A method for treating polycystic kidney disease in a subject, comprising:
   administering to a subject an effective amount of a compound of the following formula:

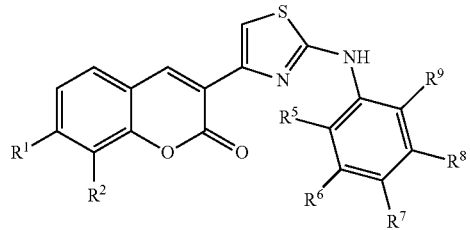

or a pharmaceutically acceptable salt or prodrug thereof, wherein:
$R^1$ is hydrogen, halogen, substituted or unsubstituted amino, or substituted or unsubstituted $C_{1-6}$ alkyl;
$R^2$ is halogen, nitro, trifluoromethyl, substituted or unsubstituted amino, or substituted or unsubstituted $C_{1-6}$ alkyl; and
$R^5$, $R^6$, $R^7$, $R^8$, and $R^9$ are each independently selected from hydrogen, halogen, substituted or unsubstituted alkoxy, trifluoromethyl, or substituted or unsubstituted $C_{1-6}$ alkyl.

2. The method of claim 1, wherein
$R^2$ is $C_{1-6}$ alkyl, halogen, or trifluoromethyl; and
$R^5$, $R^6$, $R^7$, $R^8$, and $R^9$ are each independently selected from hydrogen and methoxy.

3. The method of claim 1, wherein $R^5$ is substituted or unsubstituted alkoxy.

4. The method of claim 1, wherein the compound is

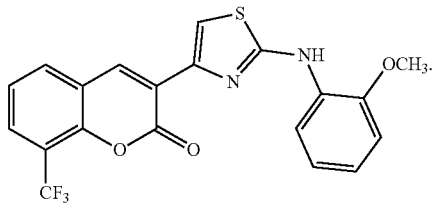 [SMILES: COc1ccccc1Nc1nc(-c2cc3cccc(C(F)(F)F)c3oc2=O)cs1]

5. A method for treating polycystic kidney disease in a subject, comprising:
   administering to a subject an effective amount of a compound selected from the group consisting of:

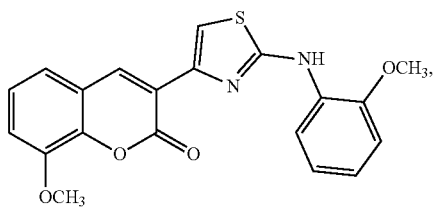

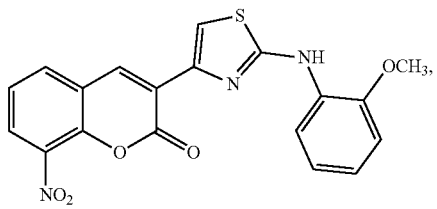

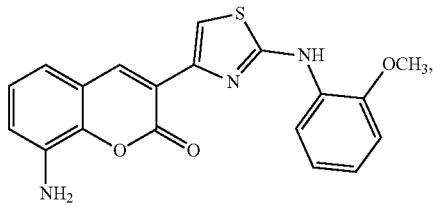

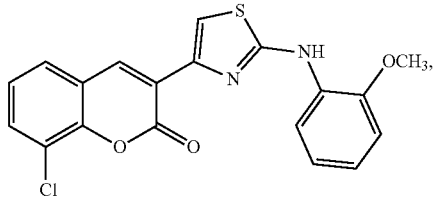

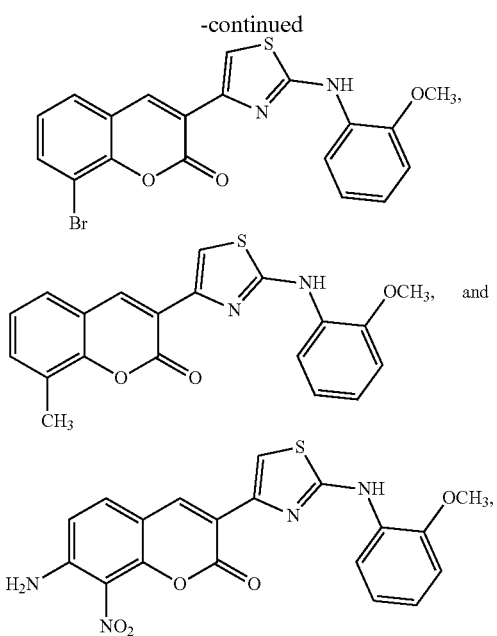
or a pharmaceutically acceptable salt or prodrug thereof.
* * * * *